(12) United States Patent
Szabó et al.

(10) Patent No.: US 12,370,182 B2
(45) Date of Patent: Jul. 29, 2025

(54) BICYCLIC DERIVATIVES AS GABAA A5 RECEPTOR MODULATORS

(71) Applicant: RICHTER GEDEON NYRT., Budapest (HU)

(72) Inventors: György Szabó, Budapest (HU); György István Túrós, Budapest (HU); Olivér Éliás, Marcali (HU); Benedek Imre Károlyi, Budapest (HU); Péter Erdélyi, Budapest (HU); Gábor Kapus, Pécel (HU)

(73) Assignee: RICHTER GEDEON NYRT., Budapest (HU)

( * ) Notice: Subject to any disclaimer, the term of this patent is extended or adjusted under 35 U.S.C. 154(b) by 1158 days.

(21) Appl. No.: 17/279,654

(22) PCT Filed: Sep. 27, 2019

(86) PCT No.: PCT/IB2019/058208
§ 371 (c)(1),
(2) Date: Mar. 25, 2021

(87) PCT Pub. No.: WO2020/065597
PCT Pub. Date: Apr. 2, 2020

(65) Prior Publication Data
US 2021/0386718 A1    Dec. 16, 2021

(30) Foreign Application Priority Data
Sep. 28, 2018 (HU) .................................. P1800333

(51) Int. Cl.
| | |
|---|---|
| *A61K 31/4375* | (2006.01) |
| *A61K 31/437* | (2006.01) |
| *A61K 31/444* | (2006.01) |
| *A61K 31/5377* | (2006.01) |
| *C07D 471/04* | (2006.01) |

(52) U.S. Cl.
CPC ........ *A61K 31/4375* (2013.01); *A61K 31/437* (2013.01); *A61K 31/444* (2013.01); *A61K 31/5377* (2013.01); *C07D 471/04* (2013.01)

(58) Field of Classification Search
CPC ...... A61K 31/437; C07D 471/04; A61P 25/00
See application file for complete search history.

(56) References Cited

FOREIGN PATENT DOCUMENTS

| | | |
|---|---|---|
| WO | WO 1998/50385 A1 | 11/1998 |
| WO | WO 1999/67245 A1 | 12/1999 |
| WO | WO 2002/06285 A1 | 1/2002 |
| WO | WO 2007/018660 A2 | 2/2007 |
| WO | WO 2007/047991 A1 | 4/2007 |
| WO | WO 2007/140174 A3 | 12/2007 |
| WO | WO 2008/157270 A1 | 12/2008 |
| WO | WO 2009/071464 A1 | 6/2009 |
| WO | WO 2009/071476 A1 | 6/2009 |
| WO | WO 2009/071477 A1 | 6/2009 |
| WO | WO 2010/097368 A1 | 9/2010 |
| WO | WO 2010/112475 A1 | 10/2010 |
| WO | WO 2010/127978 A1 | 11/2010 |
| WO | WO 2013/007387 A1 | 1/2012 |
| WO | WO 2012/059482 A1 | 5/2012 |
| WO | WO 2012/062623 A1 | 5/2012 |
| WO | WO 2012/062687 A1 | 5/2012 |
| WO | WO 2013/057123 A1 | 4/2013 |
| WO | WO 2013/079452 A1 | 6/2013 |
| WO | WO 2014/001278 A1 | 1/2014 |

(Continued)

OTHER PUBLICATIONS

Asai, Y., et al., "GABAA/Benzodiazepine receptor binding in patients with schizophrenia using [$^{11}$C]Ro15-4513, a radioligand with relatively high affinity for α5 subunit," *Schizophrenia Res* 99:333-340, Elsevier, Netherlands (2008).

Atack, J.R., et al., "L-655,708 enhances cognition in rats but is not proconvulsant at a dose selective for α5-containing GABA$_A$ receptors," *Neuropharmacology* 51:1023-102, Elsevier, Netherlands (2006).

Atack, J.R., et al., "In Vitro and in Vivo Properties of 3-tert-Butyl-7-(5-methylisoxazol-3-yl)-2-(1-methyl-1H-1,2,4-triazol-5-ylmethoxy)-pyrazolo[1,5-d]-[1,2,4]triazine (MRK-016), a GABAA Receptor α5 Subtype-Selective Inverse Agonist," *J Pharmacol Exp Ther* 331(2):470-484, The American Society for the Pharmacology and Experimental Therapeutics, United States (2009).

Atack, J.R., "Preclinical and clinical pharmacology of the GABAA receptor alpha5 subtype-selective inverse agonist alpha5IA," *Pharmacol Ther* 125:11-26, Elsevier, Netherlands (2010).

(Continued)

*Primary Examiner* — Kamal A Saeed
(74) *Attorney, Agent, or Firm* — Sterne, Kessler, Goldstein & Fox P.L.L.C.

(57) ABSTRACT

The present invention provides compounds of formula (I) and/or salt thereof and/or geometric isomer thereof and/or stereoisomer thereof and/or enantiomer thereof and/or racemate thereof and/or diastereomer thereof and/or biologically active metabolite thereof and/or prodrug thereof and/or solvate thereof and/or hydrate thereof and/or polymorph thereof having affinity and selectivity for the gamma-aminobutyric acid A receptor subunit alpha 5 and act as GABA$_A$ α5 negative allosteric modulators, thereby useful in the treatment or prevention of diseases related to the GABA$_A$ α5 receptor, process for the preparation thereof, pharmaceutical compositions comprising them alone or in combination with one or more other active ingredients and their use as medicaments.

(I)

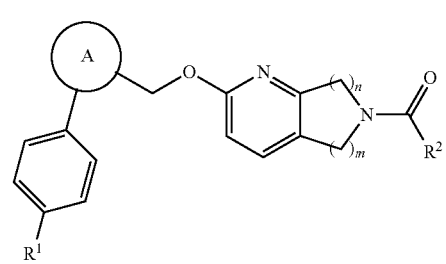

19 Claims, No Drawings

(56) References Cited

FOREIGN PATENT DOCUMENTS

| WO | WO 2014/001281 A1 | 1/2014 |
|---|---|---|
| WO | WO 2016/107832 A1 | 7/2016 |
| WO | WO 2017/133521 A1 | 8/2017 |

OTHER PUBLICATIONS

Ballard, T.M., et al., "RO4938581, a novel cognitive enhancer acting at GABAA α5 subunit-containing receptors," *Psychopharmacology* 202:207-223, Springer-Verlag, Germany (2008).
Bednar, M., et al., "Plasma and cerebrospinal fluid (CSF) pharmacokinetics of CP-457,920, a selective alpha 5 GABA-A receptor inverse agonist in young, healthy volunteers," *Clin Pharmacol Ther* 75:P30, Abstract PI-105, Wiley—Blackwell, United States (2004).
Behlke, L.M., et al., "A Pharmacogenetic 'Restriction-of-Function' Approach Reveals Evidence for Anxiolytic-Like Actions Mediated by α5-Containing GABAA Receptors in Mice," *Neuropsychopharmacology* 41:2492-2501, American College of Neuropsychopharmacology, United States (2016).
Biawat, P., "The synthesis of alpha 5 subtype selective GABA(A)/ Benzodiazepine Receptors Ligands", Thesis and Dissertation at The University of Wisconsin Milwaukee, UWM Digital Commons, 88 pages (Aug. 2014).
Bittel, D.C., et al., "Microarray analysis of gene/transcript expression in Prader-Willi syndrome: deletion versus Upd," *J Med Genet* 40:568-574, BMJ Publishing Group, United Kingdom (2003).
Blaszczyk, J.W., "Parkinson's Disease and Neurodegeneration: GABA-Collapse Hypothesis," *Front Neurosci* 10(269):1-8, Frontiers Media SA, Switzerland (2016).
Bollmann et al., "Developmental changes in gamma-aminobutyric acid levels in attention-deficit/hyperactivity disorder" *Transl Psychiatry* 8:e589:1-8, Nature Publishing Group, Germany (2015).
Bolognani et al., "RG1662, a Selective GABAA α5 Receptor Negative Allosteric Modulator, Increases Gamma Power in Young Adults with Down Syndrome, (P6.273)," *Neurology* 84(14):P6.273, Springer Science+Business Media, Germany (2015).
Botta, P., et al., "Regulating anxiety with extrasynaptic inhibition," *Nat Neuroscience* 18:1493-1500, Nature Portfolio, United Kingdom (2015).
Braudeau, J., et al., "Specific targeting of the GABA-A receptor a5 subtype by a selective inverse agonist restores cognitive deficits in Down syndrome mice," *J Psychopharmacol* 25(8):1030-1042, SAGE, United States (2011).
Bravo-Hernández, M., et al., "Evidence for the participation of peripheral a5 subunit-containing GABAA receptors in GABAA agonists-induced nociception in rats," *Eur J Pharmacol.* 734:91-97, Elsevier, Netherlands (2014).
Caraiscos, V.B., et al., "Tonic inhibition in mouse hippocampal CA1 pyramidal neurons is mediated by α5 subunit-containing γ-aminobutyric acid type A receptors," *PNAS* 101(10):3662-3667, The National Academy of Sciences, United States (2004).
Carreno, F.R., et al., "Selective Pharmacological Augmentation of Hippocampal Activity Produces a Sustained Antidepressant-Like Response without Abuse-Related or Psychotomimetic Effects," *Int J Neuropsychopharmacol* 20(6):504-509, Oxford University Press, United Kingdom (2017).
Chambers, M.S., et al., "Identification of a Novel, Selective $GABA_A$ α5 Receptor Inverse Agonist Which Enhances Cognition," *J Med Chem* 46(11):2227-2240, American Chemical Society, United States (2003).
Cheng, V.Y., et al., "α5$GABA_A$ Receptors Mediate the Amnestic But Not Sedative-Hypnotic Effects of the General Anesthetic Etomidate," *J Neurosci* 26(14):3713-3720, Society for Neuroscience, United States (2006).
Choudary, P.V., et al., "Altered cortical glutamatergic and GABAergic signal transmission with glial involvement in depression," *PNAS* 102(43):15653-15658, The National Academy of Sciences, United States (2005).

Clarkson, A.N., et al., "Reducing excessive GABA-mediated tonic inhibition promotes functional recovery after stroke," *Nature* 468(7321):305-309, Nature Research, United Kingdom (2010).
Collinson, N., et al., "An inverse agonist selective for α5 subunit-containing GABAA receptors improves encoding and recall but not consolidation in the Morris water maze," *Psychopharmacology* 188:619-628, Springer-Verlag, Germany (2006).
Collinson, N., et al., "Enhanced learning and memory and altered GABAergic synaptic transmission in mice lacking the alpha 5 subunit of the $GABA_A$ receptor," *J Neurosci* 22(13):5572-5580, Society for Neuroscience, United States (2002).
Crestani, F., et al., "Trace fear conditioning involves hippocampal alpha5 $GABA_A$ receptors," *PNAS* 99:8980-8985, The National Academy of Sciences, United States (2002).
Curia, G., et al., "Downregulation of Tonic GABAergic Inhibition in a Mouse Model of Fragile X Syndrome," *Cereb Cortex* 19:1515-1520, Oxford University Press, United Kingdom (2009).
Darmani, G., et al., "Effects of the selective α 5-GABAAR antagonist S44819 on excitability in the human brain: a TMS-EMG and TMS-EEG Phase I Study," *J Neurosci.* 36:12312-12320, Society for Neuroscience, United States (2016).
Dawson, G.R., et al., "An Inverse Agonist Selective for α5 Subunit-Containing GABAA Receptors Enhances Cognition," *J Pharmacol Exp Ther.* 316(3):1335-1345, The American Society for Pharmacology and Experimental Therapeutics, United States (2006).
Du, Z., et al., "Differential Alteration in Expression of Striatal $GABA_A$R Subunits in Mouse Models of Huntington's Disease," *Front Mol Neurosci.* 10(198):1-16, Frontiers Media S.A., Switzerland (2017).
Edden, R., et al., "Reduced GABA Concentration in Attention-Deficit/Hyperactivity Disorder," *Arch Gen Psychiatry* 69:750-753, American Medical Association, United States (2014).
Fischell, J., et al., "Rapid Antidepressant Action and Restoration of Excitatory Synaptic Strength After Chronic Stress by Negative Modulators of Alpha5-Containing $GABBA_A$ Recptors," *Neuropsychopharmacology* 40:2499-2509, Nature Publishing Group, Germany (2015).
Foster, A.C., and Kemp, J.A., "Glutamate- and GABA-based CNS therapeutics," *Curr Opin Pharmacol* 6:7-17, Elsevier, Netherlands (2006).
Fritschy, J-M., and Möhler, H., "GABAA-receptor heterogeneity in the adult rat brain: differential regional and cellular distribution of seven major subunits." *J Comp Neurol* 359:154-194, Wiley-Liss, Inc., United States (1995).
Gacsályi, I., et al., "Behavioural pharmacology of the α5-GABAA receptor antagonist S44819: Enhancement and remediation of cognitive performance in preclinical models," *Neuropharmacology* 125:30-38, Elsevier, Netherlands (2017).
Gacsályi, I., et al., "Persistent therapeutic effect of a novel α5-$GABA_A$ receptor antagonist in rodent preclinical models of vascular cognitive impairment," *Eur J Pharmacol* 834:118-125, Elsevier, Netherlands (2018).
Gallos, G., et al., "Selective targeting of the α5-subunit of $GABA_A$ receptors relaxes airway smooth muscle and inhibits cellular calcium handling," *Am J Physiol Lung Cell Mol Physiol* 308:L931-942, The American Physiological Society, United States (2015).
Gill, K.M., et al., "A Novel α5$GABA_A$R-Positive Allosteric Modulator Reverses Hyperactivation of the Dopamine System in the MAM Model of Schizophrenia," *Neuropsychopharmacology* 36:1903-1911, American College of Neuropsychopharmacology, United States (2011).
Glykis, J., et al., "Which GABAA Receptor Subunits Are Necessary for Tonic Inhibition in the Hippocampus?," *J Neurosci* 28(6):1421-1426, Society for Neuroscience, United States (2008).
Guerrini, G., and Ciciani, G., "Benzodiazepine receptor ligands: a patent review (2006-2012)," *Expert Opin. Ther. Patents* 23(7):843-866, Informa UK, Ltd., United Kingdom (2013).
Guidotti, A., et al., "GABAergic dysfunction in schizophrenia: new treatment strategies on the horizon," *Psychopharmacology* 180:191-205, Springer-Verlag, Germany (2005).
Gupta, V., et al., "Pyrazoloquinoline-5-Ureas as negative modulators of $GABA_A$ α5" Division of Medicinal Chemistry Scientific Abstracts for the 241st National ACS Meeting and Exposition, Mar.

(56) References Cited

OTHER PUBLICATIONS 27-31, 2011, Anaheim, CA, MEDI 17, available at: https://www.yumpu.com/en/document/read/6571316/abstract-title-page-anaheim-2011-acs-division-ofmedicinal-.

Hauser, J., et al., "Hippocampal α5 subunit-containing GABA$_A$ receptors modulate the expression of prepulse inhibition," *Mol Psychiatry* 10:201-207, Nature Publishing Group, Germany (2005).

Higashino, M., et al., "Lead optimization of GABAA α5 receptor negative allosteric modulators," XXIV International Symposium on Medicinal Chemistry, Manchester, UK, Aug. 29, 2016, Abstract P280.

Hipp, J.F., et al., "Basmisanil, a highly selective GABA$_A$ α5 negative allosteric modulator: preclinical pharmacology and demonstration of functional target engagement in man," 19th biennial IPEG Meeting, Nijmegen, The Netherlands, Oct. 26-30, 2016, *Neuropsychiatric Electrophysiology* 2(Suppl 1):A20, Biomed Central, United Kingdom (2016).

International Search Report and Written Opinion for International Application No. PCT/IB2019/058208, European Patent Office, Netherlands, mailed Nov. 11, 2009 7 pages.

Kawaharada, S., et al., "ONO-8590580, a Novel GABA$_A$ α5 Negative Allosteric Modulator Enhances Long-Term Potentiation and Improves Cognitive Deficits in Preclinical Models," *J Pharm Exp Ther* 366:58-65, The American Society for Pharmacology and Experimental therapeutics, United States (2018).

Khundakar, A., et al., "Analysis of primary visual cortex in dementia with Lewy bodies indicates GABAergic involvement associated with recurrent complex visual hallucinations," *Acta Neuropathol Commun* 4:66, BioMed Central, United Kingdom (2016).

Knust, H., et al., "The discovery and unique pharmacological profile of RO4938581 and RO4882224 as potent and selective GABA$_A$ α5 inverse agonists for the treatment of cognitive dysfunction," *Bioorg Med Chem Lett*. 19:5940-5944, Elsevier, Netherlands (2009).

Koh, M., et al., "Selective GABA$_A$ α5 positive allosteric modulators improve cognitive function in aged rats with memory impairment," *Neuropharmacology* 64:145-152, Elsevier, Netherlands (2013).

Kwakowsky, A., et al., "GABA$_A$ receptor subunit expression changes in the human Alzheimer's disease hippocampus, subiculum, entorhinal cortex and superior temporal gyrus," *J Neurochem* 45:374-392, International Society for Neurochemistry, Canada (2018).

Lake, E., et al., "The effects of delayed reduction of tonic inhibition on ischemic lesion and sensorimotor function," *J Cereb Blood Flow Metab* 35:1601-1609, SAGE Publication, United Kingdom (2015).

Lu, C., et al., "Effects of Traumatic Stress Induced in the Juvenile Period on the Expression of Gamma-Aminobutyric Acid Receptor Type A Subunits in Adult Rat Brain," *Neural Plast* 2017(5715816):1-10, Hinadawi, United Kingdom (2017).

Martin, L.J., et al., "α5GABA$_A$ Receptor Activity Sets the Threshold for Long-Term Potentiation and Constrains Hippocampus-Dependent Memory," *J Neurosci* 30:5269-5282, Society for Neuroscience, United States(2010).

Martinez-Cue, C., et al., "Reducing GABAA α5 Receptor-Mediated Inhibition Rescues Functional and Neuromorphological Deficits in a Mouse Model of Down Syndrome," *J Neurosci* 33: 953-966, Society for Neuroscience, United States (213).

Maubach, K., "GABAA Receptor Subtype Selective Cognition Enhancers," *Curr Drug Targets CNS Neurol Disord* 2(4):233-239, Bentham Science Publisher, United Arab Emirates (2003).

Mendez, M.A., et al., "The brain GABA-benzodiazepine receptor alpha-5 subtype in autism spectrum disorder: a pilot [$^{11}$C]Ro15-4513 positron emission tomography study," *Neuropharmacology* 68:195-201, Elsevier, Netherlands (2013).

Mesbah-Oskui, L., et al., "Reduced expression of α5GABA$_A$ receptors elicits autism-like alterations in EEG patterns and sleep-wake behavior," *Neurotoxicol Teratol* 61:115-122, Elsevier, Netherlands (2017).

Mick, I., et al., "Evidence for GABA-A receptor dysregulation in gambling disorder: correlation with impulsivity," *Addict Biol* 22:1601-1609, John Wiley & Sons Ltd, United States (2016).

Mizuta, K., et al., "GABA$_A$ receptors are expressed and facilitate relaxation in airway smooth muscle," *Am J Physiol Lung Cell Mol Physiol* 294:L1206-1216, American Physiological Society, United States (2008).

Möhler, H., and Rudolph, U., "Disinhibition, an emerging pharmacology of learning and memory," *F1000 Research* 6(F1000 Faculty Rev):101, pp. 1-10, Taylor & Francis Group, United Kingdom (2000).

Möhler, H., "The legacy of the benzodiazepine receptor: from flumazenil to enhancing cognition in Down syndrome and social interaction in autism," Chapter One in *Adv Pharmacol* 72:1-36, Elsevier, Netherlands (2015).

Munro, G., et al., "A question of balance—positive versus negative allosteric modulation of GABA(A) receptor subtypes as a driver of analgesic efficacy in rat models of inflammatory and neuropathic pain," *Neuropharmacology* 61(1-2):121-132, Elsevier, Netherlands (2011).

Murley, A.G., and Rowe, J.B., "Neurotransmitter deficits from frontotemporal lobar degeneration," *Brain* 5:1263-1285, Oxford University Press, United Kingdom (2018).

Neugebauer, N.M., et al., "Hippocampal GABA$_A$ antagonism reverses the novel object recognition deficit in sub-chronic phencyclidine-treated rats," *Behav Brain Res* 342:11-18, Elsevier, Netherlands (2018).

Nutt, D.J., et al., "Blockade of alcohol's amnestic activity in humans by an α5 subtype benzodiazepine receptor inverse agonist," *Neuropharmacology* 53:810-820, Elsevier, Netherlands (2007).

Olsen, W. and Sieghart, W., "International Union of Pharmacology. LXX. Subtypes of γ-aminobutyric acid$_A$ receptors: classification on the basis of subunit composition, pharmacology, and function. Update," *Pharmacol Rev* 60(3):243-260, The American Society for Pharmacology and Experimental Therapies, United States (2008).

Otani, K., et al., "The GABA type A receptor alpha5 subunit gene is associated with bipolar I disorder," *Neurosci Lett* 381:108-113, Elsevier, Netherlands (2005).

Quirck, K., et al., "[3H]L-655,708, a novel ligand selective for the benzodiazepine site of GABAA receptors which contain the alpha 5 subunit," *Neuropharmacol* 35:1331-1335, Elsevier, Netherlands (1996).

Rautio, J., et al., "Prodrugs: design and clinical applications," *Nature Reviews—Drug Discovery* 7:255-270, Nature Publishing Group, Germany (2008).

Redrobe, J.P., et al., "Negative modulation of GABAA α5 receptors by RO4938581 attenuates discrete sub-chronic and early postnatal phencyclidine (PCP)-induced cognitive deficits in rats," *Psychopharmacology* 221: 451-468, SpringerLink, United States (2012).

Ribeiro, M.J. et al., "Abnormal relationship between GABA, neurophysiology and impulsive behavior in neurofibromatosis type 1," *Cortex* 64:194-208, Elsevier, Netherlands (2015).

Rudolph, U., and Knoflach, F., "Beyond classical benzodiazepines: novel therapeutic potential of GABAA receptor subtypes," *Nat Rev Drug Discov* 10:685-697, Macmillan Publishers, United States (2011).

Russo, L., et al., "A New Susceptibility Locus for Migraine with Aura in the 15q11-q13 Genomic Region Containing Three GABA-A Receptor Genes," *Am J Hum Genet* 76:327-333, The American Society of Human Genetics, United States (2005).

Savic, M.M., et al., "PWZ-029, a compound with moderate inverse agonist functional selectivity at GABA$_A$ receptors containing α5 subunits, improves passive, but not active, avoidance learning in rats," *Brain Res* 1208:150-159, Elsevier, Netherlands (2008).

Schipper, S., et al., "Tonic GABA$_A$ Receptors as Potential Target for the Treatment of Temporal Lobe Epilepsy," Mol. Neurobiol 53:5252-5265, Springer, United States (20160.

Sengupta, S., et al., "Could α5-GABA-A receptor activation be used as a target for managing medulloblastomas?," *CNS Oncol* 3:245-247, Future Medicine Ltd., United Kingdom (2014).

Sieghart, W., and Sperk, G., "Subunit composition, distribution and function of GABA(A) receptor subtypes," *Curr Top Med* 2:795-816, Bentham Science Publishers Ltd., United Arab Emirates (2002).

Soh, M., and Lynch, J.W., "Selective Modulators of α5-Containing GABAA Receptors and their Therapeutic Significance," *Curr Drug Targets* 16:735-746, (2015).

(56) References Cited

OTHER PUBLICATIONS

Solas, M., et al., "Treatment Options in Alzheimer's Disease: The GABA Story," *Curr Pharm Des* 21:4960-4971, Bentham Science Publishers Ltd., United Arab Emirates (2015).

Stefano, N., and Giorgio, N., "GABA: a new imaging biomarker of neurodegeneration in multiple sclerosis?," *Brain* 138:2467-2468, Oxford university Press, United Kingdom (2015).

Stephens, D. N., et al., "Role of GABAA alpha5-containing receptors in ethanol reward: the effects of targeted gene deletion, and a selective inverse agonist," *Eur J Pharmacol* 526:240-250, Elsevier, Netherlands (2005).

Sur, C., et al., "Autoradiographic localization of $\alpha 5$ subunit-containing $GABA_A$ receptors in rat brain," *Brain Res* 822:265-270, Elsevier Science B.V., Netherlands (1999).

Toso, L., et al., "Prenatal alcohol exposure alters GABAA$\alpha 5$ expression: A mechanism of alcohol-induced learning dysfunction," *Am J Obstet Gynecol* 195: 522-527, Elsevier, Netherlands (2006).

Wandel, C., et al., "RG1662, a new negative allosteric modulator of the gamma-aminobutyric acid A$\alpha 5$ receptor subtype, does not show convulsions at relevant doses," *Eur Neuropsychopharmacol* 25(Suppl2):S259, Elsevier, Netherlands (2015).

Wang, D-S., et al., "Memory deficits induced by inflammation are regulated by $\alpha 5$-subunit-containing $GABA_A$ receptors." *Cell Rep* 2:488-496, Cell Press, United States (2012).

Wearne, T.A., et al., "GABAergic mRNA expression is differentially expressed across the prelimbic and orbitofrontal cortices of rats sensitized to methamphetamine: Relevance to psychosis," *Neuropharmacology* 111:107-118, Elsevier, Netherlands (2016).

Whiting, P.J. et al., "GABA-A receptor subtypes in the brain: a paradigm for CNS drug discovery?," *Drug Discov Today* 8:445-450, Elsevier Science Ltd., Netherlands (2003).

Wisden, W., et al., "The distribution of 13 GABAA receptor subunit mRNAs in the rat brain. I. Telencephalon, diencephalon, mesencephalon" *J Neurosci* 12(3):1040-1062, Society for Neuroscience, United States (1992).

Wu, Z., et al., "Tonic inhibition in dentate gyrus impairs long-term potentiation and memory in an Alzheimer's disease model," *Nat Commun* 5(4159):1-13, Macmillan Publishers Limited, United States (2014).

Xiao, H-S., et al., "Identification of gene expression profile of dorsal root ganglion in the rat peripheral axotomy model of neuropathic pain" *PNAS* 99(12):8360-8365, United States National Academy of Sciences, United States (2002).

BICYCLIC DERIVATIVES AS GABAA A5 RECEPTOR MODULATORS

THE FIELD OF THE INVENTION

The present invention provides compounds of formula (I) having affinity and selectivity for the gamma-aminobutyric acid A receptor subunit alpha 5 (GABA$_A$ α5) and act as GABA$_A$ α5 negative allosteric modulators (GABA$_A$ α5 NAM), thereby useful in the treatment or prevention of diseases related to the GABA$_A$ α5 receptor, process for the preparation thereof, pharmaceutical compositions comprising them and their use as medicaments.

THE BACKGROUND OF THE INVENTION

Gamma-aminobutyric acid (GABA) is the major inhibitory neurotransmitter in the central nervous system. Receptors sensitive for GABA are divided into two main families, the ligand gated GABA$_A$ receptors and the G-protein coupled GABA$_B$ receptors.

The ligand gated GABA$_A$ receptor mediates the majority of inhibitory neurotransmission in the mammalian brain. The receptor is composed by the pentameric assembly of multiple subunits (α1-6, β1-3, γ1-3, δ, ε, π, θ, ρ1-3) (Olsen and Sieghart, *Pharmacol Rev* 2008, 60:243-260) forming a ligand-gated Cl$^-$-channel. Subunit distribution varies developmentally and regionally in the brain. This high variability leads to broad variation in inhibitory neural mechanisms and provides the possibility for specific therapeutic interventions (Fritschy and Möhler, *J Comp Neurol* 1995, 359:154-194). Physiological roles and pharmacological profiles of GABA$_A$ receptors are strongly dependent on the subunit constitution. Studies on genetically modified mice have demonstrated that receptor subunit composition, especially regarding the α subtypes, considerably determines pharmacology of compounds acting on the benzodiazepine-sensitive allosteric modulatory site (BDZ-site) (Rudolph and Knoflach, *Nat Rev Drug Discov* 2011, 10:685-697). The widely distributed α1-containing receptors mediate the sedative and amnesic effects, whereas the α2- and α3-containing receptors account for the anxiolytic, anticonvulsant and myorelaxant effects (Sieghart and Sperk, *Curr Top Med Chem* 2002, 2:795-816; Whiting et al, *Drug Discov Today* 2003, 8:445-450). α5 subunit containing receptors (α5GABA$_A$Rs) are preferentially expressed in the hippocampus in both rodents and primates and thought to be implicated in cognitive functions (Wisden et al, *J Neurosci* 1992, 12:1040-1062; Quirck et al, *Neuropharmacol* 1996, 35:1331-1335; Sur et al., *Brain Res* 1999, 822:265-270).

These α5-containing receptors are predominantly extra-synaptic and mediate tonic inhibition (Caraiscos et al., *Proc Natl Acad Sci USA* 2004, 101:3662-3667). Their inhibitory effect on the excitability of hippocampal and cortical principal neurons can explain the significant effect of α5GABA$_A$Rs in cognition, learning and memory and their potential therapeutic usefulness in various disorders including stroke, cognitive impairment, schizophrenia, dementia-related conditions or diseases related to impaired social cognition (Soh and Lynch, *Curr Drug Targets* 2015, 16:735-746).

Early modulators acting on the BDZ-site were non-selective compounds, either GABA enhancers with anxiolytic, sedative, anaesthetic or anticonvulsant potency or partial blockers, alternatively termed as inverse agonists or negative allosteric modulators (NAMs), with cognitive enhancing effects. GABA$_A$ receptor agonists and potentiators have been characterized as effective drugs in the clinical practice (Foster and Kemp, *Curr Opin Pharmacol* 2006, 6:7-17), while NAMs have so far only been tested in animal behavior experiments and in a very few human studies (Soh and Lynch, *Curr Drug Targets* 2015; 16:735-746). The results showed beneficial activity, however, drugs non-selectively acting on many GABA$_A$ receptor subtypes resulted in undesired CNS side effects like sedation, amnesia, drug abuse, anxiety, agitation or convulsions. Thus GABA research tended to design new drugs that selectively target specific GABA$_A$ receptor subtypes among them the α5GABA$_A$Rs (Möhler, *Adv Pharmacol* 2015, 72:1-36).

Depletion of the α5 subunit revealed the role of the α5-containing receptors in neuronal plasticity (Martin et al., *J Neurosci* 2010, 30:5269-5282) and high frequency neuronal network oscillations (Glykis et al., *J Neurosci* 2008 28:1421-1426), processes fundamentally involved in attention, information processing and memory. Genetic or pharmacological reduction of the α5 subunit function resulted in significant improvement of cognitive performance in rodent models (Möhler and Rudolph, *F1000Research*, 2017 6[F1000 Faculty Rev]:101). Both in vitro and in vivo experiments showed that negative allosteric modulation of the GABA$_A$ α5 is a promising strategy in the treatment or prevention of various pathological conditions or symptoms thereof. Selective inverse agonists of α5GABA$_A$Rs, namely NGD 97-1 (Bednar et al., *Clin Pharmacol Ther* 75, 2004 75:P30), α5IA (WO 02/06285 A1; Dawson et al., *J Pharmacol Exp Ther* 2006, 316:1335-1345; Braudeau et al., *J Psychopharmacol* 2011, 25:1030-1042), L-655,708 (Quirck et al, *Neuropharmacol* 1996, 35:1331-1335; Atack et al., *Neuropharmacology* 2006, 51:1023-102), α5IA-II (WO 98/50385 A1; Collinson et al., *Psychopharmacology* 2006; 188:619-628), MRK-016 (WO 99/67245 A1; Atack et al., *J Pharmacol Exp Ther.* 2009, 331:470-484), HT-2678 (Gupta et al., 241$^{st}$ ACS National Meeting, Anaheim, CA, Mar. 27-31, 2011, MEDI 17), PWZ-029 (WO 2007/018660 A2; Savic et al., *Brain Res* 2008; 1208:150-159; Biawat, Thesis at The University of Wisconsin-Milwaukee, August 2014), TB-21007 (Chambers et al., *J Med Chem* 2003, 46:2227-2240), ONO-8590580 (Higashino et al., *XXIV International Symposium on Medicinal Chemistry*, Manchester, UK—Aug. 29, 2016, Abstract P280; Kawaharada et al., *J Pharm Exp Ther* 2018, 366:58-65), R04938581 (Ballard et al., *Psychopharmacology* 2009, 202(1-3):207-223), R04882224 (Knust et al., *Bioorg Med Chem Lett.* 2009, 19:5940-5944), basmisanil (WO 2009/071476 A1; WO 2012/059482 A1; Hipp et al., *Neuropsychiatric Electrophysiology* 2016, 2(Suppl 1):A20) and the selective α5GABA$_A$R competitive blocker S44819 (Gacsályi et al., *Neuropharmacology* 2017, 125:30-38) as expected, proved to be effective in alleviating cognitive impairment in preclinical studies without possessing anxiogenic, proconvulsant or motor side effects. Cognitive improving effect of α5IA was demonstrated in healthy volunteers in an early pilot study (Nutt el al., *Neuropharmacology* 2007, 53:810-820). In addition, basmisanil (coded as RG1662 or RO5186582), the α5-selective compound under clinical development in schizophrenia-associated cognitive impairment (NCT02953639), resulted in significant increase in high frequency gamma oscillations in EEG activity in Down syndrome patients indicating a potential facilitatory effect on cognitive functions (Bolognani et al., *67th Annu Meet Am Acad Neurol* Washington, DC, Apr. 23, 2015, Abst P6.273). No CNS side effects of the clinically tested α5 blockers α5IA, S44819 or basmisanil has been reported so far (Atack et al., *Pharmacol Therap* 2010, 125:11-26; Darmani et al., *J Neurosci* 2016, 36:12312-

12320; Wandel et al., *Eur Neuropsychopharmacol* 2015 25(Suppl2):S259). On the base of preclinical data and clinical findings a favorable clinical profile of α5-subunit selective negative modulators can be predicted.

After all, due to the specific function and the compartmentalized CNS expression profile of α5GABA$_A$Rs, selective and gentle intervention, that negatively modulate its function, may have therapeutic benefit compared to non-selective agents.

Therefore, compounds having high affinity and selectivity for the α5GABA$_A$Rs, GABA$_A$ α5 NAMs respectively, can be used, alone or in combination with one or more other active ingredients, for the treatment or prevention of disorders of the central nervous system where one of the symptoms and/or syndromes of the disease may be related to the GABA$_A$ α5 receptor. These include, but not limited to neurocognitive disorders (Collinson et al., *J Neurosci* 2002, 22:5572-5580) such as Alzheimer's disease (AD) (Kwakowsky et al., *J Neurochem* 2018, 145:374-392; Solas et al., *Curr Pharm Des* 2015; 21:4960-4971; Wu et al., *Nat Commun* 2014, 4159), prodromal AD and mild cognitive impairment (Maubach, *Curr Drug Targets* CNS Neurol Disord 2003, 2:233-239), vascular cognitive impairment and vascular dementia (Gacsályi et al., *Eur J Pharmacol* 2018, 834:118-125), frontotemporal lobar degeneration including frontotemporal dementia, progressive supranuclear palsy and corticobasal syndrome (Murley and Rowe, *Brain* 2018, 5:1263-1285), Lewy body dementia (Khundakar et al., *Acta Neuropathol Commun* 2016, 4:66), age-associated memory impairment and cognitive decline (Koh et al., *Neuropharmacology* 2013, 64:142-152), cognitive impairment associated with brain cancers including but not limited to medulloblastomas (Sengupta et al., *CNS Oncol* 2014, 3:245-247), post-operative dementia (Cheng et al., *J Neurosci* 2006, 26:3713-3720), inflammation-induced dementia (Wang et al., *Cell Rep* 2012, 2: 488-496), cognitive impairments associated with the diseases including but not limited to migraine and tension headache (Russo et al., *Am J Hum Genet* 2005, 76:327-333), multiple sclerosis (Stefano and Giorgio, *Brain* 2015, 138:2467-2468), Parkinson's disease (Blaszczyk, *Front Neurosci* 2016, 10:269-277), epilepsy (Schipper et al., *Mol Neurobiol* 2016, 53:5252-5265), attention deficit hyperactivity disorder and adult attention deficiency (Bollmann et al., *Transl Psychiatry* 2015, 8:e589; Edden et al., *Arch Gen Psychiatry* 2014, 69:750-753) or other CNS diseases including, but not limited to, post-traumatic stress disorder (Lu et al., *Neuronal Plast* 2017, 2017:5715816), schizophrenia (Guidotti et al., *Psychopharmacology* 2005, 180:191-205), positive, negative and/or cognitive symptoms associated with schizophrenia (Asai et al., *Schizophrenia Res* 2008, 99:333-340; Gill et al., *Neuropsychopharmacology* 2011, 36:1903-1911; Hauser et al., *Mol Psychiatry* 2005, 10:201-207; Redrobe et al., Psychopharmacology 2012, 221: 451-468), bipolar disorders (Otani et al., *Neurosci Lett* 2005, 381:108-113), autism spectrum disorder (ASD) (Mendez et al., *Neuropharmacology* 2013, 68:195-201), fragile X disorder (Curia et al, *Cereb Cortex* 2009, 19:1515-1520), Prader-Willi syndrome (Bittel et al., *J Med Genet* 2003, 40:568-574), Down syndrome (Braudeau et al., *J Psychopharmacol* 2011, 25:1030-1042; Martinez-Cue et al., *J Neurosci* 2013, 33: 953-966), Huntington's disease (Du et al., *Front Mol Neurosci.* 2017, 10:198), neurofibromatosis type I (Ribeiro et al., *Cortex* 2015, 64:194-208), sleep disorders (Mesbah-Oskui et al., *Neurotoxicol Teratol* 2017, 61:115-122), alcoholism (Stephens et al., *Eur J Pharmacol* 2005, 526:240-250), fetal alcohol syndrome (Toso et al., *Am J Obstet Gynecol* 2006, 195:522-527), mood disorders (Carreno et al., *Int J Neuropsychopharmacol* 2017, 20:504-509; Choudary et al., *Proc Nat!Acad Sci USA* 2005, 102:15653-15658; Fischell et al., *Neuropsychopharmacology* 2015; 40:2499-2509), psychotic disorders (Wearne et al., *Neuropharmacology* 2016, 111: 107-118), substance-induced psychotic disorder (Neugebauer et al., *Behav Brain Res* 2018, 342:11-18), anxiety disorders (Behlke et al., *Neuropsychopharmacology* 2016, 41:2492-2501; Botta et al., *Nat Neuroscience* 2015, 18:1493-1500), fear related disorders (Botta et al., *Nat Neuroscience* 2015, 18:1493-1500; Crestani et al., *Proc Natl Acad Sci USA* 2002, 99:8980-8985), stress disorder (Fischell et al., *Neuropsychopharmacology* 2015; 40:2499-2509), behavioural or drug addictions (Mick et al., *Addict Biol* 2017, 22:1601-1609), stroke (Clarkson et al., *Nature* 2010, 468:305-309; Lake et al., *J Cereb Blood Flow Metab* 2015, 35:1601-1609), neuropathic pain (Xiao et al., *Proc Natl Acad Sci USA* 2002, 99:8360-8365) and inflammatory pain (Bravo-HernAndez et al., *Eur J Pharmacol.* 2014, 734:91-97; Munro et al., Neuropharmacology 2011, 61:121-132). Modulating α5GABA$_A$Rs may also be beneficial in treating diseases and conditions including, but not limited to bronchoconstrictive diseases such as but not limited to asthma, chronic obstructive pulmonary disease, and bronchopulmonary dysplasia (Gallos et al., *Am J Physiol Lung Cell Mol Physiol* 2015, 308:L931-942; Mizuta et al., *Am J Physiol Lung Cell Mol Physiol* 2008, 294:L1206-1216). Compounds capable of modulating α5GABA$_A$Rs are in particular expected to be useful candidates for the treatment of neurocognitive disorders, Alzheimer's disease, and schizophrenia.

Numerous structurally different compounds active on the α5 subunit of the GABA$_A$ receptor are known in the art (Guerrini et al., *Expert Opin Ther Patents* 2013, 23(7):843-866), including isoxazole (e.g. WO 2009/071464 A1, WO 2009/071477 A1, WO 2010/097368 A1, WO 2010/112475 A1, WO 2010/127978 A1) and triazole derivatives (e.g. WO 2012/062687 A1, WO 2014/001281 A1).

Certain isoxazole and triazole derivatives as agonists of the NR1H4 (farnesoid X or FXR) receptor are described in e.g. WO 2017/133521 A1, WO 2013/007387 A1, WO 2008/157270 A1 or WO 2007/140174 A2. Furthermore, tetrahydroisoquinoline derivatives as LXR (liver X receptor) modulators are disclosed in e.g. WO 2007/047991 A1.

Despite the numerous studies and modulators of the GABA$_A$ α5 receptor, unmet need still persists to provide compounds that can be useful in the treatment or prevention of diseases related to the GABA$_A$ α5 receptor.

SUMMARY OF THE INVENTION

The present invention provides the compounds of formula (I)

wherein
A is represented by

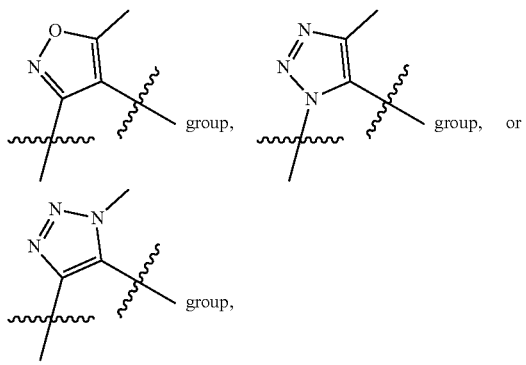

$R^1$ is hydrogen or halogen,
n and m are each independently 1 or 2,
$R^2$ is hydrogen; $C_{1-4}$alkyl optionally and independently substituted with one ore more halogen, $C_{1-4}$alkoxy, —S(O)$_2$—$C_{1-4}$alkyl, or with $R^3$; NR$^4$R$^5$ or R$^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^3$, $R^6$ and $R^7$ is optionally substituted carbocycle, heterocycle or heteroaryl
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

The present invention provides a compound of formula (I), as defined above for use in the treatment or prevention of diseases related to the GABA$_A$ α5 receptor.

The present invention provides the use of a compound of formula (I), as defined above, for the manufacture of a medicament for the treatment or prevention of diseases related to the GABA$_A$ α5 receptor.

The present invention provides a method of treating or preventing diseases related to the GABA$_A$α5 receptor comprising administering to a subject, including humans, in need of such treatment or prevention an effective amount of at least one compound of formula (I), as defined above.

The present invention provides the combinational use of compounds of formula (I) as defined above, with one or more other active ingredients for the treatment or prevention of diseases related to the GABA$_A$ α5 receptor.

The present invention provides pharmaceutical compositions containing the compound of formula (I), as defined above as active ingredients.

The present invention provides medicaments (combinational pharmaceutical compositions) comprising a combination of the compound of formula (I), as defined above with one or more other active ingredients.

The present invention provides pharmaceutical compositions containing the compound of formula (I), as defined above as active ingredients alone or in combination with one ore more other active ingredients for use in the treatment or prevention of diseases related to the GABA$_A$ α5 receptor.

The present invention provides a process for the manufacture of the compounds of formula (I), as defined above.

The present invention also provides a chemical or pharmaceutical preparation of pharmaceutical compositions containing the compounds of formula (I), as defined above alone, or in combination with one ore more other active ingredients.

DETAILED DESCRIPTION OF THE INVENTION

The present invention provides compounds of formula (I) having affinity and selectivity for the alpha 5 subunit-containing gamma-aminobutyric acid A receptor (GABA$_A$ α5 receptor) and act as GABA$_A$ α5 receptor negative allosteric modulators, thereby useful in the treatment or prevention of diseases related to the GABA$_A$ α5 receptor, process for the preparation thereof, pharmaceutical compositions comprising them alone or in combination with one or more other active ingredients and their use as medicaments.

The present invention relates to compounds of formula (I)

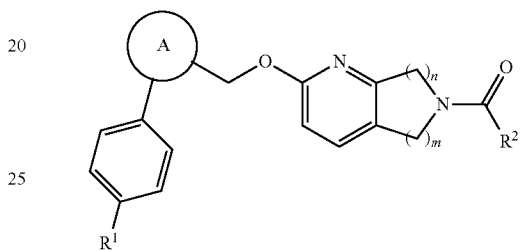

wherein
A is represented by

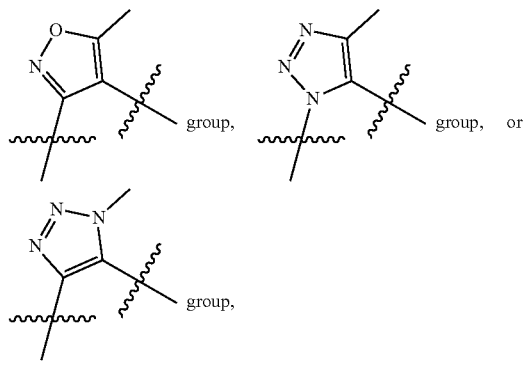

$R^1$ is hydrogen or halogen,
n and m are each independently 1 or 2,
$R^2$ is hydrogen; $C_{1-4}$alkyl optionally and independently substituted with one ore more halogen, $C_{1-4}$alkoxy, —S(O)$_2$—$C_{1-4}$alkyl, or with $R^3$; NR$^4$R$^5$ or R$^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^3$, $R^6$ and $R^7$ is optionally substituted carbocycle, heterocycle or heteroaryl
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

Unless otherwise defined, all technical and scientific terms used herein have the same meaning as commonly understood by one of ordinary skill in the art to which this invention belongs.

Although methods and materials similar or equivalent to those described herein can be used in the practice or testing of the invention, suitable methods and materials are described below.

The nomenclature used is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

Definition of the general terms used herein, whether or not the terms in question are presented individually or in combination with other groups are described below.

"Optional" or "optionally" means that the subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents.

When indicating the number of substituents, the term "one or more" refers to the range from one substituent to the highest possible number of substitution, i.e. replacement of one hydrogen up to replacement of all hydrogens by substituents. One, two or three substituents on a given atom, especially on a carbon atom are preferred.

Where any group may carry multiple substituents and a variety of possible substituents is provided, the substituents are independently selected and need not to be the same.

The term "unsubstituted" means that the specified group bears no substituents.

The term "optionally substituted" means that any atom of the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. The possible substituents include, but are not limited to, $C_{1-4}$alkyl, $C_{1-4}$alkoxy, halogen, halo$C_{1-4}$alkyl, halo$C_{1-4}$alkoxy, hydroxyl, oxo and the like.

The term "$C_{1-4}$alkyl" refers alone or in combination with other groups to a straight or branched, single or multiple branched, hydrocarbon radical and consists of 1 to 4 carbon atoms. Examples include, but are not limited to, methyl, ethyl, propyl, i-propyl (isopropyl), n-butyl, 2-butyl (sec-butyl) or t-butyl (tert-butyl) group. Preferred alkyl group is $C_{1-3}$alkyl.

The term "$C_{1-4}$alkoxy" refers alone or in combination with other groups to —O—$C_{1-4}$alkyl group, wherein the $C_{1-4}$alkyl is as defined above. Examples include, but are not limited to, methoxy, ethoxy, i-propoxy, n-propoxy or t-butoxy. Preferred alkoxy group is $C_{1-3}$alkoxy.

The term "—S(O)$_2$—$C_{1-4}$alkyl" refers alone or in combination with other groups to $C_{1-4}$alkyl group substituted with —S(O)$_2$— wherein $C_{1-4}$alkyl is as defined above. Examples include, but are not limited to, methyl sulfonyl, ethyl sulfonyl, i-propyl sulfonyl, n-propyl sulfonyl, sec-butyl sulfonyl or t-butyl sulfonyl. Preferred sulfonyl group is —S(O)$_2$—$C_{1-3}$alkyl.

The term "halogen", "halo" or "halide" refers alone or in combination with other groups to fluoro (fluorine), chloro (chlorine), bromo (bromine) or iodo (iodine), preferably fluoro (fluorine), chloro (chlorine) or bromo (bromine). Preferred halogen is fluorine and chlorine.

The term "halo$C_{1-4}$alkyl" refers alone or in combination with other groups to a $C_{1-4}$alkyl as defined above substituted with one or more identical or different halogens on any carbon atoms of said $C_{1-4}$alkyl, including vicinal and germinal halo-substitutions as well. The term "perhaloalkyl" refers to a $C_{1-4}$alkyl where all hydrogen atoms have been replaced by the same or different halogen atoms. Examples include, but are not limited to, monohalo-, dihalo-ortrihalo-methyl, -ethyl or -propyl, for example 3,3,3-trifluoropropyl, 2-fluoroethyl, 2,2,2-trifluoroethyl, fluoromethyl, or trifluoromethyl. Preferred haloalkyl group is halo$C_{1-3}$alkyl.

The term "carbocycle" refers alone or in combination with other groups to a monovalent monocyclic or bicyclic, fused or bridged, saturated, mono-, or bi-unsaturated, or aromatic ring system comprising 3 to 14 carbon ring atoms. The term "cycloalkyl" refers to monovalent monocyclic or bicyclic, fused or bridged, saturated carbocyclic groups comprising 3 to 10 carbon ring atoms. Examples include cyclopropane, cyclobutane, cyclopentane, cyclohexane, cycloheptane, cyclooctane, bicyclo[2.2.1]heptane, bicyclo [2.2.2]octane or adamantane and the like. Preferred cycloalkyl is monocyclic. Preferred monocyclic cycloalkyl is 3- to 6-membered. The term "cycloalkenyl" refers to monovalent monocyclic or bicyclic, fused or bridged, mono-, or bi-unsaturated carbocyclic groups comprising 3 to 10 carbon ring atoms. Examples include cyclobutene, cyclopentene, cyclopentadiene, cyclohexene, cyclohexadiene, cycloheptene, decaline and the like. Preferred cycloalkenyl is monocyclic. Preferred monocyclic cycloalkenyl is 4- to 6-membered. The term "aryl" refers to monovalent, mono- or bicyclic aromatic carbocyclic groups comprising 6 to 14 carbon ring atoms. Bicyclic aryl groups comprise at least one aromatic carbocyclic group. Examples include phenyl, dihydro-indene, indene, naphthyl, dialin, tetralin, anthryl, azulenyl, indanyl and the like. Preferred aryl is 6- to 10-membered. Preferred aryl is monocyclic. Preferred monocyclic aryl is phenyl.

The term "heterocycle" refers alone or in combination with other groups to a monovalent saturated or partly unsaturated monocyclic, bicyclic, fused, bridged or spiro ring system of 3 to 10 ring atoms comprising 1, 2, 3 or 4 ring heteroatoms independently selected from N, O and S, the remaining ring atoms being carbon. Preferred heterocycle is monocyclic. Examples for monocyclic heterocycles are aziridine, 2H-azirine, oxirane, thiirane, azetidine, oxetane, thietane, azetidine-2-one, pyrrolidine, pyrrolidinone, pyrroline, pyrazolidine, imidazoline, pyrazoline, tetrahydrofuran, dihydrofuran, dioxolane, tetrahydrothiophene, oxazolidine, dihydro-oxazole, isoxazolidine, oxathiolane, sulfolane, thiazolidine, thiazolidinedione, succinimid, oxazolidone, hydantoin, piperidine, piperidinone, piperazine, tetrahydropyran, tetrahydrothiopyrane, dihydropyrane, tetrahydropyridine, dioxane, thiane, dithiane, 1,1-dioxo-thiane, morpholine, thiomorpholine, 1,1-dioxo-thiomorpholin, azepane, diazepane, homopiperazine, oxazepnayl and the like. Preferred monocyclic hetercycle is 4- to 6-membered. Preferred monocyclic hetercycle is saturated. Examples for bicyclic, fused, bridged or spiro heterocycles are pyrrolizidine, dihydropyrrolopyrrole, tetrahydropyrrolopyrrole, furopyrrole, thinopyrrole, indoline, indole, isoindole, benzoisothiazolone, decahydroisoquinoline, decahydroquinoline, tetrahydroquinoline, dihydroquinoline, dihydroisoquinoline, chromene, isochromene, benzoxazine, quinuclidine, azaadamantane, spiro[cyclobutane-1,3'-indole], 1-oxaspiro[4.5]decane, 1,6-oxaspiro[3.4]octane, 8-aza-bicyclo[3.2.1]octane, 8-oxa-3-aza-bicyclo[3.2.1]octane, tetrahydro-spiro[isobenzofuran-1,2'-pyran], 1-oxaspiro[4.4]nonane-2-one, 2-oxa-7-azaspiro[3.5]nonane, 1,4-dioxa-7-azaspiro[4.4]nonane, 1,3-diazaspiro[4.4]non-2-en-4-one, 9-aza-bicyclo[3.3.1]nonane, 3-oxa-9-azabicyclo[3.3.1]nonane, 3-thia-9-aza-bicyclo [3.3.1]nonane, 1,4-dithia-7-azaspiro[4.4]nonane, 8-azaspiro [4.5]decane-7,9-dione, 1,3,8-triazaspiro[4.5]decane-4-one and the like.

The term "heteroaryl" refers alone or in combination with other groups to a monovalent, heterocyclic aromatic, mono- or bicyclic ring system of 5 to 12 ring atoms, comprising 1, 2, 3 or 4 heteroatoms independently selected from N, O and S, the remaining ring atoms being carbon. The bicyclic heteroaryl group comprises at least one aromatic ring. Examples for heteroaryl are pyrrole, furan, thiophene, imidazole, oxazole, isoxazole, thiazole, isothiazole, triazole, tetrazole, oxadiazole, thiadiazole, tetrazole, pyridine, pyrazine, pyrazole, pyridazine, pyrimidine, triazine, azepine, diazepine, benzofuran, benzothiophene, indole, isoindole, isobenzofuran, benzimidazole, benzoxazole, benzoisoxazole, benzothiazole, benzoisothiazole, benzooxadiazole, benzothiadiazole, benzotriazole, purin, quinoline, isoquinoline, quinazoline, quinoxaline, carbazole, or acridine. Prefered heteroaryl is 5 to 10 membered. Prefered heteroaryl is monocyclic. Prefered monocyclic heteroaryl is 5- or 6-membered.

The terms "compound(s) of this invention", "compound(s) of the present invention" or "compounds of formula (I), as defined above" refers to compounds of formula (I) and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof. Moreover, any combination of the embodiments of A, $R^1$-$R^7$, n and m as defined hereinafter are preferred groups of compounds of formula (I).

The term "salt" refers to pharmaceutically acceptable and/or to pharmaceutically non-acceptable salts.

The term "pharmaceutically acceptable salt" refers to a conventional acid addition or base addition salt which preserves the biological efficacy and properties of the compounds of formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide. These salts often exhibit more favorable solubility properties than the compounds used for their preparation and are therefore more suitable for use in the preparation of various pharmaceutical formulations.

The "pharmaceutically non-acceptable salts" may be preferred for the purification or isolation of the compounds of formula (I) and are therefore also within the scope of the invention.

The term "prodrug" refers to derivatives of compounds of formula (I) according to the invention which themselves have no therapeutic effect but containing such groups which, after in vivo chemical or metabolic degradation (biotransformation) become "biologically active metabolite" which is responsible for the therapeutic effect. Such decomposing groups associated with the compounds of formula (I) of the present invention, in particular those suitable for prodrugs, are known in the art and may also be applied for the compounds of the present invention (Rautio et al., *Nature Reviews—Drug Discovery* 2008, 7:255-270).

The compounds of formula (I) may exist in various geometric isomeric forms. In addition, certain compounds of formula (I) may contain one or more asymmetric centers, thus exist in stereoisomeric and diastereomeric forms. The term "stereoisomer" denotes a compound that possesses identical molecular connectivity and bond multiplicity, but which differs in the arrangement of its atoms in space. All of these compounds, such as cis isomers, trans isomers, diastereomeric mixtures, racemates, non-racemic mixtures of enantiomers, substantially pure and pure enantiomers are within the scope of the invention. The substantially pure enantiomers contain up to 5 wt %, preferably 2 wt %, most preferably 1 wt %, of the corresponding opposite enantiomer.

Optical isomers can be prepared by resolving the racemic mixtures by known methods, for example, by using an optically active acid or base to form diastereoisomeric salts or by forming covalent diastereomers. Suitable acids include, for example, tartaric acid, diacetyltartaric acid, dibenzoyltartaric acid, ditoluoyltartaric acid and camphorsulfonic acid. Diastereoisomeric mixtures can be separated into individual diastereomers based on their physical and/or chemical differences, by methods known to those skilled in the art, such as chromatography or fractional crystallization. Subsequently, the optically active bases or acids are liberated from the separated diastereoisomeric salts. Various methods of separating optical isomers include chiral chromatography (e.g., chiral HPLC columns) optionally used by derivatization with the aim to maximize the separation of enantiomers. Appropriate chiral HPLC columns are Diacel columns, such as CHIRALPAK or CHIRALCEL columns, which can be routinely chosen as desired. Where applicable, enzymatic separations carried out by derivatization may also be used. The optically active compounds of formula (I) can also be prepared using optically active starting materials using chiral synthesis without racemization reaction conditions.

The compounds of formula (I) may exist in various polymorphic forms. As is known in the art, polymorphism is the ability of a compound to crystallize in more than one crystalline form, i.e. in polymorphic form. Polymorphic forms of a particular compound can be defined by identical chemical formula or composition and differ in their chemical structure as crystalline structures of two different chemical compounds.

The compounds of formula (I) and salts thereof may also be present as solvates or hydrates, which are also within the scope of the invention. The term "solvate" refers to non-covalent stoichiometric or nonstoichiometric combinations of solvent and solute. The term "hydrate" refers to non-covalent stoichiometric or nonstoichiometric combinations of water and solute.

The present invention provides pharmaceutical compositions comprising at least one compound of formula (I), as defined above as active ingredient.

The present invention provides pharmaceutical compositions comprising a combination of the compound of formula (I), as defined above with one or more other active ingredients. The pharmaceutical composition may comprise at least one compound of the invention together with one ore more other active ingredients in a single dosage form or separately. The combinational composition may be administered simultaneously, separately or sequentially.

The term "pharmaceutical composition" (or "composition") refers to a mixture or solution comprising a therapeutically effective amount of an active ingredient together with pharmaceutically acceptable excipients to be administered to a subject, e.g., a human in need thereof.

The present invention also relates to the chemical and pharmaceutical preparation of pharmaceutical compositions.

The pharmaceutical compositions of the present invention may be formulated in various pharmaceutical formulations, such as, but not limited to, solid oral dosage forms such as tablets (e.g., buccal, sublingual, effervescent, chewable, orally dispersible), capsules, pills, pilulas, orally dispersible films, granules, powders; liquid formulations such as solutions, emulsions, suspensions, syrups, elixirs, drops; parenteral dosage forms such as intravenous injections, intramuscular injections, subcutaneous injections; other forms of medicine such as eye drops, semi-solid ophthalmic preparations, semi-solid dermal preparations (such as ointments, creams, pastes), transdermal therapeutic systems, suppositories, rectal capsules, rectal solutions, emulsions and suspensions, etc.

The pharmaceutical compositions of the present invention may be administered in various ways, such as, but not limited to oral, rectal, mucous, transdermal or intestinal administration; parenteral administration including intramuscular, subcutaneous, intravenous, intramedullary injections as well as intraarticular, intrathecal, direct intraventricular, intraperitoneal, intranasal or intraocular injections and eye drops.

Alternatively, the compounds may be administered locally and not systemically, for example by direct injection of the compound to the kidney or the heart, often in a modified release formulation. In addition, the drug may be administered in a targeted carrier system, for example in a tissue-specific antibody encapsulated liposome. The liposomes transfer the active agent selectively to the target organ, which absorbs it.

The pharmaceutical composition may be administered in various ways and in various pharmaceutical forms. The compound of the invention may be administered alone or in combination with pharmaceutically acceptable excipients, in single or multiple doses. The dose required to achieve the appropriate therapeutic effect may vary widely and must always be adapted to individual needs with regard to the degree of disease, the condition and weight of the patient being treated and the sensitivity to the active ingredient, the way of dosage regimen and the numbers of daily treatments.

For simple administration, it is preferred that the pharmaceutical compositions consist of dosage units that contain the amount of active ingredient(s) to be administered once, or a small number of multiple, or half, one third, a quarter. Such dosage units are, for example, tablets that can be provided with a half or quarter groove to facilitate half or quarter-splitting of the tablet in order to weigh the required amount of active ingredient(s).

Pharmaceutical compositions containing the active ingredient(s) according to the invention generally contain from 0.01 to 500 mg of active ingredient(s) per dosage unit. It is of course also possible that the amount of active ingredient(s) in each formulation exceeds the above limit either up or down.

The present invention relates also to pharmaceutical compositions for use in pediatric use such as, but not limited to, solutions, syrups, elixirs, suspensions, powders for the preparation of suspensions, dispersible or effervescent tablets, chewable tablets, orodispersible tablets, tablets or coated tablets, orally sparkling powders or granules, capsules.

The pharmaceutical compositions of the present invention may be prepared by methods known per se such as conventional mixing, dissolution, emulsification, suspending, microencapsulation, freeze drying, extrusion and spheronization, lamination, film coating, granulation, encapsulation, drageage or pressing.

The pharmaceutical compositions of the present invention may be formulated in the usual way using one or more physiologically (or pharmaceutically) acceptable excipients which promote the incorporation of the active ingredient into pharmaceutically acceptable pharmaceutical forms. The term "physiologically or pharmaceutically acceptable excipient" denotes any ingredient used in formulating pharmaceutical products which have no therapeutic activity and non-toxic. The proper formulation depends on the mode of administration chosen. Any of the techniques and excipients well known in the art can be used.

The excipients applicable in the preparation may be selected from the following categories, such as, but not limited to, fillers of tablets and capsules, binders of tablets and capsules, modified drug release agents, disintegrants, glidants, lubricants, sweeteners, taste-masking agents, flavorants, coating materials, surfactants, stabilizers, preservatives or antioxidants, buffering agents, complexing agents, wetting or emulsifying agents, salts for adjusting the osmotic pressure, lyophilization excipients, microencapsulating agents, ointment materials, penetration enhancers, solubilizers, solvents, suppository materials, suspending agents. Suitable pharmaceutical excipients can be for example: starch, microcrystalline cellulose, talc, glucose, lactose, gelatin, silica, talc, magnesium stearate, sodium stearate, glycerol monostearate, cellulose derivatives, sodium chloride, glycerol, propylene glycol, water, ethanol and the like.

Another embodiment of the present invention relates to the use of special binders that can improve the solubility, dissolution, penetration, absorption or bioavailability of the active ingredient(s), such as, but not limited to, hydrophilic polymers, hot melting extruding excipients, surfactants, buffering agents, complexing agents, emulsifying agents, lyophilization excipients, disintegrants, microencapsulating agents, penetration promoters, solubilizers, cosolvents, suspending agents.

The excipients described above and the various methods of preparation are only representative examples. Other materials and process techniques known in the art may also be used.

The term "other active ingredient" refers to therapeutic agents including, but not limited to acetylcholinesterase inhibitors (such as galantamine, rivastigmine, donepezil, tacrine, phenserine, ladostigil and ABT-089); NMDA receptor agonists or antagonists (such as memantine, neramexane, EVT101, and AZD4282); anti-amyloid antibodies including anti-amyloid humanized monoclonal antibodies (such as bapineuzumab, ACCOOI, CAD 106, AZD3102, H12A11V1); beta- (such as verubecestat, and AZD3293) or gamma-secretase inhibitors (such as LY450139 and TAK 070) or modulators; tau phosphorylation inhibitors; ApoE4 conformation modulators; p25/CDK5 inhibitors; NK1/NK3 receptor antagonists; COX-2 inhibitors (such as celecoxib, rofecoxib, valdecoxib, 406381 and 644784); LRRK2 inhibitors; HMG-CoA reductase inhibitors; NSAIDs (such as ibuprofen); vitamin E; glycine transport inhibitors; glycine site antagonists (such as lacosamide); LXR β agonists; androgen receptor modulators; blockers of Aβ oligomer formation; NR2B antagonists, anti-inflammatory compounds (such as (R)-flurbiprofen, nitroflurbiprofen, ND-1251, VP-025, HT-0712, and EHT-202); PPAR gamma agonists (such as pioglitazone and rosiglitazone); CB-1 receptor antagonists or inverse agonists (such as AVE1625); CB-2 agonists (such as 842166 and SAB378); VR-1 antagonists (such as AMG517, 705498, 782443, PAC20030, VI 14380 and A425619); bradykinin BI receptor antagonists (such as SSR240612 and NVPSAA164); sodium channel blockers and antagonists (such as VX409 and SP1860); NOS inhibitors (such as SD6010 and 274150); antibiotics; growth hormone secretagogues (such as ibutamoren, ibutamoren mesylate, and capromorelin); potassium channel openers; AMPA agonists or AMPA modulators (such as CX-717, LY 451395, LY404187 and S-18986); GSK3 inhibitors (such as AZD1080, SAR502250 and CEP16805); neuronal α7 nAChR agonists or PAMs (such as ABT-126, AZD0328, EVP-6124, AVL-3288 or PNU-120596); MARK ligands; M1 or M4 mAChR agonists or PAMs; mGluR2 antagonists or NAMs or PAMs; mGluR5 antagonists (such as AZD9272); alpha agonists; ADAM-10 ligands; sedatives, hypnotics, anxiolytics, antipsychotics, cyclopyrrolones, imidazopyridines, pyrazolopyrimidines, minor tranquilizers, melatonin agonists and antagonists, melatonergic agents; orexin antagonists and agonists; prokineticin agonists and antagonists; T-type calcium channel antagonists; triazolopyridines benzodiazepines, barbiturates; 5-HT1A antagonists (such as lecozotan); 5-HT2 antagonists; 5-HT4 agonists (such as PRX-03140); 5-HT6 antagonists (such as GSK 742467, SGS-518, FK-962, SL-65.0155, SRA-333 and xaliproden); histamine H3 receptor antagonists and inverse agonists (such as S38093, ABT-834, ABT 829, GSK 189254 and CEP16795); PDE4 inhibitors (such as HT0712); PDE9 inhibitors (such as B140936); PDE10 inhibitors; HDAC inhibitors; KCNQ antagonists; $GABA_A$ signaling enhancers (such as L-838,417, TPA-023, alphaxalone, ganaxolone, gaboxadol, tiagabine, vigabatrine, bumetadine), and blockers (such as S44819), $GABA_B$ signalling enhancers (such as baclofen), V1a receptor antagonists (such as balovaptan); MAO-B inhibitors; dopamine transport inhibitors; noradrenaline transport inhibitors; D2 agonists and partial agonists; anticholinergics (such as biperiden); COMT inhibitors (such as entacapone); A2a adenosine receptor antagonists; cholinergic agonists; compounds from the phenothiazine, thioxanthene (such as chlorprothixene and thiothixene), heterocyclic dibenzazepine (such as clozapine), butyrophenone (such as haloperidol), diphenylbutylpiperidine (such as pimozide) and indolone (such as molindolone) classes of neuroleptic agents; loxapine, sulpiride; atypical antipsychotics (such as aripiprazole, asenapine, brexpiprazole, cariprazine, iloperidone, lurasidone, olanzapine, paliperidone, quetiapine, risperidone and ziprasidone); levodopa; calcium channel blockers (such as ziconotide and NMED160); MMP inhibitors: thrombolytic agents; opioid analgesics (such as codeine, fentanyl, hydromorphone, levorphanol, meperidine, methadone, morphine, oxycodone, oxymorphone, pentazocine, propoxyphene); pramipexole; ropinirole; neutrophil inhibitory factor; SSRIs or SSNRIs; tricyclic antidepressant drugs; norepinephrine modulators; lithium; valproate; gabapentin; pregabalin; rizatriptan; zolmitriptan; naratriptan and sumatriptan or other drugs that affect receptors or enzymes that either increase the efficacy, safety, convenience, or reduce unwanted side effects or toxicity of the compounds of the present invention.

In one embodiment, the other active ingredient refers to an acetylcholinesterase inhibitor (such as galantamine, rivastigmine, donepezil, tacrine, phenserine, ladostigil and ABT-089); NMDA receptor agonist or antagonist (such as memantine, neramexane, EVT101, and AZD4282); anti-amyloid antibody including anti-amyloid humanized monoclonal antibody (such as bapineuzumab, ACCOOI, CAD 106, AZD3102, H12A11V1); beta- (such as verubecestat, and AZD3293) or gamma-secretase inhibitor (such as LY450139 and TAK 070) or modulator; tau phosphorylation inhibitor; ApoE4 conformation modulator; glycine transport inhibitor; AMPA agonist or AMPA modulator (such as CX-717, LY 451395, LY404187 and S-18986); neuronal α7 nAChR agonist or PAM (such as ABT-126, AZD0328, EVP-6124, AVL-3288 or PNU-120596); 5-HT6 antagonist (such as GSK 742467, SGS-518, FK-962, SL-65.0155, SRA-333 and xaliproden); histamine H3 receptor antagonist and inverse agonist (such as S38093, ABT-834, ABT 829, GSK 189254 and CEP16795); $GABA_A$ signaling enhancer (such as L-838,417, TPA-023, alphaxalone, ganaxolone, gaboxadol, tiagabine, vigabatrine, bumetadine), and blocker (such as S44819), $GABA_B$ signalling enhancer (such as baclofen), V1a receptor antagonist (such as balovaptan); D2 partial agonist; cholinergic agonist; a compound from the phenothiazine, thioxanthene (such as chlorprothixene and thiothixene), heterocyclic dibenzazepine (such as clozapine), butyrophenone (such as haloperidol), diphenylbutylpiperidine (such as pimozide) and indolone (such as molindolone) classes of neuroleptic agents; loxapine, sulpiride; or an atypical antipsychotic (such as aripiprazole, asenapine, brexpiprazole, cariprazine, iloperidone, lurasidone, olanzapine, paliperidone, quetiapine, risperidone and ziprasidone).

The term "modulators" refers to molecules interacting with the target receptor, wherein the interaction can be e.g. agonistic, antagonistic or inverse agonistic.

The term "inhibitors" referes to molecules competing with, reducing or preventing the binding of a particular ligand to a particular receptor or reducing or preventing the inhibition of the function of a particular protein.

The term "agonists" refers to compounds having affinity to a receptor binding site and enhancing the activity of the receptor-mediated response. "Full-agonists" effect a full response, "partial agonists" effects less than full activation even when occupying the total receptor population.

The term "inverse agonists" refers to compounds producing an effect opposite to that of an agonist by binding to the same agonist binding site, or reducing the effect of an agonist by binding at a different allosteric binding site.

The term "antagonists" refers to compounds diminishing or preventing the action of another compound or receptor site, or attenuating the effect of an agonist. "Competitive antagonists" bind to the same site as the agonist but does not activate it, thus blocks the agonists' action. "Non-competitive antagonists" binds to an allosteric site on the receptor to prevent activation of the receptor. Binding of "reversible antagonists" to a receptor is non-covalent (can be washed out), while binding of "irreversible antagonists" is covalent (cannot be washed out).

The term "allosteric modulators" refers to compounds binding to a receptor at a site distinct from the agonist binding site, i.e. to the allosteric site, wherein by inducing conformational change in the receptor, alter the affinity and/or activity of the receptor for the endogenous ligand or agonist. "Positive allosteric modulators" or "PAMs" increase the affinity, whilst "negative allosteric modulators" or "NAMs" decrease the affinity thereby decrease the activity of a receptor indirectly. The compounds of formula (I), as defined above are negative allosteric modulators binding to the benzodiazepine binding site with inverse agonism selective for the $GABA_A$ α5 receptor.

The term "inhibition constant" ($K_i$) refers to the absolute binding affinity of a particular inhibitor to a receptor. It is measured using competition binding assays and is equal to the concentration where the particular inhibitor would occupy half of the receptors if no competing ligand was present. $K_i$ values can be converted logarithmically to $pK_i$ values (−log $K_i$) in which higher values indicate exponentially greater potency.

The term "submaximal effective concentration" refers to the concentration of a particular compound required for obtaining 10% of the maximum of a particular effect.

The term "functional selectivity" refers to the different degrees of modulation by a particular compound at different receptor subtypes. In present invention, a compound is particularly functional selective if it acts as inverse agonist at $GABA_A$ α5 receptor by reducing the effect of GABA by more than 20%, while affecting the other $GABA_A$ receptor subtypes by less than 10%.

The terms "condition", "defect", "deficit", "disability", "disorder", "disease" or "disease state" are used interchangeably to denote any disease, condition, symptom, syndrome, disorder or indication.

The term "diseases related to the $GABA_A$ α5 receptor" refers to diseases, conditions or disorders of the central nervous system where one of the symptoms and/or syndromes of the disease may be related to the $GABA_A$ α5 receptor. These diseases include, but not limited to, neurodegenerative disorders, neurocognitive disorders, schizophrenia, mood disorders, pain disorders, substance-related and addictive disorders or other diseases.

The term "cognition" refers to the processes a subject, preferably a mammal, more preferably a human, uses to organize information, including acquiring information (perception), selecting (attention), representing (understanding) and retaining (memory) information, and using it to guide behavior (reasoning and coordination of motor outputs). Interventions to improve cognitive function may be directed at any one of these core faculties.

In one embodiment, the compounds of formula (I), as defined above are useful as cognition enhancers. The term "cognition enhancer" refers to the improvement of cognitive functions, particularly social cognition, complex attention, executive function, perceptual-motor function, language or learning and memory. Cognitive enhancement is an intervention that improves a subsystem in some way other than repairing something that is broken or remedying a specific dysfunction.

The diseases related to the $GABA_A$ α5 receptor may show comorbidity with each other. Comorbidity indicates a medical condition existing simultaneously but independently with another condition in a patient, or a medical condition in a patient that causes, is caused by, or is otherwise related to another condition in the same patient. However, in psychiatric, psychologic, or mental health diseases comorbidity does not necessarily imply the presence of multiple diseases, but instead can reflect our current inability to supply a single diagnosis that accounts for all symptoms.

The term "neurodegenerative disorder" includes, but not limited to, Alzheimer's disease (AD), Huntington's disease (HD), Parkinson's disease (PD), or amyotrophic lateral sclerosis (ALS).

The term "neurocognitive disorder" includes, but not limited to, cognition deficiency disorders, memory deficits, age-associated memory impairment or cognitive decline, dementia (or different forms thereof such as dementia in Alzheimer's disease, Niemann Pick-disease, Parkinson's disease, or Huntington's disease, dementia with Lewy bodies (DLB), frontotemporal dementia, vascular dementia (VaD), subcortical dementia, mixed vascular and subcortical dementia, multi-infarct dementia, post-operative dementia, or inflammation-induced dementia), mild cognitive impairment (MCI), vascular cognitive impairment (VCI), CNS conditions occurring after stroke, cognitive impairment associated with brain cancers (including but not limited to medulloblastomas), cognitive decline in Down Syndrome (DS), or cognitive dysfunction in major depressive disorder (MDD).

The term "schizophrenia" includes, but not limited to, different forms of schizophrenia, positive, negative and/or cognitive symptoms associated with schizophrenia, schizotypal and delusional disorders.

The term "pain disorder" includes, but not limited to, nociceptive, neuropathic or inflammatory pain.

The term "mood disorder" includes, but not limited to, depression-related disorders (such as major depressive disorder (MDD), dysthymia, cyclothymic disorder, seasonal affective disorder/seasonal depression, depression after traumatic brain injury (TBI), postpartum depression, premenstrual dysphoric disorder, depressive symptoms associated with menopause, depression following substance abuse/withdrawal, bipolar disorders, bipolar disorder in remission, or depressive episodes of bipolar disorder), bipolar disorders, substance (alcohol or drug) induced, or not otherwise specified mood disorders (MD-NOS).

The term "other disease" includes, but not limited to, attention deficit hyperactivity disorder and adult attention deficiency, other stress related conditions, stroke, neurofibromatosis type I, multiple sclerosis, acute meningitis, alcoholism, fetal alcohol syndrome, or bronchoconstrictive diseases (such as asthma, chronic obstructive pulmonary disease, and bronchopulmonary dysplasia).

In one embodiment, the disease related to the $GABA_A$ α5 receptor refers to Alzheimer's disease (AD), Huntington's disease (HD), Parkinson's disease, amyotrophic lateral sclerosis (ALS), cognition deficiency disorders, memory deficits, age-associated memory impairment or cognitive decline, dementia or different forms thereof such as dementia in Alzheimer's disease, Niemann Pick-disease, Parkinson's disease, or Huntington's disease, dementia with Lewy bodies (DLB), frontotemporal dementia, vascular dementia (VaD), subcortical dementia, mixed vascular and subcortical dementia, multi-infarct dementia, post-operative dementia, or inflammation-induced dementia), mild cognitive impairment (MCI), vascular cognitive impairment (VCI), CNS conditions occurring after stroke, cognitive impairment associated with brain cancers (including but not limited to medulloblastomas), cognitive decline in Down Syndrome (DS), cognitive dysfunction in major depressive disorder (MDD); different forms of schizophrenia, positive, negative and/or cognitive symptoms associated with schizophrenia, schizotypal and delusional disorders; nociceptive, neuropathic or inflammatory pain; depression-related disorders (such as major depressive disorder (MDD), dysthymia, cyclothymic disorder, seasonal affective disorder/seasonal depression, depression after traumatic brain injury (TBI), postpartum depression, premenstrual dysphoric disorder, depressive symptoms associated with menopause, depression following substance abuse/withdrawal, bipolar disorders, bipolar disorder in remission, or depressive episodes of bipolar disorder), bipolar disorders, substance (alcohol or drug) induced, not otherwise specified mood disorders (MD- NOS); attention deficit hyperactivity disorder and adult attention deficiency, other stress related conditions, stroke, neurofibromatosis type I, multiple sclerosis, acute meningitis, alcoholism, fetal alcohol syndrome, or bronchoconstrictive diseases (such as asthma, chronic obstructive pulmonary disease, and bronchopulmonary dysplasia).

In one embodiment, the disease related to the $GABA_A$ α5 receptor refers to Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia.

The present invention provides a method of treating or preventing diseases related to the $GABA_A$ α5 receptor, or for cognition enhancement, comprising administering to a subject, preferably a mammal, more preferably a human being, in need of such treatment or prevention, therapeutically effective amount of a compound of formula (I), as defined above alone or with at least one pharmaceutically acceptable excipient in the form of a pharmaceutical formulation.

The present invention provides a method of treating or preventing diseases related to the $GABA_A$ α5 receptor, or for cognition enhancement, comprising administering to a subject, preferably a mammal, more preferably a human being, in need of such treatment or prevention, therapeutically effective amount of a compound of formula (I), as defined above in combination with one or more other active ingredients.

The present invention provides a method of treating or preventing of neurodegenerative disorders, neurocognitive disorders, schizophrenia, mood disorders, pain disorders, substance-related and addictive disorders or other diseases, or at least one of the symptoms and/or syndromes thereof, where one of the symptoms and/or syndromes of the disease may be related to the $GABA_A$α5 receptor, in a subject, preferably a mammal, more preferably a human being, suffering therefrom, or for cognition enhancement. This method of treatment comprises administering to a subject, preferably a mammal, more preferably a human being, in need of such treatment or prevention, therapeutically effective amount of the compound of formula (I), as defined above. The method of treatment may include administering to a subject preferably a mammal, more preferably a human being, in need of such treatment therapeutically effective amount of a pharmaceutical composition comprising the compound of formula (I), as defined above.

The present invention provides a method of treating or preventing Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, in a subject, preferably a mammal, more preferably a human being, suffering therefrom, or for cognition enhancement.

The present invention provides the compound of formula (I), as defined above for use in the treatment or prevention of diseases related to the $GABA_A$ α5 receptor, or for use as cognition enhancer.

The present invention provides the compound of formula (I), as defined above in combination with one or more other active ingredients for use in the treatment or prevention of diseases related to the $GABA_A$ α5 receptor, or for use as cognition enhancer.

The present invention provides the compound of formula (I), as defined above for use in the treatment or prevention of neurodegenerative disorders, neurocognitive disorders, schizophrenia, mood disorders, pain disorders, substance-related and addictive disorders or other diseases, or at least one of the symptoms and/or syndromes thereof, or as cognition enhancer.

The present invention provides the compound of formula (I), as defined above for use in the treatment or prevention of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, or as cognition enhancer.

The present invention provides the use of the compound of formula (I), as defined above for the manufacture of a medicament for the treatment or prevention of diseases related to the $GABA_A$ α5 receptor, or for cognition enhancement.

The present invention provides the use of the compound of formula (I), as defined above in combination with one or more other active ingredients, for the manufacture of a medicament for the treatment or prevention of diseases related to the $GABA_A$ α5 receptor, or for cognition enhancement.

The present invention provides the use of the compound of formula (I), as defined above for the manufacture of a medicament for the treatment or prevention of neurodegenerative disorders, neurocognitive disorders, schizophrenia, mood disorders, pain disorders, substance-related and addictive disorders or other diseases, or at least one of the symptoms and/or syndromes thereof, or for cognition enhancement.

The present invention provides the use of the compound of formula (I), as defined above for the manufacture of a medicament for the treatment or prevention of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, or for cognition enhancement.

The present invention also relates to pharmaceutical composition comprising the compound of formula (I), as defined above for use in the treatment or prevention of diseases related to the $GABA_A$α5 receptor, or for cognition enhancement.

The present invention also relates to pharmaceutical composition comprising the compound of formula (I), as defined above with one or more other active ingredients for use in the treatment or prevention of diseases related to the $GABA_A$ α5 receptor, or for cognition enhancement.

The term "treatment" refers to the alleviation of a specific pathological condition, the elimination or reduction of one or more of the symptoms of the condition, the slowing or elimination of the progression of the disease state, and the prevention or delay of recurrency of the pathological condition of a patient or subject already suffering from ordiagnosed with the disease. The "prevention" (or prophylaxis or delay of action of the disease) is typically performed by administering the drug in the same or similar way as if it were given to a patient with a disease or condition already developed.

The term "therapeutically effective amount" refers to the amount of active ingredient—in comparison with the corresponding subject who did not receive such amount—which results in the treatment, cure, prevention or improvement of the disease or disease state or side effect, and reduces the progression of the disease or pathological condition. The term also includes effective amounts to enhance normal physiological function. For use in therapy the compound of formula (I), as defined above as well as any pharmaceutically acceptable salt thereof may be administered in a therapeutically effective amount as a raw chemical. In addition, the active ingredient is available as a pharmaceutical formulation. The exact therapeutically effective amount of the compound of formula (I), as defined above depends on a number of factors including, but not limited to, the age and body weight of the subject (patient), the precise type of disease requiring treatment and its seriousness, the nature of the medicinal product and the route of administration.

The term "subject" refers to a vertebrate. In certain embodiments, the vertebrate is a mammal. Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In one embodiment, the present invention relates to compounds of formula (I')

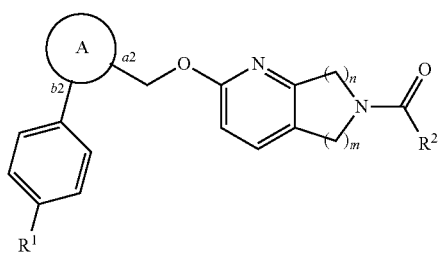

wherein
$R^1$ to $R^7$, n and m are as defined above for the compounds of formula (I)
A is represented by

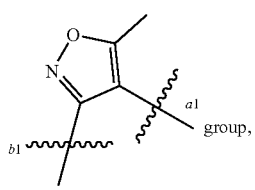
group,

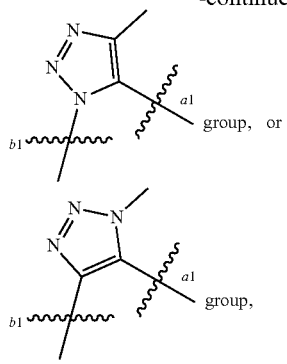

wherein site "a1" of any ring A is attached to site "a2" and wherein site "b1" of any ring A is attached to site "b2".

In one embodiment, the present invention relates to compounds of formula (I-a)

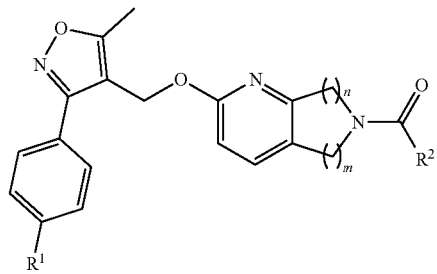

wherein
$R^1$ is hydrogen or halogen,
n and m are each independently 1 or 2,
$R^2$ is hydrogen; $C_{1-4}$alkyl optionally and independently substituted with one ore more halogen, $C_{1-4}$alkoxy, —S(O)$_2$—$C_{1-4}$alkyl, or with $R^3$; $NR^4R^5$ or $R^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^3$, $R^6$ and $R^7$ is optionally substituted carbocycle, heterocycle or heteroaryl,
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

In one embodiment, the present invention relates to compounds of formula (I-b)

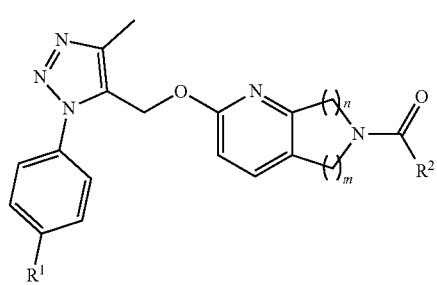

wherein
R$^1$ is hydrogen or halogen,
n and m are each independently 1 or 2,
R$^2$ is hydrogen; C$_{1-4}$alkyl optionally and independently substituted with one ore more halogen, C$_{1-4}$alkoxy, —S(O)$_2$—C$_{1-4}$alkyl, or with R$^3$; NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form an optionally substituted heterocycle, and R$^3$, R$^6$ and R$^7$ is optionally substituted carbocycle, heterocycle or heteroaryl, and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

In one embodiment, the present invention relates to compounds of formula (I-c)

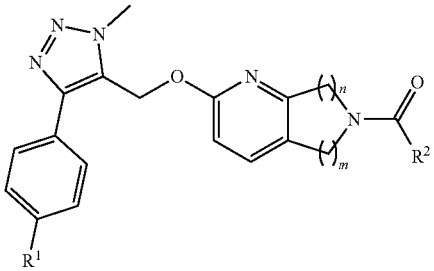

wherein
R$^1$ is hydrogen or halogen,
n and m are each independently 1 or 2,
R$^2$ is hydrogen; C$_{1-4}$alkyl optionally and independently substituted with one ore more halogen, C$_{1-4}$alkoxy, —S(O)$_2$—C$_{1-4}$alkyl, or with R$^3$; NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form an optionally substituted heterocycle, and R$^3$, R$^6$ and R$^7$ is optionally substituted carbocycle, heterocycle or heteroaryl,
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

In one embodiment, the present invention relates to compounds of formula (I) wherein R$^1$ is hydrogen.

In one embodiment, the present invention relates to compounds of formula (I) wherein R$^1$ is fluorine, chlorine or bromine.

In one embodiment, the present invention relates to compounds of formula (I) wherein R$^2$ is hydrogen.

In one embodiment, the present invention relates to compounds of formula (I) wherein R$^2$ is C$_{1-4}$alkyl.

In one embodiment, the present invention relates to compounds of formula (I) wherein R$^2$ is haloC$_{1-4}$alkyl.

In one embodiment, the present invention relates to compounds of formula (I) wherein R$^2$ is C$_{1-4}$alkoxyC$_{1-4}$alkyl.

In one embodiment, the present invention relates to compounds of formula (I) wherein R$^2$ is methoxymethyl.

In one embodiment, the present invention relates to compounds of formula (I) wherein R$^2$ is C$_{1-4}$alkyl-S(O)$_2$—C$_{1-4}$alkyl.

In one embodiment, the present invention relates to compounds of formula (I) wherein R$^2$ is methylsulfonylmethane or ethylsulfonylmethane.

In one embodiment, the present invention relates to compounds of formula (I) wherein R$^2$ is C$_{1-4}$alkyl substituted with optionally substituted carbocycle, heterocycle or heteroaryl.

In one embodiment, the present invention relates to compounds of formula (I) wherein R$^2$ is NR$^4$R$^5$.

In one embodiment, the present invention relates to compounds of formula (I) wherein R$^2$ is NR$^4$R$^5$ and R$^4$ and R$^5$ are hydrogen.

In one embodiment, the present invention relates to compounds of formula (I) wherein R$^2$ is NR$^4$R$^5$ and R$^4$ and R$^5$ are C$_{1-4}$alkyl.

In one embodiment, the present invention relates to compounds of formula (I) wherein R$^2$ is NR$^4$R$^5$ and R$^4$ is hydrogen, R$^5$ is C$_{1-4}$alkyl.

In one embodiment, the present invention relates to compounds of formula (I) wherein R$^2$ is NR$^4$R$^5$ and R$^4$ is hydrogen, R$^5$ is optionally substituted carbocycle, heterocycle or heteroaryl.

In one embodiment, the present invention relates to compounds of formula (I) wherein R$^2$ is NR$^4$R$^5$ and R$^4$ is C$_{1-4}$alkyl, R$^5$ is C$_{1-4}$alkyl or optionally substituted carbocycle, heterocycle or heteroaryl.

In one embodiment, the present invention relates to compounds of formula (I) wherein R$^2$ is NR$^4$R$^5$ and R$^4$ and R$^5$ are taken together with the N to which they are attached to form an optionally substituted heterocycle.

In one embodiment, the present invention relates to compounds of formula (I) wherein R$^2$ is NR$^4$R$^5$ and R$^4$ is hydrogen, R$^5$ is optionally substituted heterocycle or R$^4$ and R$^5$ are taken together with the N to which they are attached to form an optionally substituted monocyclic heterocycle.

In one embodiment, the present invention relates to compounds of formula (I) wherein R$^2$ is optionally substituted carbocycle, heterocycle or heteroaryl.

In one embodiment, the present invention relates to compounds of formula (I) wherein R$^2$ is optionally substituted C$_{3-6}$cycloalkyl, C$_{6-10}$aryl, C$_{4-6}$heterocycle comprising 1 or 2 ring heteroatoms independently selected from N, O and S or C$_{5-6}$heteroaryl comprising 1 or 2 ring heteroatoms independently selected from N and O.

In one embodiment, the present invention relates to compounds of formula (I) wherein R$^2$ is C$_{3-6}$cycloalkyl, C$_{6-10}$aryl, C$_{4-6}$heterocycle comprising 1 or 2 ring heteroatoms independently selected from N, O and S or C$_{5-6}$heteroaryl comprising 1 or 2 ring heteroatoms independently selected from N and O substituted with C$_{1-4}$alkyl, C$_{1-4}$alkoxy, halogen, haloC$_{1-4}$alkyl, haloC$_{1-4}$alkoxy, hydroxyl or oxo.

In one embodiment, the present invention relates to compounds of formula (I) wherein the optionally substituted carbocycle, heterocycle or heteroaryl is selected from the group comprising cyclopropyl, cyclobutane, cyclohexane, phenyl, oxetane, tetrahydrofuran, tetrahydropyran, thiane, pyrrolidine, piperidine, pyridine, isoxazole, pyrrole and morpholine.

In one embodiment, the present invention relates to compounds of formula (I) wherein n is 1 and m is 2.

In one embodiment, the present invention relates to compounds of formula (I) wherein n is 2 and m is 1.

In one embodiment, the present invention relates to compounds of formula (I) wherein n and m are 1.

In one embodiment, the present invention relates to compounds of formula (I) wherein n is 2 and m is 2.

In one embodiment, the present invention relates to compounds of formula (I) wherein $R^1$ is halogen, n and m are each independently 1 or 2 and $R^2$ is $C_{1-4}$alkoxy$C_{1-4}$alkyl.

In one embodiment, the present invention relates to compounds of formula (I) wherein $R^1$ is halogen, n and m are each independently 1 or 2 and $R^2$ is $C_{1-4}$alkyl-S(O)$_2$—$C_{1-4}$alkyl.

In one embodiment, the present invention relates to compounds of formula (I) wherein $R^1$ is halogen, n and m are each independently 1 or 2 and $R^2$ is $NR^4R^5$.

In one embodiment, the present invention relates to compounds of formula (I) wherein $R^1$ is halogen, n and m are each independently 1 or 2 and $R^2$ is optionally substituted carbocycle, heterocycle or heteroaryl.

In one embodiment, the present invention relates to compounds of formula (I) wherein
$R^1$ is fluorine, bromine or chlorine,
$R^2$ is $C_{1-3}$alkyl, $C_{1-4}$alkoxy$C_{1-3}$alkyl, $C_{1-3}$alkyl-S(O)$_2$—$C_{1-3}$alkyl, $NR^4R^5$ or $R^6$,
$R^4$ and $R^5$ are each independently hydrogen, $C_{1-4}$alkyl or $R^7$, and
$R^6$ and $R^7$ is a $C_{3-6}$cycloalkyl, $C_{6-10}$aryl, $C_{4-6}$heterocycle comprising 1 or 2 ring heteroatoms independently selected from N, O and S or $C_{5-6}$heteroaryl comprising 1 or 2 ring heteroatoms independently selected from N and O optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is fluorine or chlorine,
$R^2$ is $C_{1-4}$alkoxy$C_{1-3}$alkyl, methylsulfonylmethane, ethylsulfonylmethane, $NR^4R^5$ or $R^6$,
$R^4$ and $R^5$ are each independently hydrogen, $C_{1-3}$alkyl or $R^7$, and
$R^6$ and $R^7$ is carbocycle, heterocycle or heteroaryl selected from the group comprising cyclopropyl, cyclobutane, cyclohexane, phenyl, oxetane, tetrahydrofuran, tetrahydropyran, thiane, pyrrolidine, piperidine, pyridine, isoxazole, pyrrole and morpholine optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is halogen,
n is 1 and m is 2
$R^2$ is $C_{1-4}$alkyl optionally and independently substituted with $C_{1-4}$alkoxy, —S(O)$_2$—$C_{1-4}$alkyl; $NR^4R^5$ or $R^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^3$, $R^6$ and $R^7$ is optionally substituted carbocycle, heterocycle or heteroaryl.

In one embodiment, the present invention relates to compounds of formula (I) wherein
$R^1$ is fluorine, chlorine or bromine,
n is 1 and m is 2
$R^2$ is $C_{1-3}$alkyl, $C_{1-4}$alkoxy$C_{1-3}$alkyl, $C_{1-3}$alkyl-S(O)$_2$—$C_{1-3}$alkyl, $NR^4R^5$ or $R^6$,
$R^4$ and $R^5$ are each independently hydrogen, $C_{1-4}$alkyl or $R^7$, and
$R^6$ and $R^7$ is a $C_{3-6}$cycloalkyl, $C_{6-10}$aryl, $C_{4-6}$heterocycle comprising 1 or 2 ring heteroatoms independently selected from N, O and S or $C_{5-6}$heteroaryl comprising 1 or 2 ring heteroatoms independently selected from N and O optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is fluorine or chlorine,
n is 1 and m is 2
$R^2$ is $C_{1-4}$alkoxy$C_{1-3}$alkyl, methylsulfonylmethane, ethylsulfonylmethane, $NR^4R^5$ or $R^6$,
$R^4$ and $R^5$ are each independently hydrogen, $C_{1-3}$alkyl or $R^7$, and
$R^6$ and $R^7$ is carbocycle, heterocycle or heteroaryl selected from the group comprising cyclopropyl, cyclobutane, cyclohexane, phenyl, oxetane, tetrahydrofuran, tetrahydropyran, thiane, pyrrolidine, piperidine, pyridine, isoxazole, pyrrole and morpholine optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is halogen,
n is 2 and m is 1
$R^2$ is $C_{1-4}$alkyl optionally and independently substituted with $C_{1-4}$alkoxy, —S(O)$_2$—$C_{1-4}$alkyl; $NR^4R^5$ or $R^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^3$, $R^6$ and $R^7$ is optionally substituted carbocycle, heterocycle or heteroaryl.

In one embodiment, the present invention relates to compounds of formula (I) wherein
$R^1$ is fluorine, bromine or chlorine,
n is 2 and m is 1
$R^2$ is $C_{1-3}$alkyl, $C_{1-4}$alkoxy$C_{1-3}$alkyl, $C_{1-3}$alkyl-S(O)$_2$—$C_{1-3}$alkyl, $NR^4R^5$ or $R^6$,
$R^4$ and $R^5$ are each independently hydrogen, $C_{1-4}$alkyl or $R^7$, and
$R^6$ and $R^7$ is a $C_{3-6}$cycloalkyl, $C_{6-10}$aryl, $C_{4-6}$heterocycle comprising 1 or 2 ring heteroatoms independently selected from N, O and S or $C_{5-6}$heteroaryl comprising 1 or 2 ring heteroatoms independently selected from N and O optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is fluorine or chlorine,
n is 2 and m is 1
$R^2$ is $C_{1-4}$alkoxy$C_{1-3}$alkyl, methylsulfonylmethane, ethylsulfonylmethane, $NR^4R^5$ or $R^6$,
$R^4$ and $R^5$ are each independently hydrogen, $C_{1-3}$alkyl or $R^7$, and
$R^6$ and $R^7$ is carbocycle, heterocycle or heteroaryl selected from the group comprising cyclopropyl, cyclobutane, cyclohexane, phenyl, oxetane, tetrahydrofuran, tetrahydropyran, thiane, pyrrolidine, piperidine, pyridine, isoxazole, pyrrole and morpholine optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is halogen,
n and m are 1,
$R^2$ is $C_{1-4}$alkyl optionally and independently substituted with $C_{1-4}$alkoxy, —S(O)$_2$—$C_{1-4}$alkyl; $NR^4R^5$ or $R^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^6$ and $R^7$ is optionally substituted carbocycle, heterocycle or heteroaryl.

In one embodiment, the present invention relates to compounds of formula (I) wherein
$R^1$ is fluorine, chlorine or bromine,
n and m are 1,
$R^2$ is $C_{1-3}$alkyl, $C_{1-4}$alkoxy$C_{1-3}$alkyl, $C_{1-3}$alkyl-S(O)$_2$—$C_{1-3}$alkyl, NR$^4$R$^5$ or R$^6$,
$R^4$ and $R^5$ are each independently hydrogen, $C_{1-4}$alkyl or $R^7$, and
$R^6$ and $R^7$ is a $C_{3-6}$cycloalkyl, $C_{6-10}$aryl, $C_{4-6}$heterocycle comprising 1 or 2 ring heteroatoms independently selected from N, O and S or $C_{5-6}$heteroaryl comprising 1 or 2 ring heteroatoms independently selected from N and O optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is fluorine or chlorine,
n and m are 1,
$R^2$ is $C_{1-4}$alkoxy$C_{1-3}$alkyl, methylsulfonylmethane, ethylsulfonylmethane, NR$^4$R$^5$ or R$^6$,
$R^4$ and $R^5$ are each independently hydrogen, $C_{1-3}$alkyl or $R^7$, and
$R^6$ and $R^7$ is carbocycle, heterocycle or heteroaryl selected from the group comprising cyclopropyl, cyclobutane, cyclohexane, phenyl, oxetane, tetrahydrofuran, tetrahydropyran, thiane, pyrrolidine, piperidine, pyridine, isoxazole, pyrrole and morpholine optionally substituted with $C_{1-4}$alkyl, $C_{1-4}$alkoxy, halogen, halo$C_{1-4}$alkyl, halo$C_{1-4}$alkoxy, hydroxyl or oxo.

In one embodiment, the present invention relates to compounds of formula (I) wherein
$R^1$ is halogen,
n and m are 2,
$R^2$ is $C_{1-4}$alkyl optionally and independently substituted with $C_{1-4}$alkoxy, —S(O)$_2$—$C_{1-4}$alkyl; NR$^4$R$^5$ or R$^6$,
$R^4$ and $R^5$ are each independently hydrogen, $C_{1-4}$alkyl or $R^7$; or $R^4$ and $R^5$ are taken together with the N to which they are attached to form an optionally substituted heterocycle, and $R^6$ and $R^7$ is optionally substituted carbocycle, heterocycle or heteroaryl.

Any combination of the embodiments of A, $R^1$-$R^7$, n and m as defined above are preferred groups of compounds of formula (I).

In one embodiment, the present invention relates to compounds of formula (I), as defined above selected from the group consisting of:
1-[2-{[3-(4-fluorophenyl)-5-methyl-1,2-oxazol-4-yl]methoxy}-7,8-dihydro-1,6-naphthyridin-6(5H)-yl]ethanone,
2-{[3-(4-fluorophenyl)-5-methyl-1,2-oxazol-4-yl]methoxy}-6-(oxolane-3-carbonyl)-5,6,7,8-tetrahydro-1,6-naphthyridine,
2-{[3-(4-fluorophenyl)-5-methyl-1,2-oxazol-4-yl]methoxy}-6-(1,2-oxazole-5-carbonyl)-5,6,7,8-tetrahydro-1,6-naphthyridine,
6-cyclobutanecarbonyl-2-{[3-(4-fluorophenyl)-5-methyl-1,2-oxazol-4-yl]methoxy}-5,6,7,8-tetrahydro-1,6-naphthyridine,
6-cyclopropanecarbonyl-2-{[3-(4-fluorophenyl)-5-methyl-1,2-oxazol-4-yl]methoxy}-5,6,7,8-tetrahydro-1,6-naphthyridine,
4-(2-{[3-(4-fluorophenyl)-5-methyl-1,2-oxazol-4-yl]methoxy}-5,6,7,8-tetrahydro-1,6-naphthyridine-6-carbonyl)-1lambda6-thiane-1,1-dione,
2-{[3-(4-fluorophenyl)-5-methyl-1,2-oxazol-4-yl]methoxy}-6-(oxolane-2-carbonyl)-5,6,7,8-tetrahydro-1,6-naphthyridine,
1-(2-{[3-(4-fluorophenyl)-5-methyl-1,2-oxazol-4-yl]methoxy}-5,6,7,8-tetrahydro-1,6-naphthyridin-6-yl)-2-methanesulfonylethan-1-one,
2-{[3-(4-fluorophenyl)-5-methyl-1,2-oxazol-4-yl]methoxy}-6-(oxane-4-carbonyl)-5,6,7,8-tetrahydro-1,6-naphthyridine,
2-{[3-(4-fluorophenyl)-5-methyl-1,2-oxazol-4-yl]methoxy}-6-(5-methyl-1,2-oxazole-3-carbonyl)-5,6,7,8-tetrahydro-1,6-naphthyridine,
2-{[3-(4-fluorophenyl)-5-methyl-1,2-oxazol-4-yl]methoxy}-6-(1-methyl-1H-pyrrole-3-carbonyl)-5,6,7,8-tetrahydro-1,6-naphthyridine,
2,2,2-trifluoro-1-(2-{[3-(4-fluorophenyl)-5-methyl-1,2-oxazol-4-yl]methoxy}-5,6,7,8-tetrahydro-1,6-naphthyridin-6-yl)ethan-1-one,
4-(2-{[3-(4-fluorophenyl)-5-methyl-1,2-oxazol-4-yl]methoxy}-5,6,7,8-tetrahydro-1,6-naphthyridine-6-carbonyl)-1-methylpyrrolidin-2-one,
1-(2-{[1-(4-fluorophenyl)-4-methyl-1H-1,2,3-triazol-5-yl]methoxy}-5,6,7,8-tetrahydro-1,6-naphthyridin-6-yl)ethan-1-one,
2-{[1-(4-fluorophenyl)-4-methyl-1H-1,2,3-triazol-5-yl]methoxy}-6-(oxolane-2-carbonyl)-5,6,7,8-tetrahydro-1,6-naphthyridine,
2-{[1-(4-fluorophenyl)-4-methyl-1H-1,2,3-triazol-5-yl]methoxy}-6-(oxolane-3-carbonyl)-5,6,7,8-tetrahydro-1,6-naphthyridine,
2-{[1-(4-fluorophenyl)-4-methyl-1H-1,2,3-triazol-5-yl]methoxy}-6-[(3R)-oxolane-3-carbonyl]-5,6,7,8-tetrahydro-1,6-naphthyridine,
2-{[1-(4-fluorophenyl)-4-methyl-1H-1,2,3-triazol-5-yl]methoxy}-6-[(3S)-oxolane-3-carbonyl]-5,6,7,8-tetrahydro-1,6-naphthyridine,
6-cyclopropanecarbonyl-2-{[1-(4-fluorophenyl)-4-methyl-1H-1,2,3-triazol-5-yl]methoxy}-5,6,7,8-tetrahydro-1,6-naphthyridine,
2-{[1-(4-fluorophenyl)-4-methyl-1H-1,2,3-triazol-5-yl]methoxy}-6-(1,2-oxazole-5-carbonyl)-5,6,7,8-tetrahydro-1,6-naphthyridine,
4-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one,
1-(2-{[1-(4-fluorophenyl)-4-methyl-1H-1,2,3-triazol-5-yl]methoxy}-5,6,7,8-tetrahydro-1,6-naphthyridin-6-yl)-2-methylpropan-1-one,
4-(2-{[1-(4-fluorophenyl)-4-methyl-1H-1,2,3-triazol-5-yl]methoxy}-5,6,7,8-tetrahydro-1,6-naphthyridine-6-carbonyl)-1lambda6-thiane-1,1-dione,
1-(2-{[1-(4-fluorophenyl)-4-methyl-1H-1,2,3-triazol-5-yl]methoxy}-5,6,7,8-tetrahydro-1,6-naphthyridin-6-yl)propan-1-one,
2-{[1-(4-fluorophenyl)-4-methyl-1H-1,2,3-triazol-5-yl]methoxy}-6-(pyridine-4-carbonyl)-5,6,7,8-tetrahydro-1,6-naphthyridine,
2-{[1-(4-fluorophenyl)-4-methyl-1H-1,2,3-triazol-5-yl]methoxy}-6-(pyridine-2-carbonyl)-5,6,7,8-tetrahydro-1,6-naphthyridine,
6-(3-chlorobenzoyl)-2-{[1-(4-fluorophenyl)-4-methyl-1H-1,2,3-triazol-5-yl]methoxy}-5,6,7,8-tetrahydro-1,6-naphthyridine,
2-{[1-(4-fluorophenyl)-4-methyl-1H-1,2,3-triazol-5-yl]methoxy}-6-(oxane-4-carbonyl)-5,6,7,8-tetrahydro-1,6-naphthyridine,
2-{[1-(4-chlorophenyl)-4-methyl-1H-1,2,3-triazol-5-yl]methoxy}-6-(oxolane-3-carbonyl)-5,6,7,8-tetrahydro-1,6-naphthyridine, 2-{[1-(4-fluorophenyl)-4-methyl-1H-1,2,3-triazol-5-yl]
methoxy}-6-(oxane-3-carbonyl)-5,6,7,8-tetrahydro-1,6-
naphthyridine,
2-{[1-(4-fluorophenyl)-4-methyl-1H-1,2,3-triazol-5-yl]
methoxy}-6-(3-methyloxolane-3-carbonyl)-5,6,7,8-tetra-
hydro-1,6-naphthyridine,
2-{[1-(4-chlorophenyl)-4-methyl-1H-1,2,3-triazol-5-yl]
methoxy}-6-(oxane-4-carbonyl)-5,6,7,8-tetrahydro-1,6-
naphthyridine,
2-{[1-(4-chlorophenyl)-4-methyl-1H-1,2,3-triazol-5-yl]
methoxy}-6-(pyridine-4-carbonyl)-5,6,7,8-tetrahydro-1,
6-naphthyridine,
1-(2-{[1-(4-fluorophenyl)-4-methyl-1H-1,2,3-triazol-5-yl]
methoxy}-5,6,7,8-tetrahydro-1,7-naphthyridin-7-yl)
ethan-1-one,
2-{[1-(4-fluorophenyl)-4-methyl-1H-1,2,3-triazol-5-yl]
methoxy}-6-(4-methoxycyclohexanecarbonyl)-5,6,7,8-
tetrahydro-1,6-naphthyridine,
1-(2-{[1-(4-chlorophenyl)-4-methyl-1H-1,2,3-triazol-5-yl]
methoxy}-5,6,7,8-tetrahydro-1,6-naphthyridin-6-yl)
ethan-1-one,
2-{[1-(4-fluorophenyl)-4-methyl-1H-1,2,3-triazol-5-yl]
methoxy}-6-[6-(trifluoromethyl)pyridine-3-carbonyl]-5,
6,7,8-tetrahydro-1,6-naphthyridine,
2-{[1-(4-chlorophenyl)-4-methyl-1H-1,2,3-triazol-5-yl]
methoxy}-6-[(3S)-oxolane-3-carbonyl]-5,6,7,8-tetra-
hydro-1,6-naphthyridine,
2-{[1-(4-fluorophenyl)-4-methyl-1H-1,2,3-triazol-5-yl]
methoxy}-6-(pyridine-3-carbonyl)-5,6,7,8-tetrahydro-1,
6-naphthyridine,
(5S)-5-(2-{[1-(4-fluorophenyl)-4-methyl-1H-1,2,3-triazol-
5-yl]methoxy}-5,6,7,8-tetrahydro-1,6-naphthyridine-6-
carbonyl)-1-methylpyrrolidin-2-one,
(5R)-5-(2-{[1-(4-fluorophenyl)-4-methyl-1H-1,2,3-triazol-
5-yl]methoxy}-5,6,7,8-tetrahydro-1,6-naphthyridine-6-
carbonyl)-1-methylpyrrolidin-2-one,
1-(2-{[1-(4-chlorophenyl)-4-methyl-1H-1,2,3-triazol-5-yl]
methoxy}-5,6,7,8-tetrahydro-1,6-naphthyridin-6-yl)-2-
methoxyethan-1-one,
1-ethyl-4-(2-{[1-(4-fluorophenyl)-4-methyl-1H-1,2,3-tri-
azol-5-yl]methoxy}-5,6,7,8-tetrahydro-1,6-naphthyri-
dine-6-carbonyl)pyrrolidin-2-one,
4-(2-{[1-(4-fluorophenyl)-4-methyl-1H-1,2,3-triazol-5-yl]
methoxy}-5,6,7,8-tetrahydro-1,6-naphthyridine-6-carbo-
nyl)-1-(propan-2-yl)pyrrolidin-2-one,
1-(2-{[1-(4-fluorophenyl)-4-methyl-1H-1,2,3-triazol-5-yl]
methoxy}-5H,6H,7H-pyrrolo[3,4-b]pyridin-6-yl)ethan-1-
one,
5-(2-{[1-(4-fluorophenyl)-4-methyl-1H-1,2,3-triazol-5-yl]
methoxy}-5,6,7,8-tetrahydro-1,6-naphthyridine-6-carbo-
nyl)-1-methylpiperidin-2-one,
cyclopropyl(2-{[1-(4-fluorophenyl)-4-methyl-1H-1,2,3-tri-
azol-5-yl]methoxy}-5,7-dihydro-6H-pyrrolo[3,4-b]pyri-
din-6-yl)methanone,
1-(2-{[3-(4-fluorophenyl)-5-methyl-1,2-oxazol-4-yl]
methoxy}-5,6,7,8-tetrahydro-1,6-naphthyridin-6-yl)-3-
methanesulfonylpropan-1-one,
1-(2-{[3-(4-fluorophenyl)-5-methyl-1,2-oxazol-4-yl]
methoxy}-5H,6H,7H-pyrrolo[3,4-b]pyridin-6-yl)-2-
methanesulfonylethan-1-one,
1-(2-{[3-(4-fluorophenyl)-5-methyl-1,2-oxazol-4-yl]
methoxy}-5,7-dihydro-6H-pyrrolo[3,4-b]pyridin-6-yl)
ethanone,
2,2,2-trifluoro-1-(2-{[1-(4-fluorophenyl)-4-methyl-1H-1,2,
3-triazol-5-yl]methoxy}-5,7-dihydro-6H-pyrrolo[3,4-b]
pyridin-6-yl)ethanone,
1-(2-{[1-(4-fluorophenyl)-4-methyl-1H-1,2,3-triazol-5-yl]
methoxy}-5,7-dihydro-6H-pyrrolo[3,4-b]pyridin-6-yl)
propan-1-one,
2,2-difluoro-1-(2-{[1-(4-fluorophenyl)-4-methyl-1H-1,2,3-
triazol-5-yl]methoxy}-5,7-dihydro-6H-pyrrolo[3,4-b]
pyridin-6-yl)ethanone,
2-fluoro-1-(2-{[1-(4-fluorophenyl)-4-methyl-1H-1,2,3-tri-
azol-5-yl]methoxy}-5,7-dihydro-6H-pyrrolo[3,4-b]pyri-
din-6-yl)ethanone,
1-(4-fluorophenyl)-4-methyl-5-({[6-(oxane-4-carbonyl)-
5H,6H,7H-pyrrolo[3,4-b]pyridin-2-yl]oxy}methyl)-1H-
1,2,3-triazole,
1-(2-{[1-(4-fluorophenyl)-4-methyl-1H-1,2,3-triazol-5-yl]
methoxy}-5H,6H,7H-pyrrolo[3,4-b]pyridin-6-yl)-3-
methylbutan-1-one,
5-[({6-cyclobutanecarbonyl-5H,6H,7H-pyrrolo[3,4-b]pyri-
din-2-yl}oxy)methyl]-1-(4-fluorophenyl)-4-methyl-1H-
1,2,3-triazole,
1-(2-{[1-(4-fluorophenyl)-4-methyl-1H-1,2,3-triazol-5-yl]
methoxy}-5H,6H,7H-pyrrolo[3,4-b]pyridin-6-yl)-2-
methylpropan-1-one,
1-(2-{[1-(4-fluorophenyl)-4-methyl-1H-1,2,3-triazol-5-yl]
methoxy}-5H,6H,7H-pyrrolo[3,4-b]pyridin-6-yl)-2,2-di-
methylpropan-1-one,
1-(2-{[1-(4-chlorophenyl)-4-methyl-1H-1,2,3-triazol-5-yl]
methoxy}-5,7-dihydro-6H-pyrrolo[3,4-b]pyridin-6-yl)
ethanone,
1-(4-fluorophenyl)-4-methyl-5-({[6-(oxolane-2-carbonyl)-
5H,6H,7H-pyrrolo[3,4-b]pyridin-2-yl]oxy}methyl)-1H-
1,2,3-triazole,
1-(4-fluorophenyl)-4-methyl-5-({[6-(oxolane-3-carbonyl)-
5H,6H,7H-pyrrolo[3,4-b]pyridin-2-yl]oxy}methyl)-1H-
1,2,3-triazole,
1-(4-fluorophenyl)-4-methyl-5-({[6-(oxane-3-carbonyl)-
5H,6H,7H-pyrrolo[3,4-b]pyridin-2-yl]oxy}methyl)-1H-
1,2,3-triazole,
4-(2-{[1-(4-fluorophenyl)-4-methyl-1H-1,2,3-triazol-5-yl]
methoxy}-5H,6H,7H-pyrrolo[3,4-b]pyridine-6-carbonyl)
pyridine,
3-(2-{[1-(4-fluorophenyl)-4-methyl-1H-1,2,3-triazol-5-yl]
methoxy}-5H,6H,7H-pyrrolo[3,4-b]pyridine-6-carbonyl)
pyridine,
2-(2-{[1-(4-fluorophenyl)-4-methyl-1H-1,2,3-triazol-5-yl]
methoxy}-5H,6H,7H-pyrrolo[3,4-b]pyridine-6-carbonyl)
pyridine,
1-(2-{[4-(4-fluorophenyl)-1-methyl-1H-1,2,3-triazol-5-yl]
methoxy}-5,7-dihydro-6H-pyrrolo[3,4-b]pyridin-6-yl)
ethanone,
1-(2-{[4-(4-chlorophenyl)-1-methyl-1H-1,2,3-triazol-5-yl]
methoxy}-5,7-dihydro-6H-pyrrolo[3,4-b]pyridin-6-yl)
ethanone,
1-(2-{[4-(4-fluorophenyl)-1-methyl-1H-1,2,3-triazol-5-yl]
methoxy}-5,7-dihydro-6H-pyrrolo[3,4-b]pyridin-6-yl)
propan-1-one,
2-fluoro-1-(2-{[4-(4-fluorophenyl)-1-methyl-1H-1,2,3-tri-
azol-5-yl]methoxy}-5,7-dihydro-6H-pyrrolo[3,4-b]pyri-
din-6-yl)ethanone,
4-(4-fluorophenyl)-1-methyl-5-({[6-(oxolane-3-carbonyl)-
5H,6H,7H-pyrrolo[3,4-b]pyridin-2-yl]oxy}methyl)-1H-
1,2,3-triazole,
1-(2-{[4-(4-fluorophenyl)-1-methyl-1H-1,2,3-triazol-5-yl]
methoxy}-5H,6H,7H-pyrrolo[3,4-b]pyridin-6-yl)-2-
methylpropan-1-one,
4-(4-fluorophenyl)-1-methyl-5-({[6-(oxolane-2-carbonyl)-
5H,6H,7H-pyrrolo[3,4-b]pyridin-2-yl]oxy}methyl)-1H-
1,2,3-triazole, 4-(4-fluorophenyl)-1-methyl-5-({[6-(oxane-3-carbonyl)-5H,6H,7H-pyrrolo[3,4-b]pyridin-2-yl]oxy}methyl)-1H-1,2,3-triazole,2-{[1-(4-fluorophenyl)-4-methyl-1H-1,2,3-triazol-5-yl]methoxy}-N-(1-methyl-5-oxopyrrolidin-3-yl)-5,6,7,8-tetrahydro-1,6-naphthyridine-6-carboxamide,
2-{[1-(4-fluorophenyl)-4-methyl-1H-1,2,3-triazol-5-yl]methoxy}-N,N-dimethyl-5,6,7,8-tetrahydro-1,6-naphthyridine-6-carboxamide,
2-{[1-(4-fluorophenyl)-4-methyl-1H-1,2,3-triazol-5-yl]methoxy}-6-(pyrrolidine-1-carbonyl)-5,6,7,8-tetrahydro-1,6-naphthyridine,
2-{[1-(4-fluorophenyl)-4-methyl-1H-1,2,3-triazol-5-yl]methoxy}-N-(oxolan-3-yl)-5,6,7,8-tetrahydro-1,6-naphthyridine-6-carboxamide,
N-(2-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide,
2-{[1-(4-fluorophenyl)-4-methyl-1H-1,2,3-triazol-5-yl]methoxy}-6-(morpholine-4-carbonyl)-5,6,7,8-tetrahydro-1,6-naphthyridine,
N-(4-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide,
2-{[3-(4-fluorophenyl)-5-methyl-1,2-oxazol-4-yl]methoxy}-6-(morpholine-4-carbonyl)-5,6,7,8-tetrahydro-1,6-naphthyridine,
2-{[3-(4-fluorophenyl)-5-methyl-1,2-oxazol-4-yl]methoxy}-N,N-dimethyl-5,6,7,8-tetrahydro-1,6-naphthyridine-6-carboxamide,
2-{[3-(4-fluorophenyl)-5-methyl-1,2-oxazol-4-yl]methoxy}-6-(pyrrolidine-1-carbonyl)-5,6,7,8-tetrahydro-1,6-naphthyridine,
2-{[3-(4-fluorophenyl)-5-methyl-1,2-oxazol-4-yl]methoxy}-6-(piperidine-1-carbonyl)-5,6,7,8-tetrahydro-1,6-naphthyridine, and
2-{[3-(4-fluorophenyl)-5-methyl-1,2-oxazol-4-yl]methoxy}-N-(oxolan-3-yl)-5,6,7,8-tetrahydro-1,6-naphthyridine-6-carboxamide.

In describing the general synthesis of the compounds of formula (I), the biological assays, the Intermediates and Examples, the following abbreviations have been used:
BOC=tert-butoxycarbonyl
Boc$_2$O=di-tert-butyl dicarbonate
DCM=dichloromethane
PBr$_3$=phosphorus tribromide
TFA=trifluoroacetic acid
DIPEA=N-ethyl-N-(propan-2-yl)propan-2-amine
BzOH=benzyl alchol
18-crown-6=1,4,7,10,13,16-hexaoxacyclooctadecane
Pd/C=palladium on carbon
AcCN=acetonitrile
triphosgene=bis(trichloromethyl)carbonate
Tris=2-amino-2-(hydroxymethyl)propane-1,3-diol
TLC=thin layer chromatography
brine=high-concentration solution of salt (usually sodium chloride)

The present invention also relates to the synthesis of compounds of formula (I). Several methods for preparing the compounds of this invention are illustrated in the following Schemes and Examples. Starting materials are purchased or made according to procedures known in the art or as illustrated herein.

Synthesis of intermediates of formula (III) is shown in Scheme 1, wherein A and R$^1$ are as defined in any of the embodiments described above for formula (I).

According to Scheme 1, reacting a compound of formula (II) in a suitable solvent, such as dichloromethane with a brominating agent, such as PBr$_3$ to give intermediates of formula (III). Hydroxy derivatives of formula (II) are known in the art (e.g. WO 2013/057123 A1, WO 2012/062623 A1) or can be synthesized by conventional methods.

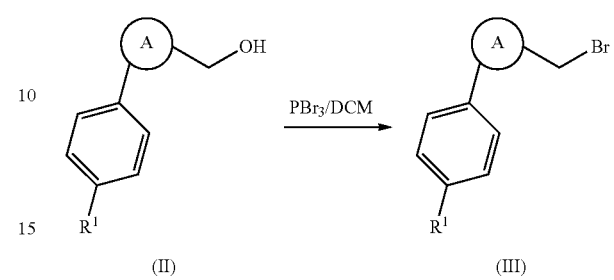

The reagents and detailed process steps required for the above reactions are set forth in the Intermediates.

Compounds of formula (I) can be synthesized according to Scheme 2, wherein A, R$^1$, R$^2$, n and m are as defined in any of the embodiments described above for formula (I).

According to Scheme 2, protection of commercially available bicyclic amine derivatives of formula (IV) provided the N—BOC amines of formula (V). The reaction can be carried out in the presence of BOC anhydride in dichloromethane using a base such as triethylamine. Treatment of chloro derivative of formula (V) with benzyl alcohol yielded the benzyl ether intermediate of formula (VI), followed by a palladium catalyst cleavage of benzyl ether of formula (VI) to obtain the desired hydroxy derivatives of formula (VII). Etherification between alcohols of formula (VII) and Intermediates of formula (III) can be accomplished in the presence of K$_2$CO$_3$ in acetonitrile to form ether derivative of formula (VIII). Deprotection of ether derivative of formula (VIII) using acid such as ethyl acetate saturated with hydrogen chloride or TFA in dichloromethane afforded the final intermediate of formula (IX). Finally, amine derivatives of formula (IX) can be acylated with R$^2$COCl of formula (X) in the presence of a base (Et$_3$N); or when R$^2$=NR$^4$R$^5$, amine derivatives of formula (IX) can be reacted with HNR$^4$R$^5$ of formula (XI) using triphosgene in the presence of a base (DIPEA) to form compound of formula (I). The acyl chlorides of formula (X) and amines of formula (XI) can be purchased or can be prepared by conventional methods, wherein the definition of R$^2$ is the same as described above for formula (I).

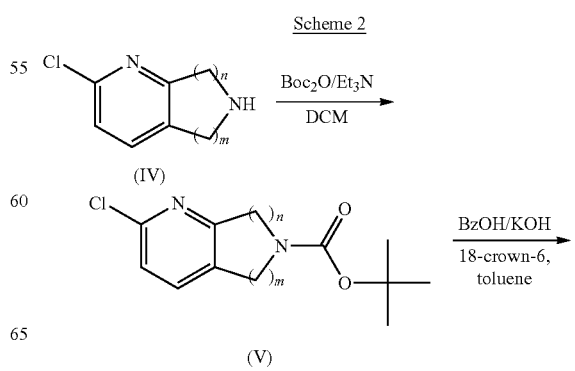

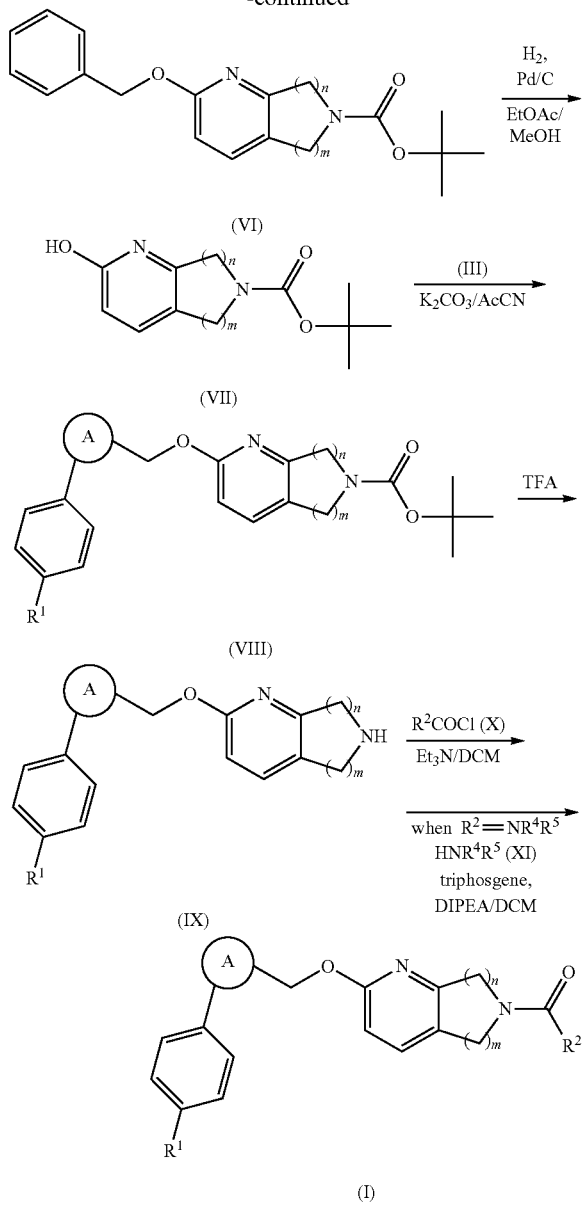

The reagents and detailed process steps required for the above reactions are set forth in the Examples.

The activity data of each of the compounds of formula (I) of the present invention are determined in vitro by the methods described below.

Biological Example 1: Binding Assay

The GABA$_A$ α5β3γ2 protein used for the receptor binding assay was derived from membranes produced from HEK cells (Millipore CYL3073) expressing the human recombinant GABA$_A$ α5β3γ2 receptor. Cells were stored and cultured in-house according to the instructions provided by the vendor (Millipor). Cell pellet was homogenized in 10 times modified Krebs Henseleit buffer (membrane preparation buffer): 20 mM Tris, 120 mM NaCl, 100 mM KCl, 25 mM CaCl$_2$) and 25 mM MgCl$_2$ pH=7.4 at 4° C. using Ultra Turrax (Janke&Kunkel) maximal speed for 15 seconds. The homogenate was centrifuged at 40,000 g for 30 minutes at 4° C. Supernatant was discarded and the resulting pellet was washed in membrane preparation buffer. Pellet was resuspended in membrane preparation buffer and aliquots of 1.4 mL ampulles were stored at −70° C. until use.

Receptor binding assays were performed in 96-well format in deep-well plates. For each 96-well plate one ampulle of membrane homogenate was thawed and diluted in binding buffer (50 mM Tris pH=7.4, 100 mM KCl) and 200 μL was dispensed into each well. Radioligand [$^3$H]Ro151788 (Perkin Elmer: NET757250UC) was prepared in binding buffer and added to each well in 50 μL volume to give final concentration of 0.5 nM. Test compounds in suitable concentration(s) were added in additional 50 μL. The final assay volume was 300 μL. Incubation was carried out for 60 minutes at 4° C. For non-specific binding 10 μM unlabeled diazepam was used. After incubation samples were filtered over UniFilter® GF/B™ using Filtermate Harvester (Perkin Elmer) and washed with 5×1 mL binding buffer. The plate was dried at 40° C. for an hour and 40 μL Microscint (Perkin Elmer) scintillation cocktail was added to each well. The plate was read in Microbeta (Perkin Elmer).

The specific radioligand binding (SB) was defined as the difference between total binding (Tot) and the non-specific binding (NSB). Results are expressed as a percent inhibition of specific binding obtained in the presence of compound of interest.

For IC$_{50}$ and K$_i$ determination a minimum of six drug concentrations in triplicate were used. IC$_{50}$ values (i.e. concentration of compound giving 50% inhibition of specific binding) were calculated from concentration-displacement curves by sigmoidal fitting using Origin 7.5 software. K$_i$ values (i.e. inhibition constants) were calculated using the Cheng-Prusoff equation K$_i$=IC$_{50}$/[1+(L/K$_D$)], where [L] is the radioligand concentration and K$_D$ the affinity of the labelled ligand for receptor. K$_D$ was determined from the Saturation analyses.

The compounds of the present invention were tested in the above described assay, and all were found to have high affinity for the GABA$_A$ α5 receptor (Ki<200 nM). Preferred are compounds with a Ki<50 nM.

Table 1 showing representative hGABA$_A$ α5 K$_i$ test results, obtained by the above described binding assay

| Ex. | hGABA$_A$ α5 K$_i$ (nM) |
| --- | --- |
| 1 | 2.8 |
| 2 | 7.0 |
| 3 | 5.0 |
| 4 | 16 |
| 5 | 7.8 |
| 6 | 2.7 |
| 7 | 6.8 |
| 8 | 3.7 |
| 9 | 6.2 |
| 10 | 21 |
| 11 | 11 |
| 12 | 14 |
| 13 | 4.3 |
| 14 | 28 |
| 15 | 42 |
| 16 | 42 |
| 17 | 69 |
| 18 | 50 |
| 19 | 49 |
| 20 | 24 |
| 21 | 35 |
| 22 | 57 |
| 23 | 45 |
| 24 | 46 |
| 25 | 29 |

| Ex. | hGABA$_A$ α5 K$_i$ (nM) |
|---|---|
| 26 | 80 |
| 27 | 137 |
| 28 | 43 |
| 29 | 18 |
| 30 | 82 |
| 31 | 44 |
| 32 | 22 |
| 33 | 14 |
| 34 | 112 |
| 35 | 71 |
| 36 | 9.8 |
| 37 | 69 |
| 38 | 18 |
| 39 | 24 |
| 40 | 56 |
| 41 | 67 |
| 42 | 13 |
| 43 | 30 |
| 44 | 54 |
| 45 | 3.2 |
| 46 | 84 |
| 47 | 7.2 |
| 48 | 33 |
| 49 | 1.2 |
| 50 | 0.8 |
| 51 | 31 |
| 52 | 37 |
| 53 | 11 |
| 54 | 5.3 |
| 55 | 13 |
| 56 | 17 |
| 57 | 14 |
| 58 | 13 |
| 59 | 31 |
| 60 | 1.2 |
| 61 | 4.8 |
| 62 | 5.7 |
| 63 | 9.5 |
| 64 | 25 |
| 65 | 28 |
| 66 | 59 |
| 67 | 20 |
| 68 | 7.5 |
| 69 | 25 |
| 70 | 9.2 |
| 71 | 56 |
| 72 | 29 |
| 73 | 18 |
| 74 | 46 |
| 75 | 38 |
| 76 | 30 |
| 77 | 66 |
| 78 | 28 |
| 79 | 108 |
| 80 | 38 |
| 81 | 37 |
| 82 | 5.2 |
| 83 | 3.8 |
| 84 | 8.9 |
| 85 | 36 |
| 86 | 6.5 |

Biological Example 2: Functional Assay

Human HEK293 cell lines expressing GABA$_A$ α1β3γ2 and GABA$_A$α5β3γ2 receptors were used in functional assays using the QPatch automated patch clamp system.

HEK293 cell lines stably expressing human recombinant GABA$_A$ α1β3γ2 receptor subunits (Millipore, CYL3073) or human recombinant GABA$_A$ α5β3γ2 receptor subunits (Millipore, CYL3053) were cultured in DMEM supplemented with 10% FBS (Gibco), passed two times per week and plated on Petri dishes previously coated with poly-d-lysine.

Automated whole-cell patch clamp recordings were made from cells 2-4 days after plating. Cells were detached using trypsin/EDTA (Sigma) treatment (2 minutes in 0.25% trypsin at 37° C.), then, after centrifugation (125 G, 3 min, 2×), resuspended in a serum-free based media (Gibco, CHO—S-SFM-II) containing 12.5 mM HEPES, 1× penicillin-streptomycin-amphotericin (SigmaMix) and soybean trypsin inhibitor (Sigma, 0.04 mg/ml).

Cell suspension, as well as the extracellular solution (130 mM NaCl, 5 mM KCl, 5.1 mM HEPES, 4.9 mM HEPES-Na, 10 mM CaCl$_2$), 2 mM MgCl$_2$, 10 mM glucose and 0.1% DMSO, pH=7.35-7.4) and the intracellular solution (80 mM KCl, 50 mM KF, 36 mM KOH, 10 mM EGTA, 10 mM HEPES, 1.75 mM MgCl$_2$, 0.5 mM CaCl$_2$), 4 mM Na$_2$ATP. 14 mM phosphocreatine, 50 U/ml creatine-phosphokinase, 0.3 mM GTP, pH=7.25-7.3) were added to the QPatch-HTX automated patch clamp system (Sophion) in single-cell mode at room temperature. Inward currents were evoked at a holding potential of −80 mV by 3-s-long applications of the control agonist GABA at sub-maximal effective concentration (1 µM) at 2-4-min intervals first in concentration-matched DMSO (0.1 or 0.3%) control solution for five times, then in the presence of the test compound for four times, finally in control solution again for three times (wash-out). At the end of the experiment 100 µM GABA was applied to saturate the GABA-response and to assess the efficacy of the control GABA application. Current signals were low-pass filtered at 100 Hz and recorded at a sampling rate of 1 kHz.

The percentage modulation was calculated from the comparison of GABA-evoked peak current amplitudes in the presence and absence of the test compound.

The compounds of the present invention were tested at 10 µM in the above described assay, and all were found to possess GABA$_A$ α5 negative allosteric modulator activity and selectivity for the α5 subtype over the α1. Preferred compounds have a functional efficacy at the α5 subtype of less than −20%.

Table 2 showing representative hGABA$_A$ α5 and hGABA$_A$ α1 functional efficacy test results, obtained by the above described assay:

| Ex. | hGABA$_A$ α5 efficacy (%) | hGABA$_A$ α1 efficacy (%) |
|---|---|---|
| 2 | −40 | −14 |
| 6 | −38 | −10 |
| 8 | −39 | −2 |
| 9 | −37 | −9 |
| 13 | −34 | −3 |
| 14 | −36 | 0 |
| 15 | −43 | −8 |
| 16 | −39 | −7 |
| 17 | −37 | −6 |
| 18 | −45 | −5 |
| 23 | −47 | −4 |
| 25 | −40 | −9 |
| 28 | −40 | −6 |
| 29 | −25 | −2 |
| 32 | −32 | −7 |
| 40 | −42 | −12 |
| 41 | −40 | −7 |
| 43 | −37 | −9 |
| 44 | −44 | −5 |
| 45 | −30 | −7 |
| 47 | −34 | −10 |
| 49 | −26 | −4 |
| 53 | −39 | −1 |
| 54 | −37 | −5 |
| 55 | −45 | −15 |

| Ex. | hGABA$_A$ α5 efficacy (%) | hGABA$_A$ α1 efficacy (%) |
|---|---|---|
| 56 | −40 | −14 |
| 58 | −40 | −21 |
| 60 | −27 | −8 |
| 61 | −41 | −20 |
| 62 | −34 | −23 |
| 63 | −34 | −16 |
| 64 | −39 | −12 |
| 65 | −41 | −22 |
| 75 | −35 | −3 |
| 78 | −34 | −3 |

The present invention will be further illustrated by the following Intermediates and Examples without limiting the scope of the present invention to them. From the above description and from the Intermediates and Examples, the person skilled in the art may ascertain the essential features of the invention and without departing from its essence and scope, may make certain changes and modifications in order to adapt the invention to various applications and conditions. As a result, the invention is not limited to the following illustrative examples, but rather to the scope determined by the appended claims.

In general, the compounds of formula (I) can be prepared according to the common general knowledge of the person skilled in the art and/or the methods described for the working examples and/or intermediates. Solvents, temperatures, pressures and other reaction conditions can be easily selected by the person skilled in the art. Starting materials are commercially available and/or can be easily prepared by the person skilled in the art according to literature procedure. During the preparation of compounds combinatorial techniques can be used, for example, where intermediates are suitable for the use of these methods.

Intermediate 1

4-(bromomethyl)-3-(4-fluorophenyl)-5-methyl-1,2-oxazole

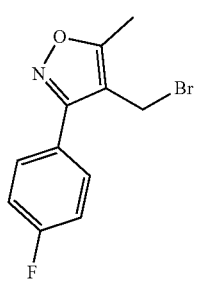

4.98 g (24.0 mmol) of [3-(4-fluorophenyl)-5-methyl-1,2-oxazol-4-yl]methanol (WO 2013/057123 A1, Hoffmann-La Roche) was dissolved in 80 mL of anhydrous dichloromethane, and 9.76 g (3.39 mL, 36.1 mmol) of phosphorus tribromide was added dropwise to the stirred solution. The reaction mixture was stirred for 1 hour at room temperature, and poured into 50 mL of saturated sodium bicarbonate solution. The mixture was stirred for another 10 minutes, and the phases were separated. The organic phase was washed with water, dried over anhydrous sodium sulfate, and evaporated to afford 5.89 g (97%) of the title compound as a yellow-brownish solid. MS (ESI) m/z: 269.9 [M+H]$^+$.

Intermediate 2

5-(bromomethyl)-1-(4-fluorophenyl)-4-methyl-1H-1,2,3-triazole

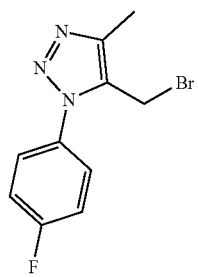

In analogy of Intermediate 1, [1-(4-fluorophenyl)-4-methyl-1H-1,2,3-triazol-5-yl]methanol (WO 2012/062623 A1, Hoffmann-La Roche) was converted into the title compound (114 mg, 87%) which was obtained as a clear oil. The compound is unstable and slowly decomposes upon standing; therefore, it was generated in situ in the etherification reaction step.

Intermediate 3

5-(bromomethyl)-1-(4-chlorophenyl)-4-methyl-1H-1,2,3-triazole

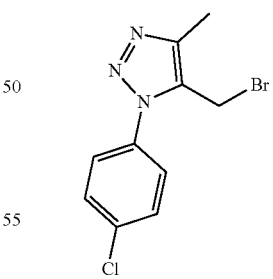

In analogy of Intermediate 1, [1-(4-chlorophenyl)-4-methyl-1H-1,2,3-triazol-5-yl]methanol (WO 2012/062623 A1, Hoffmann-La Roche) was converted into the title compound (210 mg, 81.7%) which was obtained as a clear oil. The compound is unstable and slowly decomposes upon standing; therefore, it was generated in situ in the etherification reaction step.

Intermediate 4

5-(bromomethyl)-4-(4-fluorophenyl)-1-methyl-1H-1,2,3-triazole

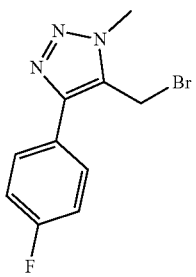

In analogy of Intermediate 1, [4-(4-fluorophenyl)-1-methyl-1H-1,2,3-triazol-5-yl]methanol (WO 2012/062623 A1, Hoffmann-La Roche) was converted into the title compound (55 mg, 73%) which was obtained as a clear oil. The compound is unstable and slowly decomposes upon standing; therefore, it was generated in situ in the etherification reaction step.

Intermediate 5

5-(bromomethyl)-4-(4-chlorophenyl)-1-methyl-1H-1,2,3-triazole

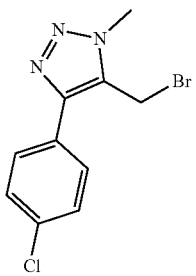

In analogy of Intermediate 1, [4-(4-chlorophenyl)-1-methyl-1H-1,2,3-triazol-5-yl]methanol (WO 2012/062623 A1, Hoffmann-La Roche) was converted into the title compound (120 mg, 85%) which was obtained as a clear oil. The compound is unstable and slowly decomposes upon standing; therefore, it was generated in situ in the etherification reaction step.

Example 1

1-[2-{[3-(4-fluorophenyl)-5-methyl-1,2-oxazol-4-yl]methoxy}-7,8-dihydro-1,6-naphthyridin-6(5H)-yl]ethanone

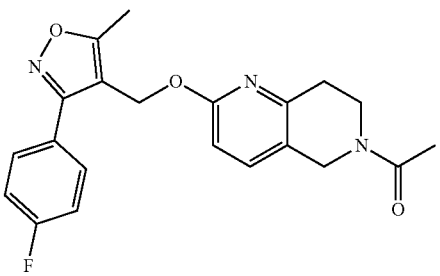 [SMILES: CC(=O)N1CCc2nc(OCc3c(-c4ccc(F)cc4)noc3C)ccc2C1]

a.: tert-butyl 2-chloro-7,8-dihydro-1,6-naphthyridine-6(5H)-carboxylate (WO 2013/079452 A1, Hoffmann-La Roche)
To a slurry of commercially available 10.0 g (59.3 mmol) of 2-chloro-5,6,7,8-tetrahydro-1,6-naphthyridine hydrochloride and 6.6 g (9.0 mL, 65.0 mmol) of triethylamine in 150 mL of DCM a solution of 14.2 g (65.0 mmol) of di-tert-butyl dicarbonate in 10 mL of DCM was added dropwise via an addition funnel within 15 min. The resulting solution was stirred at room temperature for 2 hours and monitored using TLC (cyclohexane-ethyl acetataé 1:1 as eluent). Upon completion, the reaction mixture was concentrated. The residue was dissolved in 50 mL of ethyl acetate and washed three times with 30 mL of water, 30 mL of brine, and dried over $MgSO_4$. The solvent was evaporated under reduced pressure to give the title compound as an off-white solid. Yield: 15.4 g (97%). MS (ESI) m/z: 269.1 $[M+H]^+$.

b.: tert-butyl 2-(benzyloxy)-7,8-dihydro-1,6-naphthyridine-6(5H)-carboxylate (WO 2016/107832 A1, Hoffmann-La Roche)
To an ice-cooled solution of 15.0 g (55.8 mmol) of tert-butyl 2-chloro-7,8-dihydro-1,6-naphthyridine-6(5H)-carboxylate in 150 mL of toluene 9.4 g (167.4 mmol) of solid potassium hydroxide was added followed by 30 minutes of stirring and then dropwise addition of a solution of 8.7 mL (83.7 mmol) of benzyl alcohol in 150 mL of toluene. Then, 1.5 g (5.58 mmol) of solid 18-crown-6 was added and the reaction mixture was stirred at 130° C. overnight. After cooling, filtration of inorganics and concentration of the filtrate under reduced pressure afforded the residue which was purified by flash chromatography on silica gel (cyclohexane-ethyl acetate, 10:1 as eluent). The title compound was obtained as a white solid. Yield: 10.5 g (55.4%). MS (ESI) m/z: 341.1 $[M+H]^+$.

c.: tert-butyl 2-oxo-1,5,7,8-tetrahydro-1,6-naphthyridine-6(2H)-carboxylate (WO 2016/107832 A1, Hoffmann-La Roche)
A solution of 4.0 g (11.7 mmol) of tert-butyl 2-(benzyloxy)-7,8-dihydro-1,6-naphthyridine-6(5H)-carboxylate in 500 mL ethylacetate and 150 mL of methanol was stirred under nitrogen atmosphere till the mixture became a clear solution. Pd/C catalyst (10% w/w, 200 mg) was added and hydrogen gas bubbled trough the reaction mixture for 3.5 hours. After completion, monitored by TLC (chloroform-methanol 10:1 as eluent), the catalyst was filtered off and the filtrate concentrated under reduced pressure to give the crude product. After recrystallization from dietyl ether, title compound was isolated as a white solid. Yield: 2.6 g (89.0%). MS (ESI) m/z: 251.1 [M+H]$^+$.

d.: tert-butyl 2-{[3-(4-fluorophenyl)-5-methyl-1,2-oxazol-4-yl]methoxy}-5,6,7,8-tetrahydro-1,6-naphthyridine-6-carboxylate 9.10 g (33.7 mmol) of 4-(bromomethyl)-3-(4-fluorophenyl)-5-methyl-1,2-oxazole, and 8.43 g (33.7 mmol) of tert-butyl 2-oxo-1,5,7,8-tetrahydro-1,6-naphthyridine-6(2H)-carboxylate were dissolved in 100 mL of anhydrous acetonitrile. Then, 9.31 g (67.4 mmol) of anhydrous potassium-carbonate was added to the solution, and the suspension was stirred under reflux for 5 hours. The conversion was followed by TLC (DCM:MeOH=20:1 as eluent, silica plate). After the reaction completed, the mixture was filtered, and evaporated to give 15.6 g of oily crude product, which was further purified by flash column chromatography (silica gel, eluent: DCM:MeOH, 0-5% gradient). Yield: 11.6 g (77%) glassy solid. MS (ESI) m/z: 440.3 [M+H]$^+$.

e.: 2-{[3-(4-fluorophenyl)-5-methyl-1,2-oxazol-4-yl]methoxy}-5,6,7,8-tetrahydro-1,6-naphthyridine 11.5 g (26.2 mmol) of tert-butyl 2-{[3-(4-fluorophenyl)-5-methyl-1,2-oxazol-4-yl]methoxy}-5,6,7,8-tetrahydro-1,6-naphthyridine-6-carboxylate was dissolved in 200 mL of ethyl acetate. 180 mL of ethyl acetate saturated with hydrogen chloride was added dropwise to the solution. The reaction mixture was stirred for 15 minutes at room temperature. The white precipitate formed was filtered out, washed with small portion of ethyl acetate, and dried in vacuum-exsiccator giving 10.2 g of white, crystalline solid. MS (ESI) m/z: 340.2 [M+H]$^+$. The crude compound was used without purification.

f.: 1-[2-{[3-(4-fluorophenyl)-5-methyl-1,2-oxazol-4-yl]methoxy}-7,8-dihydro-1,6-naphthyridin-6(5H)-yl]ethanone 7.63 g (22.5 mmol) of 2-{[3-(4-fluorophenyl)-5-methyl-1,2-oxazol-4-yl]methoxy}-5,6,7,8-tetrahydro-1,6-naphthyridine was dissolved in 100 mL of anhydrous dichloromethane. 6.83 g (9.4 mL, 67.4 mmol) of anhydrous triethyl amine was added in one portion to the solution, and the reaction mixture was cooled with an ice-water bath. A solution of 1.60 mL (1.76 g, 22.5 mmol) of acetyl chloride in 20 mL of anhydrous dichloromethane was added dropwise to the stirred reaction mixture during 10 minutes. The cooling bath was removed, and the mixture was allowed to warm up to room temperature. The conversion was checked by TLC (DCM:MeOH=10:1 or cyclohexane:EtOAc=1:3 as eluent, silica plate). The reaction mixture was washed with saturated sodium hydrogen carbonate solution and with water, dried over anhydrous sodium sulfate, and evaporated. 10.4 g residue was obtained, which was purified by flash coloumn chromatography (silica gel, eluent: cyclohexane:EtOAc 40-80% gradient). Yield: 6.28 g (64%), white, amorphous solid identical to the title compound. MS (ESI) m/z: 404.1 [M+Na]$^+$.

Table 3 showing cornpounds synthesized according to Scheme 2:

TABLE 3

| Ex. | Structure | MS m/z | Name |
|---|---|---|---|
| 2 | 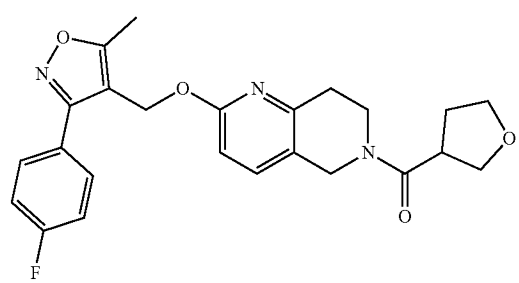 [SMILES: Cc1onc(-c2ccc(F)cc2)c1COc1ccc2c(n1)CCN(C(=O)C1CCOC1)C2] | 438.2 [M + H]$^+$ | 2-{[3-(4-fluorophenyl)-5-methyl-1,2-oxazol-4-yl]methoxy}-6-(oxolane-3-carbonyl)-5,6,7,8-tetrahydro-1,6-naphthyridine |
| 3 | 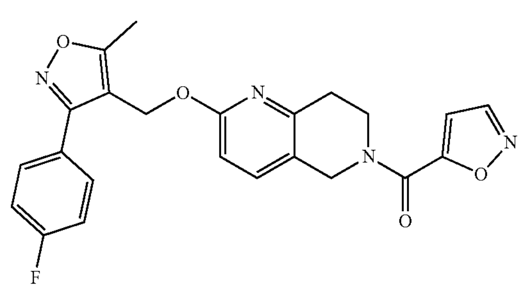 [SMILES: Cc1onc(-c2ccc(F)cc2)c1COc1ccc2c(n1)CCN(C(=O)c1ccno1)C2] | 435.1 [M + H]$^+$ | 2-{[3-(4-fluorophenyl)-5-methyl-1,2-oxazol-4-yl]methoxy}-6-(1,2-oxazole-5-carbonyl)-5,6,7,8-tetrahydro-1,6-naphthyridine |

TABLE 3-continued showing compounds synthesized according to Scheme 2:

| Ex. | Structure | MS m/z | Name |
|---|---|---|---|
| 4 | 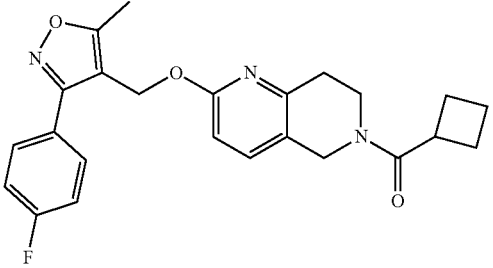 [SMILES: Cc1onc(-c2ccc(F)cc2)c1COc1ccc2c(n1)CCN(C(=O)C1CCC1)C2] | 422.1 [M + H]+ | 6-cyclobutanecarbonyl-2-{[3-(4-fluorophenyl)-5-methyl-1,2-oxazol-4-yl]methoxy}-5,6,7,8-tetrahydro-1,6-naphthyridine |
| 5 | 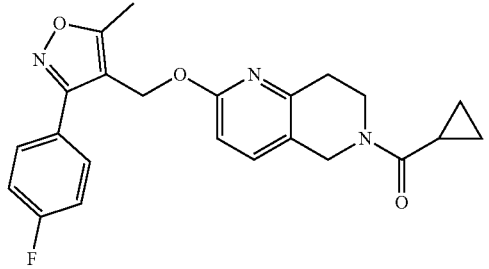 [SMILES: Cc1onc(-c2ccc(F)cc2)c1COc1ccc2c(n1)CCN(C(=O)C1CC1)C2] | 408.1 [M + H]+ | 6-cyclopropanecarbonyl-2-{[3-(4-fluorophenyl)-5-methyl-1,2-oxazol-4-yl]methoxy}-5,6,7,8-tetrahydro-1,6-naphthyridine |
| 6 | 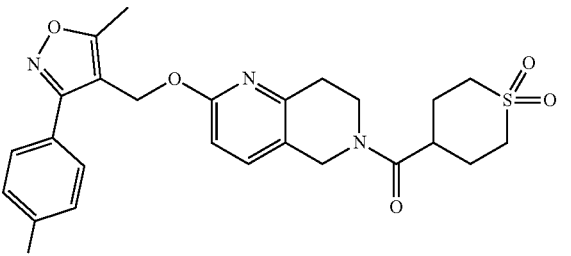 | 522.1 [M + Na]+ | 4-(2-{[3-(4-fluorophenyl)-5-methyl-1,2-oxazol-4-yl]methoxy}-5,6,7,8-tetrahydro-1,6-naphthyridine-6-carbonyl)-1lambda6-thiane-1,1-dione |
| 7 | 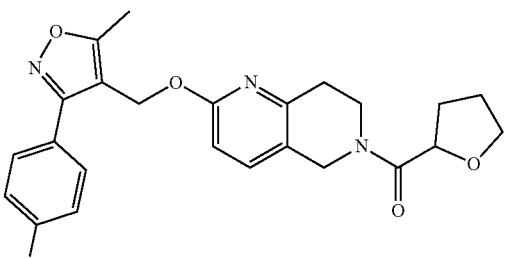 | 460.2 [M + Na]+ | 2-{[3-(4-fluorophenyl)-5-methyl-1,2-oxazol-4-yl]methoxy}-6-(oxolane-2-carbonyl)-5,6,7,8-tetrahydro-1,6-naphthyridine |
| 8 | 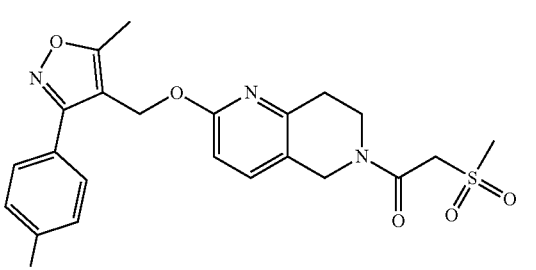 | 460.1 [M + H]+ | 1-(2-{[3-(4-fluorophenyl)-5-methyl-1,2-oxazol-4-yl]methoxy}-5,6,7,8-tetrahydro-1,6-naphthyridin-6-yl)-2-methanesulfonylethan-1-one |

TABLE 3-continued showing compounds synthesized according to Scheme 2:

| Ex. | Structure | MS m/z | Name |
|---|---|---|---|
| 9 | 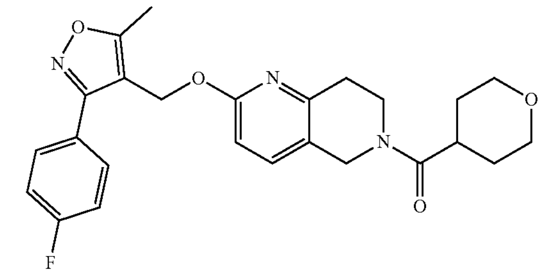 [SMILES: Cc1onc(-c2ccc(F)cc2)c1COc1ccc2c(n1)CCN(C(=O)C1CCOCC1)C2] | 474.1 [M + Na]⁺ | 2-{[3-(4-fluorophenyl)-5-methyl-1,2-oxazol-4-yl]methoxy}-6-(oxane-4-carbonyl)-5,6,7,8-tetrahydro-1,6-naphthyridine |
| 10 | 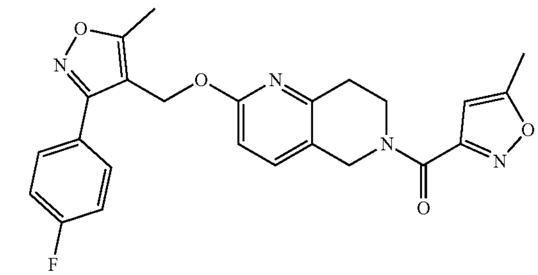 [SMILES: Cc1cc(C(=O)N2CCc3nc(OCc4c(-c5ccc(F)cc5)noc4C)ccc3C2)no1] | 471.1 [M + Na]⁺ | 2-{[3-(4-fluorophenyl)-5-methyl-1,2-oxazol-4-yl]methoxy}-6-(5-methyl-1,2-oxazole-3-carbonyl)-5,6,7,8-tetrahydro-1,6-naphthyridine |
| 11 | 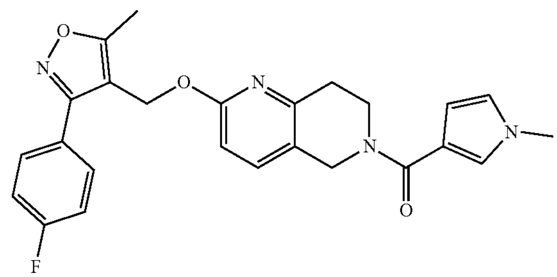 [SMILES: Cc1onc(-c2ccc(F)cc2)c1COc1ccc2c(n1)CCN(C(=O)c1ccn(C)c1)C2] | 447.2 [M + H]⁺ | 2-{[3-(4-fluorophenyl)-5-methyl-1,2-oxazol-4-yl]methoxy}-6-(1-methyl-1H-pyrrole-3-carbonyl)-5,6,7,8-tetrahydro-1,6-naphthyridine |
| 12 | 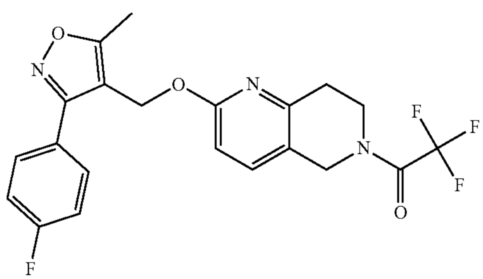 [SMILES: Cc1onc(-c2ccc(F)cc2)c1COc1ccc2c(n1)CCN(C(=O)C(F)(F)F)C2] | 436.3 [M + H]⁺ | 2,2,2-trifluoro-1-(2-{[3-(4-fluorophenyl)-5-methyl-1,2-oxazol-4-yl]methoxy}-5,6,7,8-tetrahydro-1,6-naphthyridin-6-yl)ethan-1-one |
| 13 | 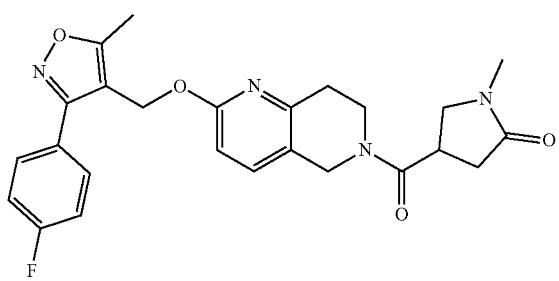 [SMILES: Cc1onc(-c2ccc(F)cc2)c1COc1ccc2c(n1)CCN(C(=O)C1CC(=O)N(C)C1)C2] | 465.1 [M + H]⁺ | 4-(2-{[3-(4-fluorophenyl)-5-methyl-1,2-oxazol-4-yl]methoxy}-5,6,7,8-tetrahydro-1,6-naphthyridine-6-carbonyl)-1-methylpyrrolidin-2-one |

TABLE 3-continued showing compounds synthesized according to Scheme 2:

| Ex. | Structure | MS m/z | Name |
|---|---|---|---|
| 14 | 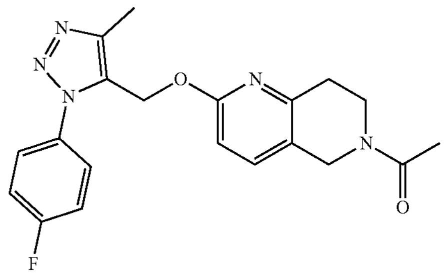 [SMILES: CC(=O)N1CCc2nc(OCc3c(C)nnn3-c3ccc(F)cc3)ccc2C1] | 382.2 [M + H]⁺ | 1-(2-{[1-(4-fluorophenyl)-4-methyl-1H-1,2,3-triazol-5-yl]methoxy}-5,6,7,8-tetrahydro-1,6-naphthyridin-6-yl)ethan-1-one |
| 15 | 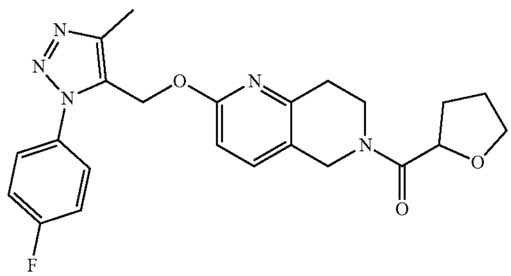 [SMILES: Cc1nnn(-c2ccc(F)cc2)c1COc1ccc2c(n1)CCN(C(=O)C1CCCO1)C2] | 438.1 [M + H]⁺ | 2-{[1-(4-fluorophenyl)-4-methyl-1H-1,2,3-triazol-5-yl]methoxy}-6-(oxolane-2-carbonyl)-5,6,7,8-tetrahydro-1,6-naphthyridine |
| 16 | 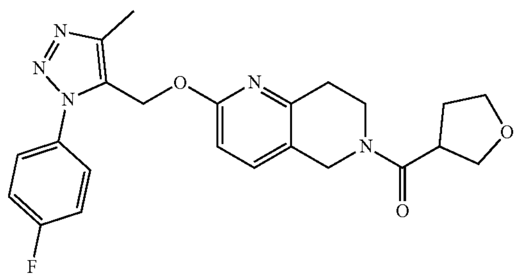 [SMILES: Cc1nnn(-c2ccc(F)cc2)c1COc1ccc2c(n1)CCN(C(=O)C1CCOC1)C2] | 438.1 [M + H]⁺ | 2-{[1-(4-fluorophenyl)-4-methyl-1H-1,2,3-triazol-5-yl]methoxy}-6-(oxolane-3-carbonyl)-5,6,7,8-tetrahydro-1,6-naphthyridine |
| 17 | 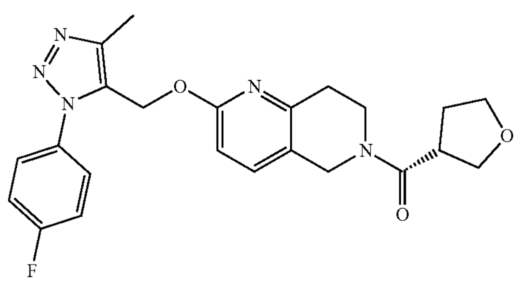 | 438.1 [M + H]⁺ | 2-{[1-(4-fluorophenyl)-4-methyl-1H-1,2,3-triazol-5-yl]methoxy}-6-[(3R)-oxolane-3-carbonyl]-5,6,7,8-tetrahydro-1,6-naphthyridine |
| 18 | 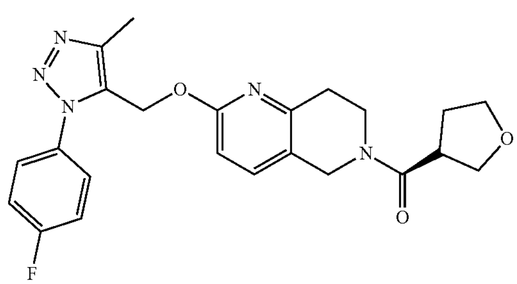 | 438.1 [M + H]⁺ | 2-{[1-(4-fluorophenyl)-4-methyl-1H-1,2,3-triazol-5-yl]methoxy}-6-[(3S)-oxolane-3-carbonyl]-5,6,7,8-tetrahydro-1,6-naphthyridine |

TABLE 3-continued showing compounds synthesized according to Scheme 2:

| Ex. | Structure | MS m/z | Name |
| --- | --- | --- | --- |
| 19 | 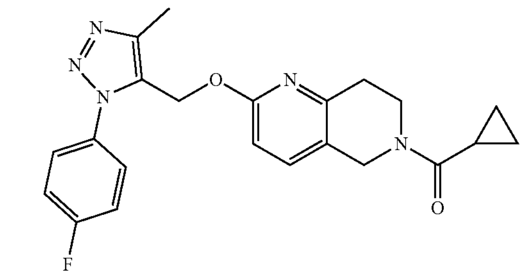 [SMILES: Cc1nnn(-c2ccc(F)cc2)c1COc1ccc2c(n1)CCN(C(=O)C1CC1)C2] | 408.1 [M + H]⁺ | 6-cyclopropanecarbonyl-2-{[1-(4-fluorophenyl)-4-methyl-1H-1,2,3-triazol-5-yl]methoxy}-5,6,7,8-tetrahydro-1,6-naphthyridine |
| 20 | 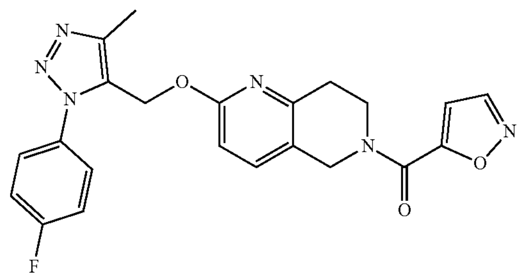 [SMILES: Cc1nnn(-c2ccc(F)cc2)c1COc1ccc2c(n1)CCN(C(=O)c1ccno1)C2] | 435.1 [M + H]⁺ | 2-{[1-(4-fluorophenyl)-4-methyl-1H-1,2,3-triazol-5-yl]methoxy}-6-(1,2-oxazole-5-carbonyl)-5,6,7,8-tetrahydro-1,6-naphthyridine |
| 21 | 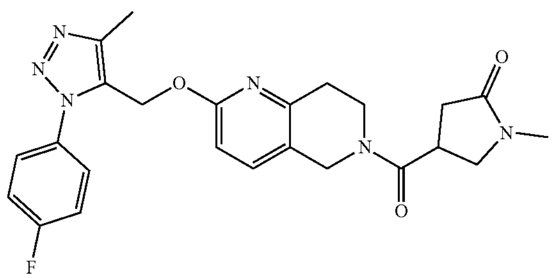 [SMILES: Cc1nnn(-c2ccc(F)cc2)c1COc1ccc2c(n1)CCN(C(=O)C1CC(=O)N(C)C1)C2] | 465.1 [M + H]⁺ | 4-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one |
| 22 | 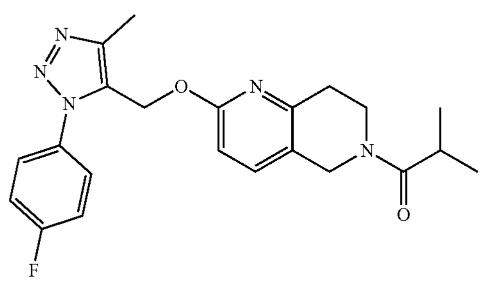 [SMILES: Cc1nnn(-c2ccc(F)cc2)c1COc1ccc2c(n1)CCN(C(=O)C(C)C)C2] | 410.1 [M + H]⁺ | 1-(2-{[1-(4-fluorophenyl)-4-methyl-1H-1,2,3-triazol-5-yl]methoxy}-5,6,7,8-tetrahydro-1,6-naphthyridin-6-yl)-2-methylpropan-1-one |
| 23 | 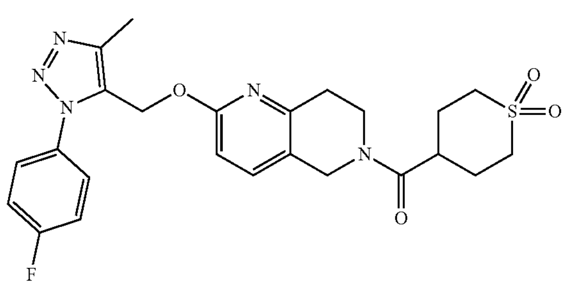 [SMILES: Cc1nnn(-c2ccc(F)cc2)c1COc1ccc2c(n1)CCN(C(=O)C1CCS(=O)(=O)CC1)C2] | 500.1 [M + H]⁺ | 4-(2-{[1-(4-fluorophenyl)-4-methyl-1H-1,2,3-triazol-5-yl]methoxy}-5,6,7,8-tetrahydro-1,6-naphthyridine-6-carbonyl)-1lambda6-thiane-1,1-dione |

TABLE 3-continued showing compounds synthesized according to Scheme 2:

| Ex. | Structure | MS m/z | Name |
|---|---|---|---|
| 24 | 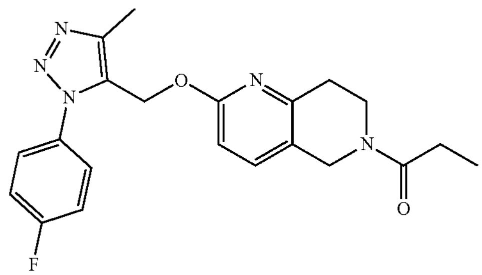 [SMILES: CCC(=O)N1CCc2nc(OCc3c(C)nnn3-c3ccc(F)cc3)ccc2C1] | 396.3 [M + H]⁺ | 1-(2-{[1-(4-fluorophenyl)-4-methyl-1H-1,2,3-triazol-5-yl]methoxy}-5,6,7,8-tetrahydro-1,6-naphthyridin-6-yl)propan-1-one |
| 25 | 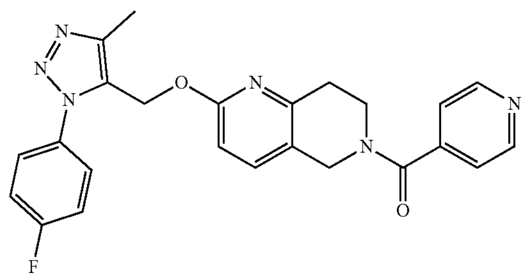 [SMILES: Cc1nnn(-c2ccc(F)cc2)c1COc1ccc2c(n1)CCN(C(=O)c1ccncc1)C2] | 445.4 [M + H]⁺ | 2-{[1-(4-fluorophenyl)-4-methyl-1H-1,2,3-triazol-5-yl]methoxy}-6-(pyridine-4-carbonyl)-5,6,7,8-tetrahydro-1,6-naphthyridine |
| 26 | 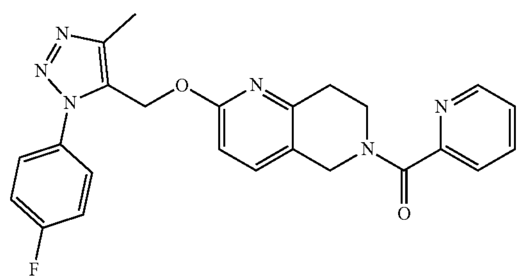 [SMILES: Cc1nnn(-c2ccc(F)cc2)c1COc1ccc2c(n1)CCN(C(=O)c1ccccn1)C2] | 445.3 [M + H]⁺ | 2-{[1-(4-fluorophenyl)-4-methyl-1H-1,2,3-triazol-5-yl]methoxy}-6-(pyridine-2-carbonyl)-5,6,7,8-tetrahydro-1,6-naphthyridine |
| 27 | 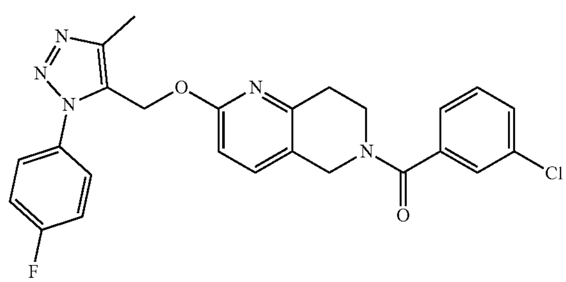 [SMILES: Cc1nnn(-c2ccc(F)cc2)c1COc1ccc2c(n1)CCN(C(=O)c1cccc(Cl)c1)C2] | 478.3 [M + H]⁺ | 6-(3-chlorobenzoyl)-2-{[1-(4-fluorophenyl)-4-methyl-1H-1,2,3-triazol-5-yl]methoxy}-5,6,7,8-tetrahydro-1,6-naphthyridine |
| 28 | 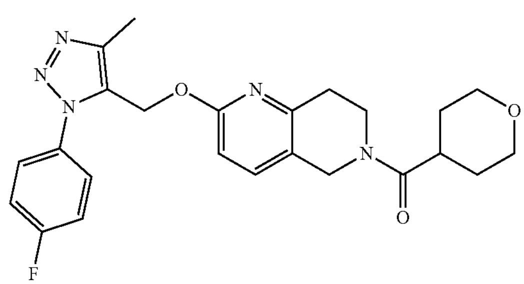 [SMILES: Cc1nnn(-c2ccc(F)cc2)c1COc1ccc2c(n1)CCN(C(=O)C1CCOCC1)C2] | 452.1 [M + H]⁺ | 2-{[1-(4-fluorophenyl)-4-methyl-1H-1,2,3-triazol-5-yl]methoxy}-6-(oxane-4-carbonyl)-5,6,7,8-tetrahydro-1,6-naphthyridine |

TABLE 3-continued showing compounds synthesized according to Scheme 2:

| Ex. | Structure | MS m/z | Name |
|---|---|---|---|
| 29 | 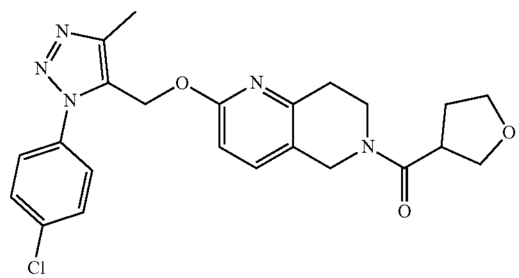 | 438.1 [M + H]+ | 2-{[1-(4-chlorophenyl)-4-methyl-1H-1,2,3-triazol-5-yl]methoxy}-6-(oxolane-3-carbonyl)-5,6,7,8-tetrahydro-1,6-naphthyridine |
| 30 | 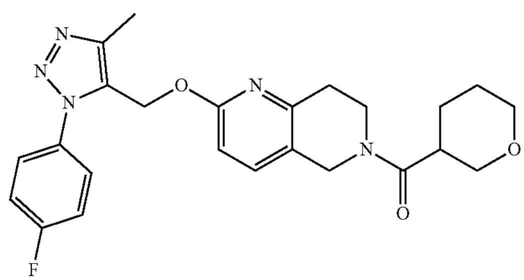 [SMILES: Cc1nnn(-c2ccc(F)cc2)c1COc1ccc2c(n1)CCN(C(=O)C1CCCOC1)C2] | 452.2 [M + H]+ | 2-{[1-(4-fluorophenyl)-4-methyl-1H-1,2,3-triazol-5-yl]methoxy}-6-(oxane-3-carbonyl)-5,6,7,8-tetrahydro-1,6-naphthyridine |
| 31 | 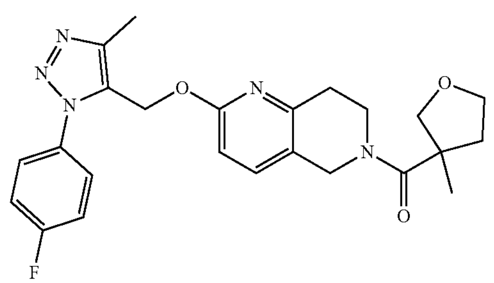 [SMILES: Cc1nnn(-c2ccc(F)cc2)c1COc1ccc2c(n1)CCN(C(=O)C1(C)CCOC1)C2] | 452.1 [M + H]+ | 2-{[1-(4-fluorophenyl)-4-methyl-1H-1,2,3-triazol-5-yl]methoxy}-6-(3-methyloxolane-3-carbonyl)-5,6,7,8-tetrahydro-1,6-naphthyridine |
| 32 | 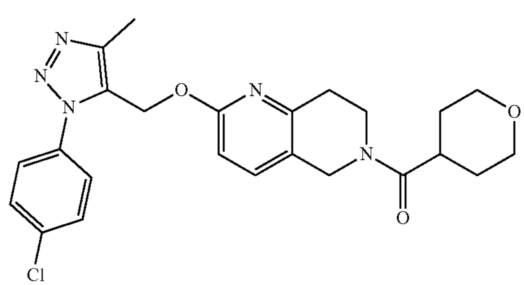 [SMILES: Cc1nnn(-c2ccc(Cl)cc2)c1COc1ccc2c(n1)CCN(C(=O)C1CCOCC1)C2] | 468.2 [M + H]+ | 2-{[1-(4-chlorophenyl)-4-methyl-1H-1,2,3-triazol-5-yl]methoxy}-6-(oxane-4-carbonyl)-5,6,7,8-tetrahydro-1,6-naphthyridine |
| 33 | 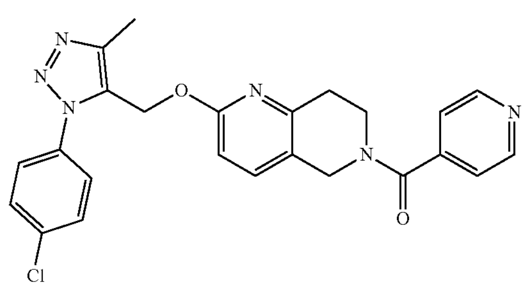 | 461.2 [M + H]+ | 2-{[1-(4-chlorophenyl)-4-methyl-1H-1,2,3-triazol-5-yl]methoxy}-6-(pyridine-4-carbonyl)-5,6,7,8-tetrahydro-1,6-naphthyridine |

TABLE 3-continued showing compounds synthesized according to Scheme 2:

| Ex. | Structure | MS m/z | Name |
|---|---|---|---|
| 34 | 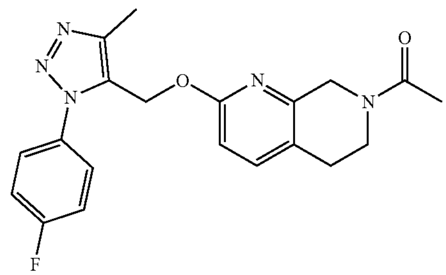 [SMILES: CC(=O)N1CCc2ccc(OCc3c(C)nnn3-c3ccc(F)cc3)nc2C1] | 382.2 [M + H]⁺ | 1-(2-{[1-(4-fluorophenyl)-4-methyl-1H-1,2,3-triazol-5-yl]methoxy}-5,6,7,8-tetrahydro-1,7-naphthyridin-7-yl)ethan-1-one |
| 35 | 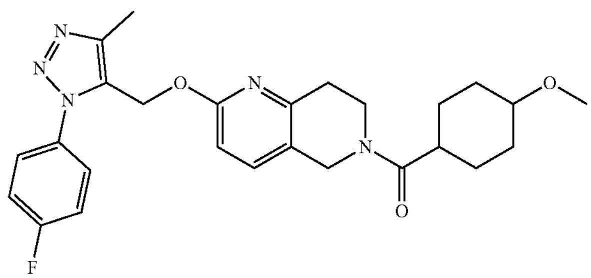 [SMILES: COC1CCC(C(=O)N2CCc3nc(OCc4c(C)nnn4-c4ccc(F)cc4)ccc3C2)CC1] | 480.3 [M + H]⁺ | 2-{[1-(4-fluorophenyl)-4-methyl-1H-1,2,3-triazol-5-yl]methoxy}-6-(4-methoxycyclohexanecarbonyl)-5,6,7,8-tetrahydro-1,6-naphthyridine |
| 36 | 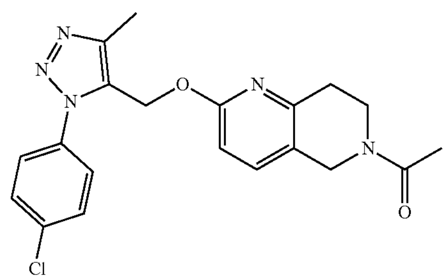 [SMILES: CC(=O)N1CCc2nc(OCc3c(C)nnn3-c3ccc(Cl)cc3)ccc2C1] | 398.1 [M + H]⁺ | 1-(2-{[1-(4-chlorophenyl)-4-methyl-1H-1,2,3-triazol-5-yl]methoxy}-5,6,7,8-tetrahydro-1,6-naphthyridin-6-yl)ethan-1-one |
| 37 | 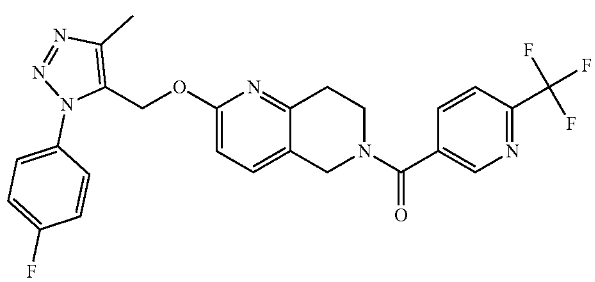 [SMILES: Cc1nnn(-c2ccc(F)cc2)c1COc1ccc2c(n1)CCN(C(=O)c1ccc(C(F)(F)F)nc1)C2] | 513.2 [M + H]⁺ | 2-{[1-(4-fluorophenyl)-4-methyl-1H-1,2,3-triazol-5-yl]methoxy}-6-[6-(trifluoromethyl)pyridine-3-carbonyl]-5,6,7,8-tetrahydro-1,6-naphthyridine |
| 38 | 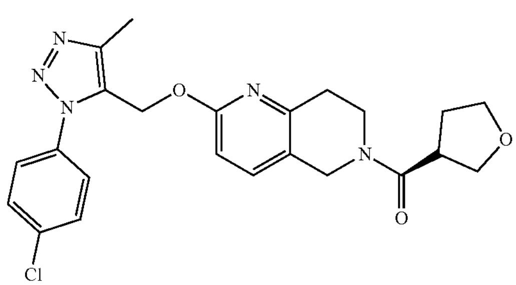 | 454.1 [M + H]⁺ | 2-{[1-(4-chlorophenyl)-4-methyl-1H-1,2,3-triazol-5-yl]methoxy}-6-[(3S)-oxolane-3-carbonyl]-5,6,7,8-tetrahydro-1,6-naphthyridine |

TABLE 3-continued showing compounds synthesized according to Scheme 2:

| Ex. | Structure | MS m/z | Name |
| --- | --- | --- | --- |
| 39 | 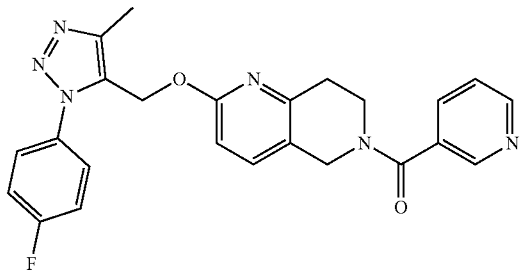 [SMILES: Cc1nnn(-c2ccc(F)cc2)c1COc1ccc2c(n1)CCN(C(=O)c1cccnc1)C2] | 445.2 [M + H]⁺ | 2-{[1-(4-fluorophenyl)-4-methyl-1H-1,2,3-triazol-5-yl]methoxy}-6-(pyridine-3-carbonyl)-5,6,7,8-tetrahydro-1,6-naphthyridine |
| 40 | 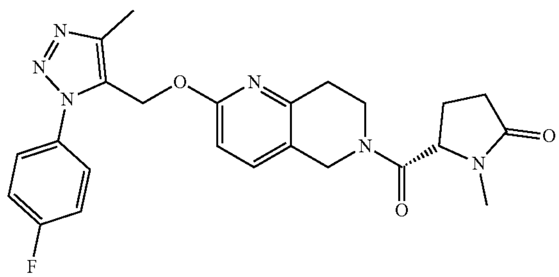 | 465.2 [M + H]⁺ | (5S)-5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one |
| 41 | 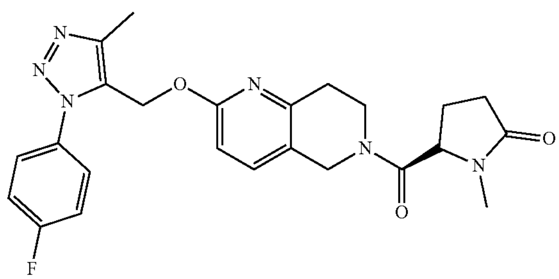 | 465.2 [M + H]⁺ | (5R)-5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one |
| 42 | 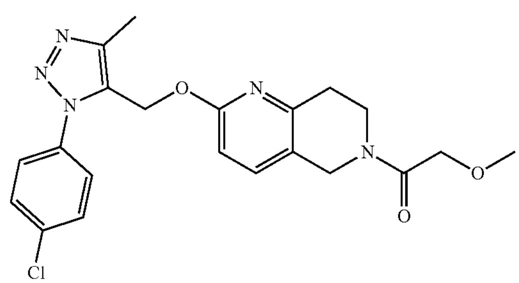 [SMILES: COCC(=O)N1CCc2nc(OCc3c(C)nnn3-c3ccc(Cl)cc3)ccc2C1] | 428.1 [M + H]⁺ | 1-(2-{[1-(4-chlorophenyl)-4-methyl-1H-1,2,3-triazol-5-yl]methoxy}-5,6,7,8-tetrahydro-1,6-naphthyridin-6-yl)-2-methoxyethan-1-one |
| 43 | 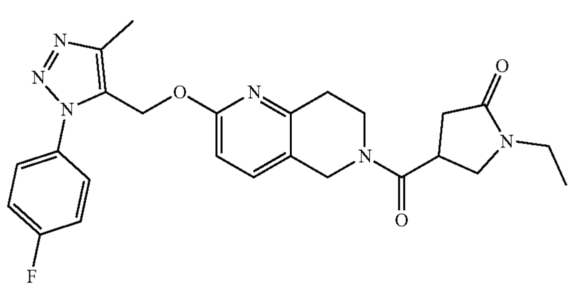 [SMILES: CCN1CC(C(=O)N2CCc3nc(OCc4c(C)nnn4-c4ccc(F)cc4)ccc3C2)CC1=O] | 479.2 [M + H]⁺ | 1-ethyl-4-(2-{[1-(4-fluorophenyl)-4-methyl-1H-1,2,3-triazol-5-yl]methoxy}-5,6,7,8-tetrahydro-1,6-naphthyridine-6-carbonyl)pyrrolidin-2-one |

TABLE 3-continued showing compounds synthesized according to Scheme 2:

| Ex. | Structure | MS m/z | Name |
|---|---|---|---|
| 44 | 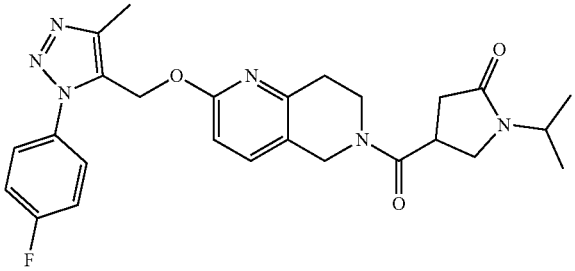 [SMILES: Cc1nnn(-c2ccc(F)cc2)c1COc1ccc2c(n1)CCN(C(=O)C1CC(=O)N(C(C)C)C1)C2] | 493.2 [M + H]+ | 4-(2-{[1-(4-fluorophenyl)-4-methyl-1H-1,2,3-triazol-5-yl]methoxy}-5,6,7,8-tetrahydro-1,6-naphthyridine-6-carbonyl)-1-(propan-2-yl)pyrrolidin-2-one |
| 45 | 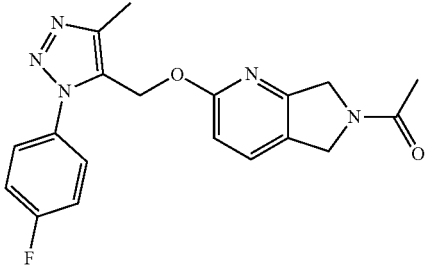 [SMILES: CC(=O)N1Cc2ccc(OCc3c(C)nnn3-c3ccc(F)cc3)nc2C1] | 368.2 [M + H]+ | 1-(2-{[1-(4-fluorophenyl)-4-methyl-1H-1,2,3-triazol-5-yl]methoxy}-5H,6H,7H-pyrrolo[3,4-b]pyridin-6-yl)ethan-1-one |
| 46 | 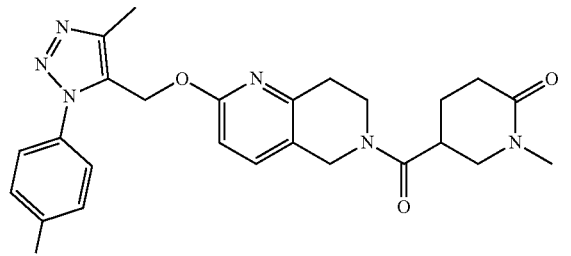 | 479.1 [M + H]+ | 5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpiperidin-2-one |
| 47 | 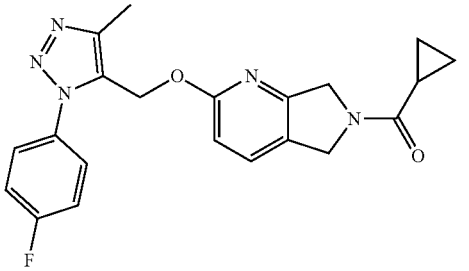 [SMILES: Cc1nnn(-c2ccc(F)cc2)c1COc1ccc2c(n1)CN(C(=O)C1CC1)C2] | 394.1 [M + H]+ | cyclopropyl(2-{[1-(4-fluorophenyl)-4-methyl-1H-1,2,3-triazol-5-yl]methoxy}-5,7-dihydro-6H-pyrrolo[3,4-b]pyridin-6-yl)methanone |
| 48 | 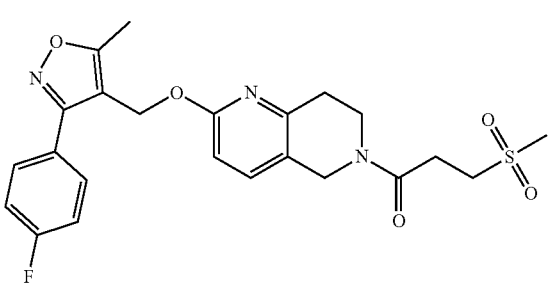 [SMILES: Cc1onc(-c2ccc(F)cc2)c1COc1ccc2c(n1)CCN(C(=O)CCS(C)(=O)=O)C2] | 474.2 [M + H]+ | 1-(2-{[3-(4-fluorophenyl)-5-methyl-1,2-oxazol-4-yl]methoxy}-5,6,7,8-tetrahydro-1,6-naphthyridin-6-yl)-3-methanesulfonylpropan-1-one |

TABLE 3-continued showing compounds synthesized according to Scheme 2:

| Ex. | Structure | MS m/z | Name |
| --- | --- | --- | --- |
| 49 | 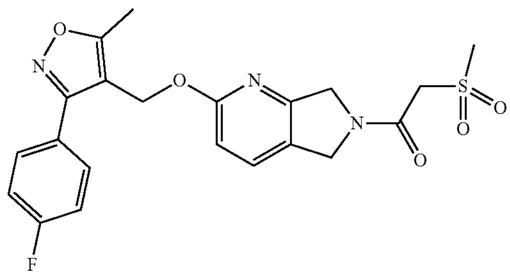 [SMILES: Cc1onc(-c2ccc(F)cc2)c1COc1ccc2c(n1)CN(C(=O)CS(C)(=O)=O)C2] | 446.1 [M + H]⁺ | 1-(2-{[3-(4-fluorophenyl)-5-methyl-1,2-oxazol-4-yl]methoxy}-5H,6H,7H-pyrrolo[3,4-b]pyridin-6-yl)-2-methanesulfonylethan-1-one |
| 50 | 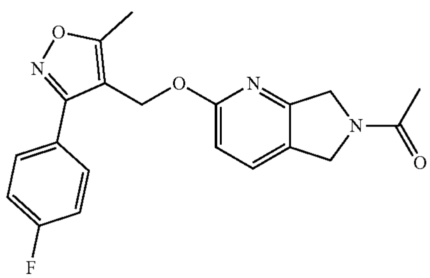 [SMILES: CC(=O)N1Cc2ccc(OCc3c(-c4ccc(F)cc4)noc3C)nc2C1] | 390.1 [M + Na]⁺ | 1-(2-{[3-(4-fluorophenyl)-5-methyl-1,2-oxazol-4-yl]methoxy}-5,7-dihydro-6H-pyrrolo[3,4-b]pyridin-6-yl)ethanone |
| 51 | 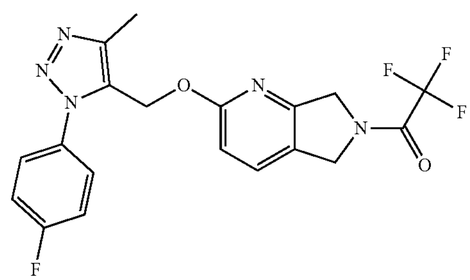 | 410.1 [M + H]⁺ | 2,2,2-trifluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone |
| 52 | 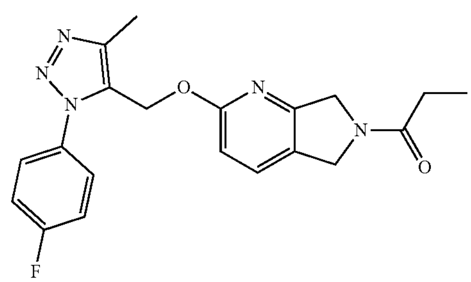 [SMILES: CCC(=O)N1Cc2ccc(OCc3c(C)nnn3-c3ccc(F)cc3)nc2C1] | 382.1 [M + H]⁺ | 1-(2-{[1-(4-fluorophenyl)-4-methyl-1H-1,2,3-triazol-5-yl]methoxy}-5,7-dihydro-6H-pyrrolo[3,4-b]pyridin-6-yl)propan-1-one |
| 53 | 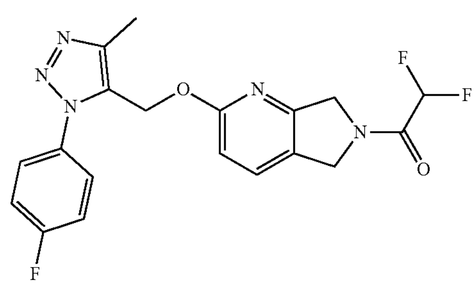 [SMILES: Cc1nnn(-c2ccc(F)cc2)c1COc1ccc2c(n1)CN(C(=O)C(F)F)C2] | 404.1 [M + H]⁺ | 2,2-difluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone |

TABLE 3-continued showing compounds synthesized according to Scheme 2:

| Ex. | Structure | MS m/z | Name |
| --- | --- | --- | --- |
| 54 | 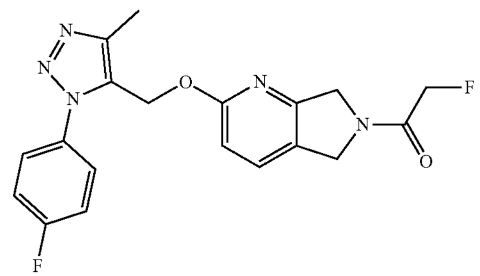 [SMILES: Cc1nnn(-c2ccc(F)cc2)c1COc1ccc2c(n1)CN(C(=O)CF)C2] | 386.1 [M + H]⁺ | 2-fluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone |
| 55 | 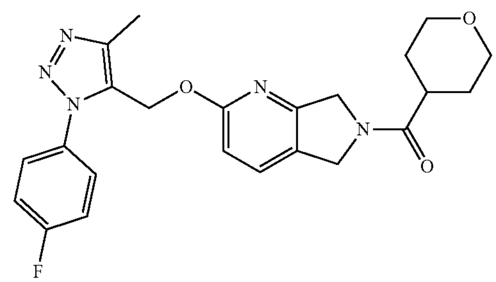 [SMILES: Cc1nnn(-c2ccc(F)cc2)c1COc1ccc2c(n1)CN(C(=O)C1CCOCC1)C2] | 438.1 [M + H]⁺ | 1-(4-fluorophenyl)-4-methyl-5-({[6-(oxane-4-carbonyl)-5H,6H,7H-pyrrolo[3,4-b]pyridin-2-yl]oxy}methyl)-1H-1,2,3-triazole |
| 56 | 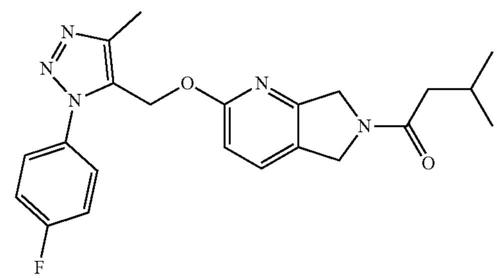 [SMILES: Cc1nnn(-c2ccc(F)cc2)c1COc1ccc2c(n1)CN(C(=O)CC(C)C)C2] | 410.1 [M + H]⁺ | 1-(2-{[1-(4-fluorophenyl)-4-methyl-1H-1,2,3-triazol-5-yl]methoxy}-5H,6H,7H-pyrrolo[3,4-b]pyridin-6-yl)-3-methylbutan-1-one |
| 57 | 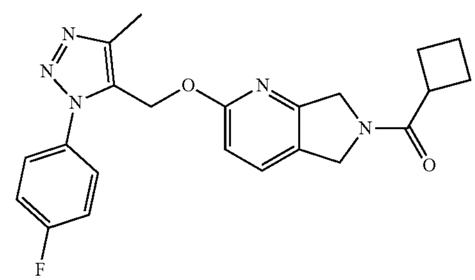 [SMILES: Cc1nnn(-c2ccc(F)cc2)c1COc1ccc2c(n1)CN(C(=O)C1CCC1)C2] | 408.1 [M + H]⁺ | 5-[({6-cyclobutanecarbonyl-5H,6H,7H-pyrrolo[3,4-b]pyridin-2-yl}oxy)methyl]-1-(4-fluorophenyl)-4-methyl-1H-1,2,3-triazole |
| 58 | 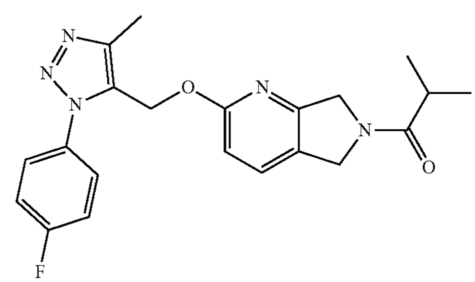 [SMILES: Cc1nnn(-c2ccc(F)cc2)c1COc1ccc2c(n1)CN(C(=O)C(C)C)C2] | 396.1 [M + H]⁺ | 1-(2-{[1-(4-fluorophenyl)-4-methyl-1H-1,2,3-triazol-5-yl]methoxy}-5H,6H,7H-pyrrolo[3,4-b]pyridin-6-yl)-2-methylpropan-1-one |

TABLE 3-continued showing compounds synthesized according to Scheme 2:

| Ex. | Structure | MS m/z | Name |
| --- | --- | --- | --- |
| 59 | 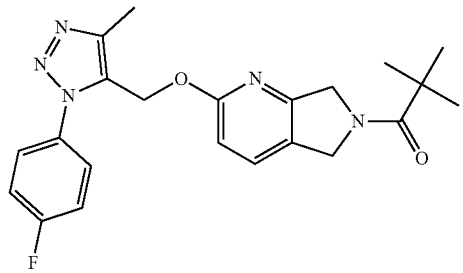 [SMILES: Cc1nnn(-c2ccc(F)cc2)c1COc1ccc2c(n1)CN(C(=O)C(C)(C)C)C2] | 410.1 [M + H]⁺ | 1-(2-{[1-(4-fluorophenyl)-4-methyl-1H-1,2,3-triazol-5-yl]methoxy}-5H,6H,7H-pyrrolo[3,4-b]pyridin-6-yl)-2,2-dimethylpropan-1-one |
| 60 | 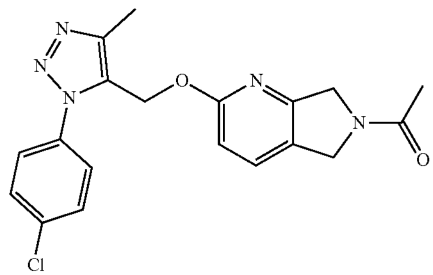 [SMILES: CC(=O)N1Cc2ccc(OCc3c(C)nnn3-c3ccc(Cl)cc3)nc2C1] | 384.1 [M + H]⁺ | 1-(2-{[1-(4-chlorophenyl)-4-methyl-1H-1,2,3-triazol-5-yl]methoxy}-5,7-dihydro-6H-pyrrolo[3,4-b]pyridin-6-yl)ethanone |
| 61 | 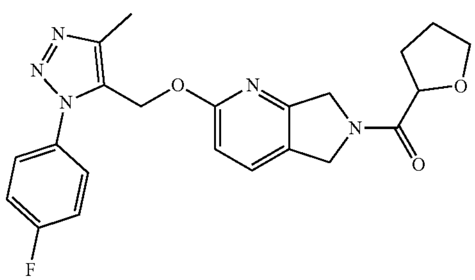 [SMILES: Cc1nnn(-c2ccc(F)cc2)c1COc1ccc2c(n1)CN(C(=O)C1CCCO1)C2] | 424.2 [M + H]⁺ | 1-(4-fluorophenyl)-4-methyl-5-({[6-(oxolane-2-carbonyl)-5H,6H,7H-pyrrolo[3,4-b]pyridin-2-yl]oxy}methyl)-1H-1,2,3-triazole |
| 62 | 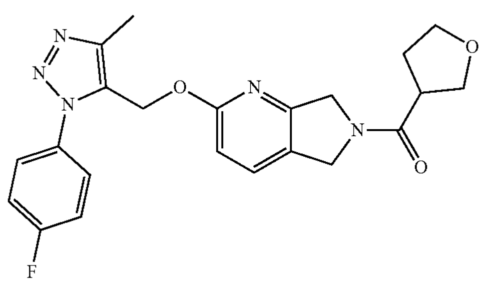 [SMILES: Cc1nnn(-c2ccc(F)cc2)c1COc1ccc2c(n1)CN(C(=O)C1CCOC1)C2] | 424.2 [M + H]⁺ | 1-(4-fluorophenyl)-4-methyl-5-({[6-(oxolane-3-carbonyl)-5H,6H,7H-pyrrolo[3,4-b]pyridin-2-yl]oxy}methyl)-1H-1,2,3-triazole |
| 63 | 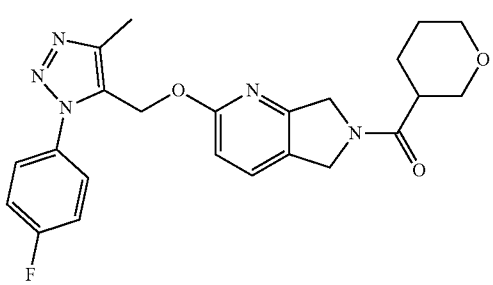 [SMILES: Cc1nnn(-c2ccc(F)cc2)c1COc1ccc2c(n1)CN(C(=O)C1CCCOC1)C2] | 438.2 [M + H]⁺ | 1-(4-fluorophenyl)-4-methyl-5-({[6-(oxane-3-carbonyl)-5H,6H,7H-pyrrolo[3,4-b]pyridin-2-yl]oxy}methyl)-1H-1,2,3-triazole |

TABLE 3-continued showing compounds synthesized according to Scheme 2:

| Ex. | Structure | MS m/z | Name |
|---|---|---|---|
| 64 | 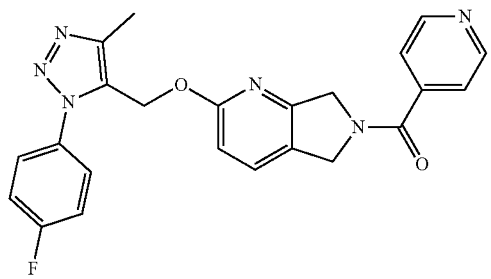 [SMILES: Cc1nnn(-c2ccc(F)cc2)c1COc1ccc2c(n1)CN(C(=O)c1ccncc1)C2] | 431.2 [M + H]+ | 4-(2-{[1-(4-fluorophenyl)-4-methyl-1H-1,2,3-triazol-5-yl]methoxy}-5H,6H,7H-pyrrolo[3,4-b]pyridine-6-carbonyl)pyridine |
| 65 | 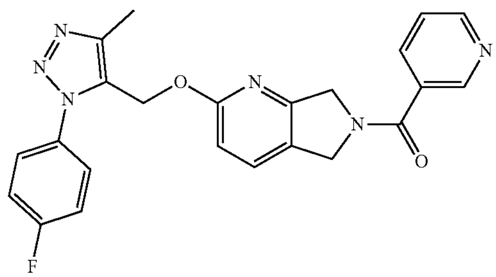 [SMILES: Cc1nnn(-c2ccc(F)cc2)c1COc1ccc2c(n1)CN(C(=O)c1cccnc1)C2] | 431.2 [M + H]+ | 3-(2-{[1-(4-fluorophenyl)-4-methyl-1H-1,2,3-triazol-5-yl]methoxy}-5H,6H,7H-pyrrolo[3,4-b]pyridine-6-carbonyl)pyridine |
| 66 | 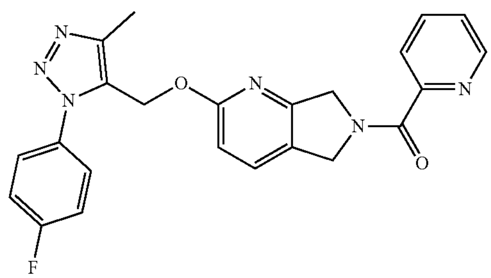 [SMILES: Cc1nnn(-c2ccc(F)cc2)c1COc1ccc2c(n1)CN(C(=O)c1ccccn1)C2] | 431.2 [M + H]+ | 2-(2-{[1-(4-fluorophenyl)-4-methyl-1H-1,2,3-triazol-5-yl]methoxy}-5H,6H,7H-pyrrolo[3,4-b]pyridine-6-carbonyl)pyridine |
| 67 | 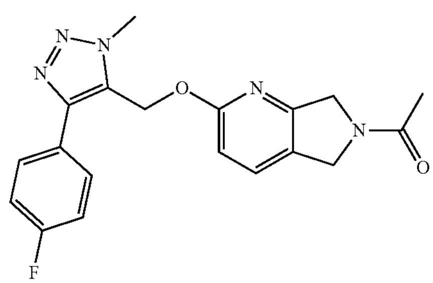 [SMILES: CC(=O)N1Cc2ccc(OCc3c(-c4ccc(F)cc4)nnn3C)nc2C1] | 368.2 [M + H]+ | 1-(2-{[4-(4-fluorophenyl)-1-methyl-1H-1,2,3-triazol-5-yl]methoxy}-5,7-dihydro-6H-pyrrolo[3,4-b]pyridin-6-yl)ethanone |
| 68 | 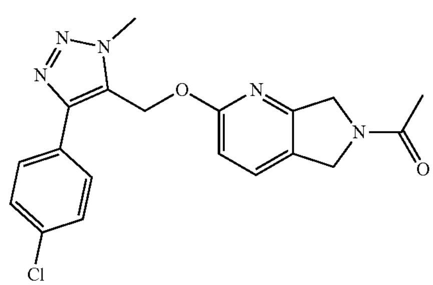 [SMILES: CC(=O)N1Cc2ccc(OCc3c(-c4ccc(Cl)cc4)nnn3C)nc2C1] | 384.1 [M + H]+ | 1-(2-{[4-(4-chlorophenyl)-1-methyl-1H-1,2,3-triazol-5-yl]methoxy}-5,7-dihydro-6H-pyrrolo[3,4-b]pyridin-6-yl)ethanone |

TABLE 3-continued showing compounds synthesized according to Scheme 2:

| Ex. | Structure | MS m/z | Name |
|---|---|---|---|
| 69 | 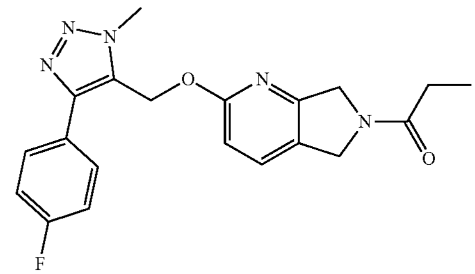 [SMILES: CCC(=O)N1Cc2ccc(OCc3c(-c4ccc(F)cc4)nnn3C)nc2C1] | 382.1 [M + H]⁺ | 1-(2-{[4-(4-fluorophenyl)-1-methyl-1H-1,2,3-triazol-5-yl]methoxy}-5,7-dihydro-6H-pyrrolo[3,4-b]pyridin-6-yl)propan-1-one |
| 70 | 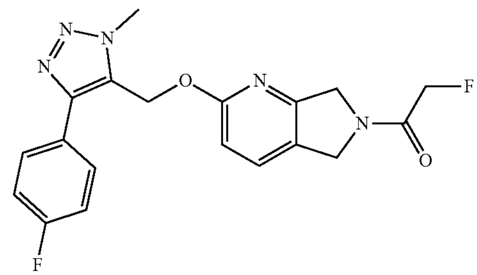 [SMILES: Cn1nnc(-c2ccc(F)cc2)c1COc1ccc2c(n1)CN(C(=O)CF)C2] | 386.1 [M + H]⁺ | 2-fluoro-1-(2-{[4-(4-fluorophenyl)-1-methyl-1H-1,2,3-triazol-5-yl]methoxy}-5,7-dihydro-6H-pyrrolo[3,4-b]pyridin-6-yl)ethanone |
| 71 | 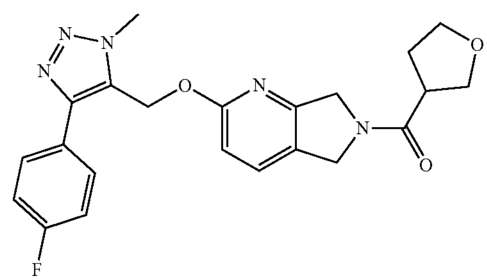 [SMILES: Cn1nnc(-c2ccc(F)cc2)c1COc1ccc2c(n1)CN(C(=O)C1CCOC1)C2] | 424.2 [M + H]⁺ | 4-(4-fluorophenyl)-1-methyl-5-({[6-(oxolane-3-carbonyl)-5H,6H,7H-pyrrolo[3,4-b]pyridin-2-yl]oxy}methyl)-1H-1,2,3-triazole |
| 72 | 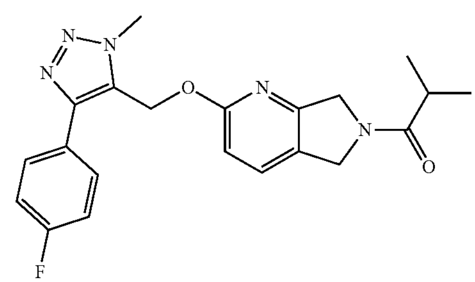 [SMILES: CC(C)C(=O)N1Cc2ccc(OCc3c(-c4ccc(F)cc4)nnn3C)nc2C1] | 396.1 [M + H]⁺ | 1-(2-{[4-(4-fluorophenyl)-1-methyl-1H-1,2,3-triazol-5-yl]methoxy}-5H,6H,7H-pyrrolo[3,4-b]pyridin-6-yl)-2-methylpropan-1-one |
| 73 | 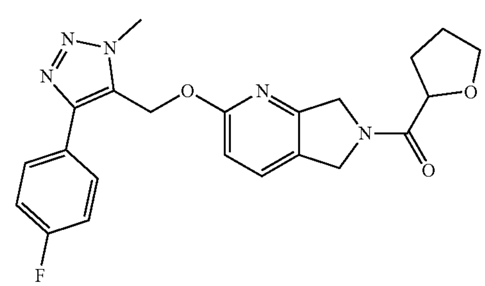 [SMILES: Cn1nnc(-c2ccc(F)cc2)c1COc1ccc2c(n1)CN(C(=O)C1CCCO1)C2] | 424.2 [M + H]⁺ | 4-(4-fluorophenyl)-1-methyl-5-({[6-(oxolane-2-carbonyl)-5H,6H,7H-pyrrolo[3,4-b]pyridin-2-yl]oxy}methyl)-1H-1,2,3-triazole |

TABLE 3-continued showing compounds synthesized according to Scheme 2:

| Ex. | Structure | MS m/z | Name |
|---|---|---|---|
| 74 | 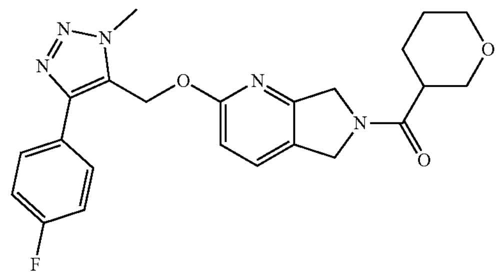 [SMILES: Cn1nnc(-c2ccc(F)cc2)c1COc1ccc2c(n1)CN(C(=O)C1CCCOC1)C2] | 438.2 [M + H]⁺ | 4-(4-fluorophenyl)-1-methyl-5-({[6-(oxane-3-carbonyl)-5H,6H,7H-pyrrolo[3,4-b]pyridin-2-yl]oxy}methyl)-1H-1,2,3-triazole |

Example 75

2-{[1-(4-fluorophenyl)-4-methyl-1H-1,2,3-triazol-5-yl]methoxy}-N-(1-methyl-5-oxopyrrolidin-3-yl)-5,6,7,8-tetrahydro-1,6-naphthyridine-6-carboxamide

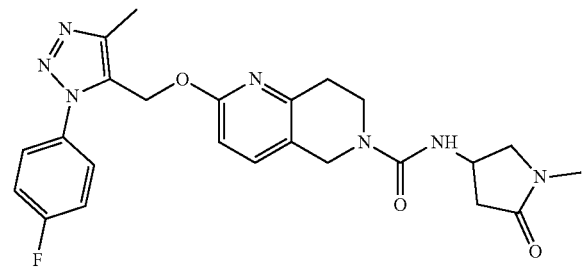 [SMILES: Cc1nnn(-c2ccc(F)cc2)c1COc1ccc2c(n1)CCN(C(=O)NC1CC(=O)N(C)C1)C2]

To a solution of 284 mg (2.49 mmol) of 4-amino-1-methylpyrrolidin-2-one in 30 mL of anhydrous dichloromethane 704 mg (0.95 mL, 5.45 mmol) of N,N-diisopropylethylamine was added in one portion, and the reaction mixture was cooled with an ice-water bath, then 296 mg (0.998 mmol) of bis(trichloromethyl)carbonate was added in one portion. The so obtained solution was stirred for 30 minutes, then 757 mg (2.23 mmol) of 2-{[3-(4-fluorophenyl)-5-methyl-1,2-oxazol-4-yl]methoxy}-5,6,7,8-tetrahydro-1,6-naphthyridine in 10 mL of anhydrous dichloromethane was added dropwise to the stirred reaction mixture during 5 minutes. The cooling bath was removed, and the mixture was allowed to warm up to room temperature and stirred for 8 hours. The reaction mixture was washed with saturated sodium hydrogen carbonate solution and with water, dried over anhydrous sodium sulfate, and evaporated. The obtained residue was purified by flash coloumn chromatography (silica gel, eluent: 100% DCM→80% DCM:20% MeOH (35 min)). Yield: 338 mg (32%), white, amorphous solid identical to the title compound. MS (ESI) m/z: 480.2 [M+H]⁺.

Table 4 showing compounds synthesized according to Example 75

TABLE 4 showing compounds synthesized according to Example 75:

| Ex. | Structure | MS m/z | Name |
|---|---|---|---|
| 76 | 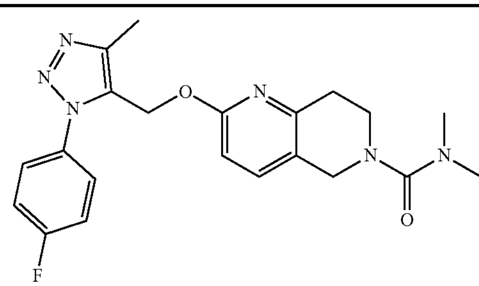 | 411.2 [M + H]⁺ | 2-{[1-(4-fluorophenyl)-4-methyl-1H-1,2,3-triazol-5-yl]methoxy}-N,N-dimethyl-5,6,7,8-tetrahydro-1,6-naphthyridine-6-carboxamide |
| 77 | 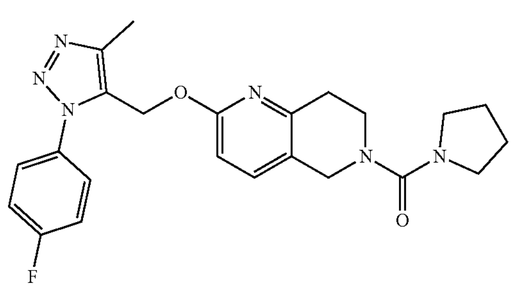 [SMILES: Cc1nnn(-c2ccc(F)cc2)c1COc1ccc2c(n1)CCN(C(=O)N1CCCC1)C2] | 437.2 [M + H]⁺ | 2-{[1-(4-fluorophenyl)-4-methyl-1H-1,2,3-triazol-5-yl]methoxy}-6-(pyrrolidine-1-carbonyl)-5,6,7,8-tetrahydro-1,6-naphthyridine |

TABLE 4-continued showing compounds synthesized according to Example 75:

| Ex. | Structure | MS m/z | Name |
| --- | --- | --- | --- |
| 78 | 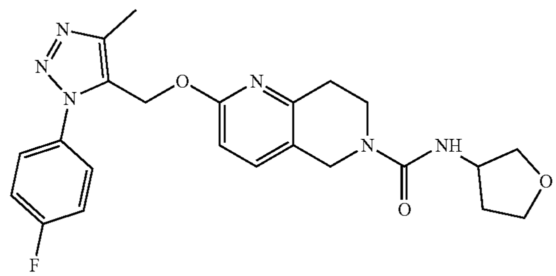 [SMILES: Cc1nnn(-c2ccc(F)cc2)c1COc1ccc2c(n1)CCN(C(=O)NC1CCOC1)C2] | 453.2 [M + H]⁺ | 2-{[1-(4-fluorophenyl)-4-methyl-1H-1,2,3-triazol-5-yl]methoxy}-N-(oxolan-3-yl)-5,6,7,8-tetrahydro-1,6-naphthyridine-6-carboxamide |
| 79 | 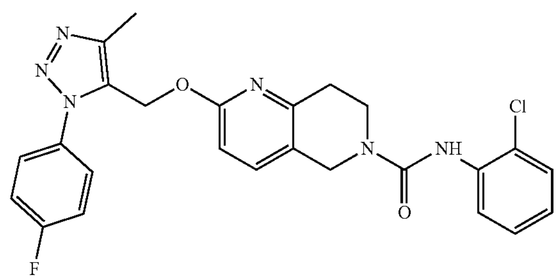 [SMILES: Cc1nnn(-c2ccc(F)cc2)c1COc1ccc2c(n1)CCN(C(=O)Nc1ccccc1Cl)C2] | 492.9 [M + H]⁺ | N-(2-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide |
| 80 | 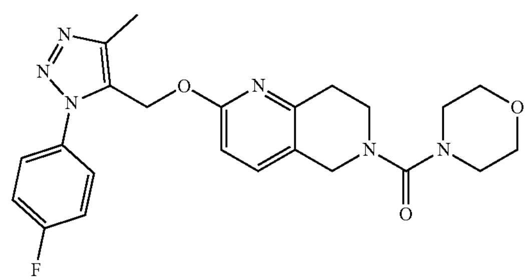 | 453.2 [M + H]⁺ | 2-{[1-(4-fluorophenyl)-4-methyl-1H-1,2,3-triazol-5-yl]methoxy}-6-(morpholine-4-carbonyl)-5,6,7,8-tetrahydro-1,6-naphthyridine |
| 81 | 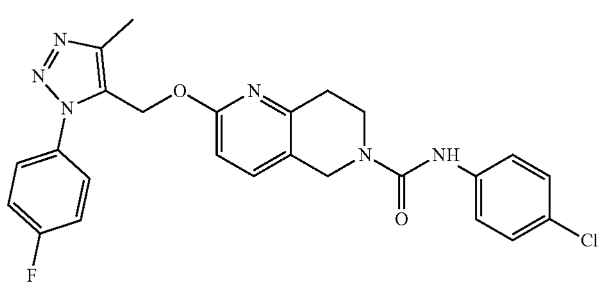 [SMILES: Cc1nnn(-c2ccc(F)cc2)c1COc1ccc2c(n1)CCN(C(=O)Nc1ccc(Cl)cc1)C2] | 492.9 [M + H]⁺ | N-(4-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide |
| 82 | 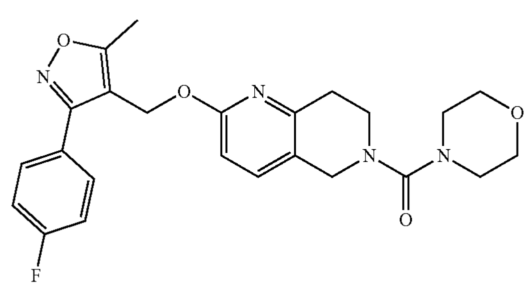 [SMILES: Cc1onc(-c2ccc(F)cc2)c1COc1ccc2c(n1)CCN(C(=O)N1CCOCC1)C2] | 453.1 | 2-{[3-(4-fluorophenyl)-5-methyl-1,2-oxazol-4-yl]methoxy}-6-(morpholine-4-carbonyl)-5,6,7,8-tetrahydro-1,6-naphthyridine |

TABLE 4-continued showing compounds synthesized according to Example 75:

| Ex. | Structure | MS m/z | Name |
|---|---|---|---|
| 83 | 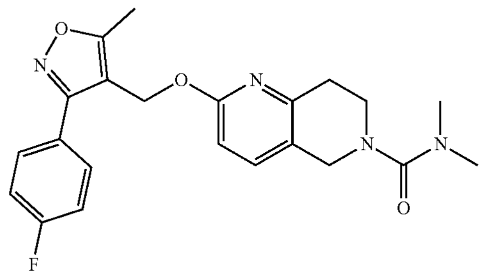 [SMILES: Cc1onc(-c2ccc(F)cc2)c1COc1ccc2c(n1)CCN(C(=O)N(C)C)C2] | 433.2 [M + Na]+ | 2-{[3-(4-fluorophenyl)-5-methyl-1,2-oxazol-4-yl]methoxy}-N,N-dimethyl-5,6,7,8-tetrahydro-1,6-naphthyridine-6-carboxamide |
| 84 | 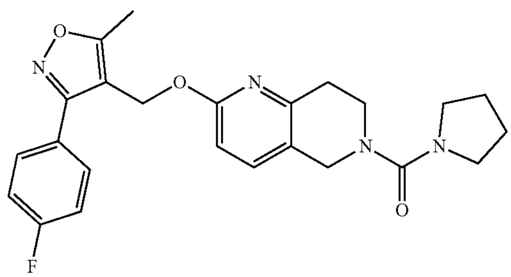 [SMILES: Cc1onc(-c2ccc(F)cc2)c1COc1ccc2c(n1)CCN(C(=O)N1CCCC1)C2] | 437.1 [M + H]+ | 2-{[3-(4-fluorophenyl)-5-methyl-1,2-oxazol-4-yl]methoxy}-6-(pyrrolidine-1-carbonyl)-5,6,7,8-tetrahydro-1,6-naphthyridine |
| 85 | 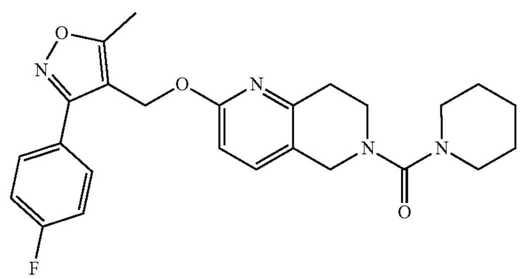 [SMILES: Cc1onc(-c2ccc(F)cc2)c1COc1ccc2c(n1)CCN(C(=O)N1CCCCC1)C2] | 473.3 [M + H]+ | 2-{[3-(4-fluorophenyl)-5-methyl-1,2-oxazol-4-yl]methoxy}-6-(piperidine-1-carbonyl)-5,6,7,8-tetrahydro-1,6-naphthyridine |
| 86 | 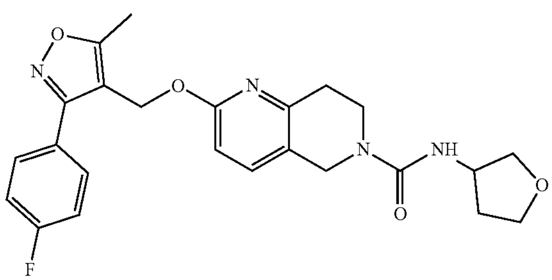 [SMILES: Cc1onc(-c2ccc(F)cc2)c1COc1ccc2c(n1)CCN(C(=O)NC1CCOC1)C2] | 453.2 [M + H]+ | 2-{[3-(4-fluorophenyl)-5-methyl-1,2-oxazol-4-yl]methoxy}-N-(oxolan-3-yl)-5,6,7,8-tetrahydro-1,6-naphthyridine-6-carboxamide |

Pharmaceutical Preparation Examples

The following formulation examples illustrate representative pharmaceutical compositions of this invention. The present invention however is not limited to the following pharmaceutical compositions.

A) Solid Oral Dosage Forms

I. Tablets

| | |
|---|---|
| Active ingredient(s) | 0.01-90% |
| Filler | 1-99.9% |
| Binder | 0-20% |
| Disintegrant | 0-20% |
| Lubricant | 0-10% |
| Other specific excipient(s) | 0-50% |

II. Orodispersible films

| | |
|---|---|
| Active ingredient(s) | 0.01-90% |
| Film forming agent | 1-99.9% |
| Plasticiser | 0-40% |
| Other specific excipient(s) | 0-50% |

B) Liquid Oral Dosage Forms

III. Oral suspensions

| | |
|---|---|
| Active ingredient(s) | 0.01-50% |
| Liquid vehicle | 10-99.9% |
| Wetting agent | 0-50% |
| Thickener | 0-50% |
| Buffering agent | q.s. |

-continued

|  |  |
|---|---|
| Osmotic agent | 0-50% |
| Preservatives | q.s. |

IV. Syrups

|  |  |
|---|---|
| Active ingredient(s) | 0.01-50% |
| Solvent | 10-99.9% |
| Sugar component | 1-20% |
| Flavouring agents | 0-10% |

C) Parenteral dosage forms
   V. Intravenous injections

|  |  |
|---|---|
| Active ingredient(s) | 0.01-50% |
| Solvent | 10-99.9% |
| Co-solvent | 0-99.9% |
| Osmotic agent | 0-50% |
| Buffering agent | q.s. |

D) Other dosage forms
VI. Suppositories

|  |  |
|---|---|
| Active ingredient(s) | 0.01-50% |
| Suppository base | 1-99.9% |
| Surface-active agents | 0-20% |
| Lubricant | 0-20% |
| Preservatives | q.s. |

VII. Eye drops

|  |  |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Bufferin agent | q.s. |
| Preservatives | q.s. |

VIII. Nasal Drops or Spray

|  |  |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Co-solvent | q.s. |
| Buffering agent | q.s. |
| Preservatives | q.s. |

The invention claimed is:
1. A compound of formula (I)

wherein
A is represented by group, group, or group, $R^1$ is hydrogen or halogen, n and m are each independently 1 or 2, $R^2$ is hydrogen; $C_{1-4}$alkyl optionally and independently substituted with one or more halogen, $C_{1-4}$alkoxy, —S(O)$_2$-C$_{1-4}$alkyl, or $R^3$; NR$^4$R$^5$ or R$^6$, $R^4$ and $R^5$ are each independently hydrogen, $C_{1-4}$alkyl or $R^7$; or $R^4$ and $R^5$ are taken together with the N to which they are attached to form a heterocycle, and $R^3$, $R^6$ and $R^7$ are optionally substituted carbocycle, heterocycle or heteroaryl; and pharmaceutically acceptable salts, geometric isomers, stereoisomers, enantiomers, racemates, diastereomers, biologically active metabolites, prodrugs, solvates, hydrates, and polymorphs thereof.

2. The compound according to claim 1 having formula (I-a), (I-a)

wherein $R^1$ is hydrogen or halogen, n and m are each independently 1 or 2, $R^2$ is hydrogen; $C_{1-4}$alkyl optionally and independently substituted with one or more halogen, $C_{1-4}$alkoxy, —S(O)$_2$-C$_{1-4}$alkyl, or $R^3$; NR$^4$R$^5$ or R$^6$, $R^4$ and $R^5$ are each independently hydrogen, $C_{1-4}$alkyl or $R^7$; or $R^4$ and $R^5$ are taken together with the N to which they are attached to form a heterocycle, and $R^3$, $R^6$ and $R^7$ are optionally substituted carbocycle, heterocycle or heteroaryl.

3. The compound according to claim 1 having formula (I-b),

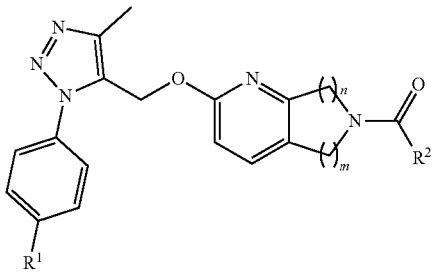

wherein
R$^1$ is hydrogen or halogen,
n and m are each independently 1 or 2,
R$^2$ is hydrogen; C$_{1-4}$alkyl optionally and independently substituted with one or more halogen, C$_{1-4}$alkoxy, —S(O)$_2$-C$_{1-4}$alkyl, or R$^3$; NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form a heterocycle, and
R$^3$, R$^6$ and R$^7$ are optionally substituted carbocycle, heterocycle or heteroaryl.

4. The compound according to claim 1 having formula (I-c),

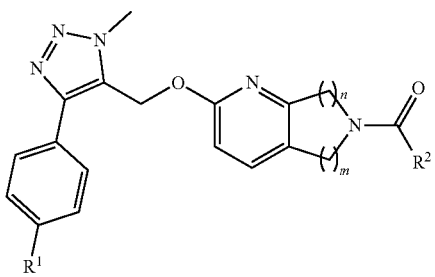

wherein
R$^1$ is hydrogen or halogen,
n and m are each independently 1 or 2,
R$^2$ is hydrogen; C$_{1-4}$alkyl optionally and independently substituted with one or more halogen, C$_{1-4}$alkoxy, —S(O)$_2$-C$_{1-4}$alkyl, or R$^3$; NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form a heterocycle, and
R$^3$, R$^6$ and R$^7$ are optionally substituted carbocycle, heterocycle or heteroaryl.

5. The compound according to claim 1, wherein
R$^1$ is halogen,
n is 1 and m is 2,
R$^2$ is C$_{1-4}$alkyl optionally and independently substituted with C$_{1-4}$alkoxy, or —S(O)$_2$-C$_{1-4}$alkyl; NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form a monocyclic heterocycle, and
R$^3$, R$^6$ and R$^7$ are optionally substituted C$_{3-10}$cycloalkyl, C$_{3-10}$cycloalkenyl, C$_{6-10}$-aryl, C$_{3-10}$heterocycle comprising 1, 2, 3 or 4 ring heteroatoms independently selected from N, O and S, or C$_{5-10}$heteroaryl comprising 1, 2, 3 or 4 heteroatoms independently selected from N, O and S.

6. The compound according to claim 1, wherein
R$^1$ is halogen,
n is 1 and m is 2,
R$^2$ is C$_{1-4}$alkyl optionally and independently substituted with C$_{1-4}$alkoxy, or —S(O)$_2$-C$_{1-4}$alkyl;
NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form a monocyclic heterocycle, and
R$^3$, R$^6$ and R$^7$ are optionally substituted C$_{3-10}$cycloalkyl, C$_{3-10}$cycloalkenyl, C$_{6-10}$-aryl, C$_{3-10}$heterocycle comprising 1, 2, 3 or 4 ring heteroatoms independently selected from N, O and S, or C$_{5-10}$heteroaryl comprising 1, 2, 3 or 4 heteroatoms independently selected from N, O and S.

7. The compound according to claim 1, wherein
R$^1$ is halogen,
n and m are 1, R$^2$ is C$_{1-4}$alkyl optionally and independently substituted with C$_{1-4}$alkoxy, or —S(O)$_2$-C$_{1-4}$alkyl;
NR$^4$R$^5$ or R$^6$,
R$^4$ and R$^5$ are each independently hydrogen, C$_{1-4}$alkyl or R$^7$; or R$^4$ and R$^5$ are taken together with the N to which they are attached to form a monocyclic heterocycle, and
R$^6$ and R$^7$ are optionally substituted C$_{3-10}$cycloalkyl, C$_{3-10}$cycloalkenyl, C$_{6-10}$-aryl, C$_{3-10}$heterocycle comprising 1, 2, 3 or 4 ring heteroatoms independently selected from N, O and S, or C$_{5-10}$heteroaryl comprising 1, 2, 3 or 4 heteroatoms independently selected from N, O and S.

8. The compound according to claim 1, wherein
R$^1$ is fluorine, bromine or chlorine,
R$^2$ is C$_{1-3}$alkyl, C$_{1-4}$alkoxy C$_{1-3}$alkyl, C$_{1-3}$alkyl-S(O)$_2$-C$_{1-3}$alkyl, NR$^4$R$^5$ or R$^6$,
R$^4$ and R$^5$ are each independently hydrogen, C$_{1-4}$alkyl or R$^7$, and
R$^6$ and R$^7$ are C$_{3-6}$cycloalkyl, C$_{6-10}$aryl, C$_{4-6}$heterocycle comprising 1 or 2 ring heteroatoms independently selected from N, O and S, or C$_{5-6}$heteroaryl comprising 1 or 2 ring heteroatoms independently selected from N and O, wherein R$^6$ and R$^7$ are optionally substituted with C$_{1-4}$alkyl, C$_{1-4}$alkoxy, halogen, haloC$_{1-4}$alkyl, haloC$_{1-4}$alkoxy, hydroxyl or oxo.

9. The compound according to claim 1, wherein
R$^1$ is fluorine or chlorine,
R$^2$ is C$_{1-4}$alkoxyC$_{1-3}$alkyl, methylsulfonylmethane, ethylsulfonylmethane, NR$^4$R$^5$ or R$^6$,
R$^4$ and R$^5$ are each independently hydrogen, C$_{1-3}$alkyl or R$^7$, and
R$^6$ and R$^7$ are cyclopropyl, cyclobutyl, cyclohexane, phenyl, oxetane, tetrahydrofuran, tetrahydropyran, thiane, pyrrolidine, piperidine, pyridine, isoxazole, pyrrole, or morpholine, wherein R$^6$ and R$^7$ are optionally substituted with C$_{1-4}$alkyl, C$_{1-4}$alkoxy, halogen, haloC$_{1-4}$alkyl, haloC$_{1-4}$alkoxy, hydroxyl or oxo.

10. The compound according to claim 1 selected from the group consisting of:
1-[2-{[3-(4-fluorophenyl)-5-methyl-1,2-oxazol-4-yl]methoxy}-7,8-dihydro-1,6-naphthyridin-6(5H)-yl]ethanone,
2-{[3-(4-fluorophenyl)-5-methyl-1,2-oxazol-4-yl]methoxy}-6-(oxolane-3-carbonyl)-5,6,7,8-tetrahydro-1,6-naphthyridine, 2-{[3-(4-fluorophenyl)-5-methyl-1,2-oxazol-4-yl]
methoxy}-6-(1,2-oxazole-5-carbonyl)-5,6,7,8-tetrahydro-1,6-naphthyridine,
6-cyclobutanecarbonyl-2-{[3-(4-fluorophenyl)-5-methyl-1,2-oxazol-4-yl]methoxy}-5,6,7,8-tetrahydro-1,6-naphthyridine,
6-cyclopropanecarbonyl-2-{[3-(4-fluorophenyl)-5-methyl-1,2-oxazol-4-yl]methoxy}-5,6,7,8-tetrahydro-1,6-naphthyridine,
4-(2-{[3-(4-fluorophenyl)-5-methyl-1,2-oxazol-4-yl]methoxy}-5,6,7,8-tetrahydro-1,6-naphthyridine-6-carbonyl)-1lambda6-thiane-1,1-dione,
2-{[3-(4-fluorophenyl)-5-methyl-1,2-oxazol-4-yl]methoxy}-6-(oxolane-2-carbonyl)-5,6,7,8-tetrahydro-1,6-naphthyridine,
1-(2-{[3-(4-fluorophenyl)-5-methyl-1,2-oxazol-4-yl]methoxy}-5,6,7,8-tetrahydro-1,6-naphthyridin-6-yl)-2-methanesulfonylethan-1-one,
2-{[3-(4-fluorophenyl)-5-methyl-1,2-oxazol-4-yl]methoxy}-6-(oxane-4-carbonyl)-5,6,7,8-tetrahydro-1,6-naphthyridine,
2-{[3-(4-fluorophenyl)-5-methyl-1,2-oxazol-4-yl]methoxy}-6-(5-methyl-1,2-oxazole-3-carbonyl)-5,6,7,8-tetrahydro-1,6-naphthyridine,
2-{[3-(4-fluorophenyl)-5-methyl-1,2-oxazol-4-yl]methoxy}-6-(1-methyl-1H-pyrrole-3-carbonyl)-5,6,7,8-tetrahydro-1,6-naphthyridine,
2,2,2-trifluoro-1-(2-{[3-(4-fluorophenyl)-5-methyl-1,2-oxazol-4-yl]methoxy}-5,6,7,8-tetrahydro-1,6-naphthyridin-6-yl)ethan-1-one,
4-(2-{[3-(4-fluorophenyl)-5-methyl-1,2-oxazol-4-yl]methoxy}-5,6,7,8-tetrahydro-1,6-naphthyridine-6-carbonyl)-1-methylpyrrolidin-2-one,
1-(2-{[1-(4-fluorophenyl)-4-methyl-1H-1,2,3-triazol-5-yl]methoxy}-5,6,7,8-tetrahydro-1,6-naphthyridin-6-yl)ethan-1-one,
2-{[1-(4-fluorophenyl)-4-methyl-1H-1,2,3-triazol-5-yl]methoxy}-6-(oxolane-2-carbonyl)-5,6,7,8-tetrahydro-1,6-naphthyridine,
2-{[1-(4-fluorophenyl)-4-methyl-1H-1,2,3-triazol-5-yl]methoxy}-6-(oxolane-3-carbonyl)-5,6,7,8-tetrahydro-1,6-naphthyridine,
2-{[1-(4-fluorophenyl)-4-methyl-1H-1,2,3-triazol-5-yl]methoxy}-6-[(3R)-oxolane-3-carbonyl]-5,6,7,8-tetrahydro-1,6-naphthyridine,
2-{[1-(4-fluorophenyl)-4-methyl-1H-1,2,3-triazol-5-yl]methoxy}-6-[(3S)-oxolane-3-carbonyl]-5,6,7,8-tetrahydro-1,6-naphthyridine,
6-cyclopropanecarbonyl-2-{[1-(4-fluorophenyl)-4-methyl-1H-1,2,3-triazol-5-yl]methoxy}-5,6,7,8-tetrahydro-1,6-naphthyridine,
2-{[1-(4-fluorophenyl)-4-methyl-1H-1,2,3-triazol-5-yl]methoxy}-6-(1,2-oxazole-5-carbonyl)-5,6,7,8-tetrahydro-1,6-naphthyridine,
4-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one,
1-(2-{[1-(4-fluorophenyl)-4-methyl-1H-1,2,3-triazol-5-yl]methoxy}-5,6,7,8-tetrahydro-1,6-naphthyridin-6-yl)-2-methylpropan-1-one,
4-(2-{[1-(4-fluorophenyl)-4-methyl-1H-1,2,3-triazol-5-yl]methoxy}-5,6,7,8-tetrahydro-1,6-naphthyridine-6-carbonyl)-1lambda6-thiane-1,1-dione,
1-(2-{[1-(4-fluorophenyl)-4-methyl-1H-1,2,3-triazol-5-yl]methoxy}-5,6,7,8-tetrahydro-1,6-naphthyridin-6-yl)propan-1-one,
2-{[1-(4-fluorophenyl)-4-methyl-1H-1,2,3-triazol-5-yl]methoxy}-6-(pyridine-4-carbonyl)-5,6,7,8-tetrahydro-1,6-naphthyridine,
2-{[1-(4-fluorophenyl)-4-methyl-1H-1,2,3-triazol-5-yl]methoxy}-6-(pyridine-2-carbonyl)-5,6,7,8-tetrahydro-1,6-naphthyridine,
6-(3-chlorobenzoyl)-2-{[1-(4-fluorophenyl)-4-methyl-1H-1,2,3-triazol-5-yl]methoxy}-5,6,7,8-tetrahydro-1,6-naphthyridine,
2-{[1-(4-fluorophenyl)-4-methyl-1H-1,2,3-triazol-5-yl]methoxy}-6-(oxane-4-carbonyl)-5,6,7,8-tetrahydro-1,6-naphthyridine,
2-{[1-(4-chlorophenyl)-4-methyl-1H-1,2,3-triazol-5-yl]methoxy}-6-(oxolane-3-carbonyl)-5,6,7,8-tetrahydro-1,6-naphthyridine,
2-{[1-(4-fluorophenyl)-4-methyl-1H-1,2,3-triazol-5-yl]methoxy}-6-(oxane-3-carbonyl)-5,6,7,8-tetrahydro-1,6-naphthyridine,
2-{[1-(4-fluorophenyl)-4-methyl-1H-1,2,3-triazol-5-yl]methoxy}-6-(3-methyloxolane-3-carbonyl)-5,6,7,8-tetrahydro-1,6-naphthyridine,
2-{[1-(4-chlorophenyl)-4-methyl-1H-1,2,3-triazol-5-yl]methoxy}-6-(oxane-4-carbonyl)-5,6,7,8-tetrahydro-1,6-naphthyridine,
2-{[1-(4-chlorophenyl)-4-methyl-1H-1,2,3-triazol-5-yl]methoxy}-6-(pyridine-4-carbonyl)-5,6,7,8-tetrahydro-1,6-naphthyridine,
1-(2-{[1-(4-fluorophenyl)-4-methyl-1H-1,2,3-triazol-5-yl]methoxy}-5,6,7,8-tetrahydro-1,7-naphthyridin-7-yl)ethan-1-one,
2-{[1-(4-fluorophenyl)-4-methyl-1H-1,2,3-triazol-5-yl]methoxy}-6-(4-methoxycyclohexanecarbonyl)-5,6,7,8-tetrahydro-1,6-naphthyridine,
1-(2-{[1-(4-chlorophenyl)-4-methyl-1H-1,2,3-triazol-5-yl]methoxy}-5,6,7,8-tetrahydro-1,6-naphthyridin-6-yl)ethan-1-one,
2-{[1-(4-fluorophenyl)-4-methyl-1H-1,2,3-triazol-5-yl]methoxy}-6-[6-(trifluoromethyl)pyridine-3-carbonyl]-5,6,7,8-tetrahydro-1,6-naphthyridine,
2-{[1-(4-chlorophenyl)-4-methyl-1H-1,2,3-triazol-5-yl]methoxy}-6-[(3S)-oxolane-3-carbonyl]-5,6,7,8-tetrahydro-1,6-naphthyridine,
2-{[1-(4-fluorophenyl)-4-methyl-1H-1,2,3-triazol-5-yl]methoxy}-6-(pyridine-3-carbonyl)-5,6,7,8-tetrahydro-1,6-naphthyridine,
(5S)-5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one,
(5R)-5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpyrrolidin-2-one,
1-(2-{[1-(4-chlorophenyl)-4-methyl-1H-1,2,3-triazol-5-yl]methoxy}-5,6,7,8-tetrahydro-1,6-naphthyridin-6-yl)-2-methoxyethan-1-one,
1-ethyl-4-(2-{[1-(4-fluorophenyl)-4-methyl-1H-1,2,3-triazol-5-yl]methoxy}-5,6,7,8-tetrahydro-1,6-naphthyridine-6-carbonyl)pyrrolidin-2-one,
4-(2-{[1-(4-fluorophenyl)-4-methyl-1H-1,2,3-triazol-5-yl]methoxy}-5,6,7,8-tetrahydro-1,6-naphthyridine-6-carbonyl)-1-(propan-2-yl)pyrrolidin-2-one,
1-(2-{[1-(4-fluorophenyl)-4-methyl-1H-1,2,3-triazol-5-yl]methoxy}-5H,6H,7H-pyrrolo[3,4-b]pyridin-6-yl)ethan-1-one,
5-(2-{[1-(4-fluorophenyl)-4-methyl-1H-1,2,3-triazol-5-yl]methoxy}-5,6,7,8-tetrahydro-1,6-naphthyridine-6-carbonyl)-1-methylpiperidin-2-one, cyclopropyl(2-{[1-(4-fluorophenyl)-4-methyl-1H-1,2,3-triazol-5-yl]methoxy}-5,7-dihydro-6H-pyrrolo[3,4-b]pyridin-6-yl)methanone, 1-(2-{[3-(4-fluorophenyl)-5-methyl-1,2-oxazol-4-yl]methoxy}-5,6,7,8-tetrahydro-1,6-naphthyridin-6-yl)-3-methanesulfonylpropan-1-one, 1-(2-{[3-(4-fluorophenyl)-5-methyl-1,2-oxazol-4-yl]methoxy}-5H,6H,7H-pyrrolo[3,4-b]pyridin-6-yl)-2-methanesulfonylethan-1-one, 1-(2-{[3-(4-fluorophenyl)-5-methyl-1,2-oxazol-4-yl]methoxy}-5,7-dihydro-6H-pyrrolo[3,4-b]pyridin-6-yl)ethanone, 2,2,2-trifluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone, 1-(2-{[1-(4-fluorophenyl)-4-methyl-1H-1,2,3-triazol-5-yl]methoxy}-5,7-dihydro-6H-pyrrolo[3,4-b]pyridin-6-yl)propan-1-one, 2,2-difluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone, 2-fluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethanone, 1-(4-fluorophenyl)-4-methyl-5-({[6-(oxane-4-carbonyl)-5H,6H,7H-pyrrolo[3,4-b]pyridin-2-yl]oxy}methyl)-1H-1,2,3-triazole, 1-(2-{[1-(4-fluorophenyl)-4-methyl-1H-1,2,3-triazol-5-yl]methoxy}-5H,6H,7H-pyrrolo[3,4-b]pyridin-6-yl)-3-methylbutan-1-one, 5-[({6-cyclobutanecarbonyl-5H,6H,7H-pyrrolo[3,4-b]pyridin-2-yl}oxy)methyl]-1-(4-fluorophenyl)-4-methyl-1H-1,2,3-triazole, 1-(2-{[1-(4-fluorophenyl)-4-methyl-1H-1,2,3-triazol-5-yl]methoxy}-5H,6H,7H-pyrrolo[3,4-b]pyridin-6-yl)-2-methylpropan-1-one, 1-(2-{[1-(4-fluorophenyl)-4-methyl-1H-1,2,3-triazol-5-yl]methoxy}-5H,6H,7H-pyrrolo[3,4-b]pyridin-6-yl)-2,2-dimethylpropan-1-one, 1-(2-{[1-(4-chlorophenyl)-4-methyl-1H-1,2,3-triazol-5-yl]methoxy}-5,7-dihydro-6H-pyrrolo[3,4-b]pyridin-6-yl)ethanone, 1-(4-fluorophenyl)-4-methyl-5-({[6-(oxolane-2-carbonyl)-5H,6H,7H-pyrrolo[3,4-b]pyridin-2-yl]oxy}methyl)-1H-1,2,3-triazole, 1-(4-fluorophenyl)-4-methyl-5-({[6-(oxolane-3-carbonyl)-5H,6H,7H-pyrrolo[3,4-b]pyridin-2-yl]oxy}methyl)-1H-1,2,3-triazole, 1-(4-fluorophenyl)-4-methyl-5-({[6-(oxane-3-carbonyl)-5H,6H,7H-pyrrolo[3,4-b]pyridin-2-yl]oxy}methyl)-1H-1,2,3-triazole, 4-(2-{[1-(4-fluorophenyl)-4-methyl-1H-1,2,3-triazol-5-yl]methoxy}-5H,6H,7H-pyrrolo[3,4-b]pyridine-6-carbonyl)pyridine, 3-(2-{[1-(4-fluorophenyl)-4-methyl-1H-1,2,3-triazol-5-yl]methoxy}-5H,6H,7H-pyrrolo[3,4-b]pyridine-6-carbonyl)pyridine, 2-(2-{[1-(4-fluorophenyl)-4-methyl-1H-1,2,3-triazol-5-yl]methoxy}-5H,6H,7H-pyrrolo[3,4-b]pyridine-6-carbonyl)pyridine, 1-(2-{[4-(4-fluorophenyl)-1-methyl-1H-1,2,3-triazol-5-yl]methoxy}-5,7-dihydro-6H-pyrrolo[3,4-b]pyridin-6-yl)ethanone, 1-(2-{[4-(4-chlorophenyl)-1-methyl-1H-1,2,3-triazol-5-yl]methoxy}-5,7-dihydro-6H-pyrrolo[3,4-b]pyridin-6-yl)ethanone, 1-(2-{[4-(4-fluorophenyl)-1-methyl-1H-1,2,3-triazol-5-yl]methoxy}-5,7-dihydro-6H-pyrrolo[3,4-b]pyridin-6-yl)propan-1-one, 2-fluoro-1-(2-{[4-(4-fluorophenyl)-1-methyl-1H-1,2,3-triazol-5-yl]methoxy}-5,7-dihydro-6H-pyrrolo[3,4-b]pyridin-6-yl)ethanone, 4-(4-fluorophenyl)-1-methyl-5-({[6-(oxolane-3-carbonyl)-5H,6H,7H-pyrrolo[3,4-b]pyridin-2-yl]oxy}methyl)-1H-1,2,3-triazole, 1-(2-{[4-(4-fluorophenyl)-1-methyl-1H-1,2,3-triazol-5-yl]methoxy}-5H,6H,7H-pyrrolo[3,4-b]pyridin-6-yl)-2-methylpropan-1-one, 4-(4-fluorophenyl)-1-methyl-5-({[6-(oxolane-2-carbonyl)-5H,6H,7H-pyrrolo[3,4-b]pyridin-2-yl]oxy}methyl)-1H-1,2,3-triazole, 4-(4-fluorophenyl)-1-methyl-5-({[6-(oxane-3-carbonyl)-5H,6H,7H-pyrrolo[3,4-b]pyridin-2-yl]oxy}methyl)-1H-1,2,3-triazole, 2-{[1-(4-fluorophenyl)-4-methyl-1H-1,2,3-triazol-5-yl]methoxy}-N-(1-methyl-5-oxopyrrolidin-3-yl)-5,6,7,8-tetrahydro-1,6-naphthyridine-6-carboxamide, 2-{[1-(4-fluorophenyl)-4-methyl-1H-1,2,3-triazol-5-yl]methoxy}-N,N-dimethyl-5,6,7,8-tetrahydro-1,6-naphthyridine-6-carboxamide, 2-{[1-(4-fluorophenyl)-4-methyl-1H-1,2,3-triazol-5-yl]methoxy}-6-(pyrrolidine-1-carbonyl)-5,6,7,8-tetrahydro-1,6-naphthyridine, 2-{[1-(4-fluorophenyl)-4-methyl-1H-1,2,3-triazol-5-yl]methoxy}-N-(oxolan-3-yl)-5,6,7,8-tetrahydro-1,6-naphthyridine-6-carboxamide, N-(2-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide, 2-{[1-(4-fluorophenyl)-4-methyl-1H-1,2,3-triazol-5-yl]methoxy}-6-(morpholine-4-carbonyl)-5,6,7,8-tetrahydro-1,6-naphthyridine, N-(4-chlorophenyl)-2-{[1-(4-fluorophenyl)-4-methyl-1H-1,2,3-triazol-5-yl]methoxy}-5,6,7,8-tetrahydro-1,6-naphthyridine-6-carboxamide, 2-{[3-(4-fluorophenyl)-5-methyl-1,2-oxazol-4-yl]methoxy}-6-(morpholine-4-carbonyl)-5,6,7,8-tetrahydro-1,6-naphthyridine, 2-{[3-(4-fluorophenyl)-5-methyl-1,2-oxazol-4-yl]methoxy}-N,N-dimethyl-5,6,7,8-tetrahydro-1,6-naphthyridine-6-carboxamide, 2-{[3-(4-fluorophenyl)-5-methyl-1,2-oxazol-4-yl]methoxy}-6-(pyrrolidine-1-carbonyl)-5,6,7,8-tetrahydro-1,6-naphthyridine, 2-{[3-(4-fluorophenyl)-5-methyl-1,2-oxazol-4-yl]methoxy}-6-(piperidine-1-carbonyl)-5,6,7,8-tetrahydro-1,6-naphthyridine, and 2-{[3-(4-fluorophenyl)-5-methyl-1,2-oxazol-4-yl]methoxy}-N-(oxolan-3-yl)-5,6,7,8-tetrahydro-1,6-naphthyridine-6-carboxamide.

11. A pharmaceutical composition comprising as active ingredient at least one compound according to claim 1 and at least one pharmaceutically acceptable excipient.

12. The pharmaceutical composition according to claim 11, further comprising one or more other active ingredients.

13. A method of treating diseases related to the GABA$_A$ α5 receptor or providing cognitive enhancement, comprising administering to a subject in need of such treatment or cognition enhancement, the compounds according to claim 1.

14. The method according to claim 13, wherein the disease related to the GABA$_A$ α5 receptor is selected from the group consisting of neurodegenerative disorders, neurocognitive disorders, schizophrenia, mood disorders, pain disorders, and substance-related and addictive disorders.

15. The method according to claim 13, wherein the disease related to the GABA$_A$ α5 receptor is selected from the group consisting of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD), and schizophrenia.

16. The method according to claim 13, further comprising administering one or more other active ingredients.

17. The compound according to claim 1, wherein the compound of formula (I) is a geometric isomer, biologically active metabolite, prodrug, or polymorph thereof.

18. The compound according to claim 1 selected from the group consisting of:
  2-{[3-(4-fluorophenyl)-5-methyl-1,2-oxazol-4-yl]methoxy}-6-(oxolane-3-carbonyl)-5,6,7,8-tetrahydro-1,6-naphthyridine,
  4-(2-{[3-(4-fluorophenyl)-5-methyl-1,2-oxazol-4-yl]methoxy}-5,6,7,8-tetrahydro-1,6-naphthyridine-6-carbonyl)-1lambda6-thiane-1,1-dione,
  1-(2-{[3-(4-fluorophenyl)-5-methyl-1,2-oxazol-4-yl]methoxy}-5,6,7,8-tetrahydro-1,6-naphthyridin-6-yl)-2-methanesulfonylethan-1-one,
  2-{[3-(4-fluorophenyl)-5-methyl-1,2-oxazol-4-yl]methoxy}-6-(oxane-4-carbonyl)-5,6,7,8-tetrahydro-1,6-naphthyridine,
  4-(2-{[3-(4-fluorophenyl)-5-methyl-1,2-oxazol-4-yl]methoxy}-5,6,7,8-tetrahydro-1,6-naphthyridine-6-carbonyl)-1-methylpyrrolidin-2-one,
  1-(2-{[1-(4-fluorophenyl)-4-methyl-1H-1,2,3-triazol-5-yl]methoxy}-5,6,7,8-tetrahydro-1,6-naphthyridin-6-yl)ethan-1-one,
  2-{[1-(4-fluorophenyl)-4-methyl-1H-1,2,3-triazol-5-yl]methoxy}-6-(oxolane-2-carbonyl)-5,6,7,8-tetrahydro-1,6-naphthyridine,
  2-{[1-(4-fluorophenyl)-4-methyl-1H-1,2,3-triazol-5-yl]methoxy}-6-(oxolane-3-carbonyl)-5,6,7,8-tetrahydro-1,6-naphthyridine,
  4-(2-{[1-(4-fluorophenyl)-4-methyl-1H-1,2,3-triazol-5-yl]methoxy}-5,6,7,8-tetrahydro-1,6-naphthyridine-6-carbonyl)-1lambda6-thiane-1,1-dione,
  2-{[1-(4-fluorophenyl)-4-methyl-1H-1,2,3-triazol-5-yl]methoxy}-6-(pyridine-4-carbonyl)-5,6,7,8-tetrahydro-1,6-naphthyridine,
  2-{[1-(4-fluorophenyl)-4-methyl-1H-1,2,3-triazol-5-yl]methoxy}-6-(oxane-4-carbonyl)-5,6,7,8-tetrahydro-1,6-naphthyridine,
  2-{[1-(4-chlorophenyl)-4-methyl-1H-1,2,3-triazol-5-yl]methoxy}-6-(oxolane-3-carbonyl)-5,6,7,8-tetrahydro-1,6-naphthyridine,
  2-{[1-(4-chlorophenyl)-4-methyl-1H-1,2,3-triazol-5-yl]methoxy}-6-(oxane-4-carbonyl)-5,6,7,8-tetrahydro-1,6-naphthyridine,
  1-ethyl-4-(2-{[1-(4-fluorophenyl)-4-methyl-1H-1,2,3-triazol-5-yl]methoxy}-5,6,7,8-tetrahydro-1,6-naphthyridine-6-carbonyl)pyrrolidin-2-one,
  1-(2-{[1-(4-fluorophenyl)-4-methyl-1H-1,2,3-triazol-5-yl]methoxy}-5H,6H,7H-pyrrolo[3,4-b]pyridin-6-yl)ethan-1-one,
  cyclopropyl(2-{[1-(4-fluorophenyl)-4-methyl-1H-1,2,3-triazol-5-yl]methoxy}-5,7-dihydro-6H-pyrrolo[3,4-b]pyridin-6-yl)methanone,
  1-(2-{[3-(4-fluorophenyl)-5-methyl-1,2-oxazol-4-yl]methoxy}-5H,6H,7H-pyrrolo[3,4-b]pyridin-6-yl)-2-methanesulfonylethan-1-one,
  2,2-difluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethenone,
  2-fluoro-1-(2-{[1-(4-fluorophenyl)-4-methyl-1H-1,2,3-triazol-5-yl]methoxy}-5,7-dihydro-6H-pyrrolo[3,4-b]pyridin-6-yl)ethenone,
  1-(4-fluorophenyl)-4-methyl-5-({[6-(oxane-4-carbonyl)-5H,6H,7H-pyrrolo[3,4-b]pyridin-2-yl]oxy}methyl)-1H-1,2,3-triazole,
  1-(2-{[1-(4-fluorophenyl)-4-methyl-1H-1,2,3-triazol-5-yl]methoxy}-5H,6H,7H-pyrrolo[3,4-b]pyridin-6-yl)-3-methylbutan-1-one,
  1-(2-{[1-(4-fluorophenyl)-4-methyl-1H-1,2,3-triazol-5-yl]methoxy}-5H,6H,7H-pyrrolo[3,4-b]pyridin-6-yl)-2-methylpropan-1-one,
  1-(2-{[1-(4-chlorophenyl)-4-methyl-1H-1,2,3-triazol-5-yl]methoxy}-5,7-dihydro-6H-pyrrolo[3,4-b]pyridin-6-yl)ethenone,
  1-(4-fluorophenyl)-4-methyl-5-({[6-(oxolane-2-carbonyl)-5H,6H,7H-pyrrolo[3,4-b]pyridin-2-yl]oxy}methyl)-1H-1,2,3-triazole,
  1-(4-fluorophenyl)-4-methyl-5-({[6-(oxolane-3-carbonyl)-5H,6H,7H-pyrrolo[3,4-b]pyridin-2-yl]oxy}methyl)-1H-1,2,3-triazole,
  1-(4-fluorophenyl)-4-methyl-5-({[6-(oxane-3-carbonyl)-5H,6H,7H-pyrrolo[3,4-b]pyridin-2-yl]oxy}methyl)-1H-1,2,3-triazole,
  4-(2-{[1-(4-fluorophenyl)-4-methyl-1H-1,2,3-triazol-5-yl]methoxy}-5H,6H,7H-pyrrolo[3,4-b]pyridine-6-carbonyl)pyridine,
  3-(2-{[1-(4-fluorophenyl)-4-methyl-1H-1,2,3-triazol-5-yl]methoxy}-5H,6H,7H-pyrrolo[3,4-b]pyridine-6-carbonyl)pyridine,
  2-{[1-(4-fluorophenyl)-4-methyl-1H-1,2,3-triazol-5-yl]methoxy}-N-(1-methyl-5-oxopyrrolidin-3-yl)-5,6,7,8-tetrahydro-1,6-naphthyridine-6-carboxamide, and
  2-{[1-(4-fluorophenyl)-4-methyl-1H-1,2,3-triazol-5-yl]methoxy}-N-(oxolan-3-yl)-5,6,7,8-tetrahydro-1,6-naphthyridine-6-carboxamide.

19. A compound of formula (IX)

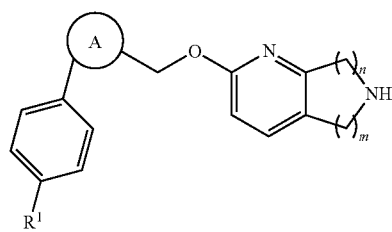

(IX)

wherein
A is represented by

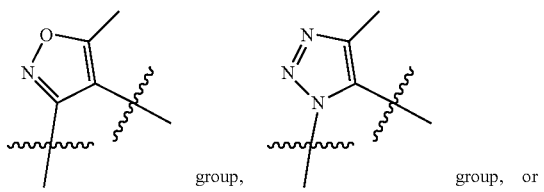

group, group, or

-continued
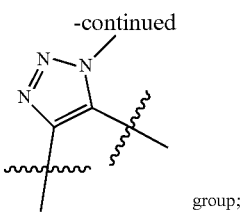
group;
$R^1$ is hydrogen or halogen; and
n and m are each independently 1 or 2.
* * * * *